United States Patent
Poirier et al.

(10) Patent No.: US 11,230,602 B2
(45) Date of Patent: Jan. 25, 2022

(54) NON-ANTAGONISTIC ANTIBODIES DIRECTED AGAINST THE ALPHA CHAIN OF THE IL7 RECEPTOR EXTRACELLULAR DOMAIN AND USE THEREOF IN CANCER TREATMENT

(71) Applicant: OSE IMMUNOTHERAPEUTICS, Nantes (FR)

(72) Inventors: Nicolas Poirier, Treillieres (FR); Caroline Mary, Sainte-Pazanne (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 504 days.

(21) Appl. No.: 16/080,572

(22) PCT Filed: Feb. 28, 2017

(86) PCT No.: PCT/IB2017/000293
§ 371 (c)(1),
(2) Date: Aug. 28, 2018

(87) PCT Pub. No.: WO2017/149394
PCT Pub. Date: Sep. 8, 2017

(65) Prior Publication Data
US 2020/0308288 A1 Oct. 1, 2020

Related U.S. Application Data

(60) Provisional application No. 62/301,271, filed on Feb. 29, 2016.

(51) Int. Cl.
*A61K 39/00* (2006.01)
*C07K 16/28* (2006.01)
*A61K 45/06* (2006.01)

(52) U.S. Cl.
CPC .......... *C07K 16/2866* (2013.01); *A61K 45/06* (2013.01); *A61K 2039/505* (2013.01); *C07K 2317/24* (2013.01); *C07K 2317/34* (2013.01); *C07K 2317/53* (2013.01); *C07K 2317/54* (2013.01); *C07K 2317/55* (2013.01); *C07K 2317/565* (2013.01); *C07K 2317/622* (2013.01); *C07K 2317/624* (2013.01); *C07K 2317/732* (2013.01); *C07K 2317/94* (2013.01); *C07K 2319/03* (2013.01)

(58) Field of Classification Search
None
See application file for complete search history.

(56) References Cited

U.S. PATENT DOCUMENTS 9,447,182 B2 * 9/2016 Brouard ............... A61P 37/08
2011/0028700 A1 2/2011 Heal
2015/0297310 A1 10/2015 Khleif et al.

FOREIGN PATENT DOCUMENTS

| WO | 2007140472 A2 | 12/2007 |
| WO | 2010017468 A1 | 2/2010 |
| WO | 2010085643 A1 | 7/2010 |
| WO | 2011094259 A2 | 8/2011 |
| WO | 2011104687 A1 | 9/2011 |
| WO | 2013056984 A1 | 4/2013 |
| WO | 2015189302 A1 | 12/2015 |

OTHER PUBLICATIONS

Adams et al., "Heterologous immunity provides a potent barrier to transplantation tolerance," The journal of Clinical Investigation, Jun. 2003, pp. 1887-1895 vol. 111 No. 12.
Belarif et al., "IL-7 receptor blockade blunts antigen-specific memory T cell responses and chronic inflammation in primates," Nature communications| (2018) 9:4483 | DOI: 10.1038/s41467-018-06804-y.
Chung Brile et al., "Prevention of Graft-versus-host Disease by anti-IL-7RAlpha Antibody," Blood journal, Oct. 15, 2007, pp. 2803-2810, vol. 110 No. 8.
Colman et al., "Effects of amino acid sequence changes on antibody-antigen interactions," Research in immunology, 1994, pp. 33-36, vol. 145.
Janeway et al., "Antigen recognition by B-cells and T-cell receptors," Immunobiology, 5th Edition, pp. 100-105, Chapters 3, 2001.
Kudernatsch et al., "Human bone marrow contains a subset of quiescent early memory CD8+ T cells characterized by high CD127 expression and efflux capacity: cellular immune response," European journal of Immunology, vol. 44 No. 12, pp. 3532-3542, 2014.
Liu Weihong et al., "CD127 expression inversely correlates with FoxP3 and suppressive function of human CD4+ T reg cells," The journal of experimental medicine, Rockefeller university press, US, vol. 203 No. 7, pp. 1701-1711, 2006.
Liu et al., "Crucial role of Interleukine-7 in T helper type 17 survival and expansion in autoimmune disease," Nature Medicine, Feb. 2010, pp. 191-199 vol. 16 No. 2.
Liu et al., "Retraction: Crucial role of Interleukine-7 in T helper type 17 survival and expansion in autoimmune disease," Nature Medicine, Feb. 2013, pp. 1673 vol. 19 No. 12.

(Continued)

*Primary Examiner* — Laura B Goddard
(74) *Attorney, Agent, or Firm* — Thompson Coburn LLP; William A. Holtz

(57) ABSTRACT

The description concerns humanized antibodies directed against the extracellular domain of the alpha chain of the receptor for interleukin-7 (IL-7), especially against the receptor for human IL-7 expressed on human cells (also designated human IL-7Ralpha or IL-7Ra or CD127) and which do not interfere with the IL-7 or TSLP signaling pathways. The antibodies described do not have an antagonistic effect on the IL-7 receptor, but may still present cytotoxic activity against CD127 positive cells. In a particular embodiment, the antibody does not have an agonist effect on the IL-7 receptor.

28 Claims, 9 Drawing Sheets

Specification includes a Sequence Listing.

(56) References Cited

OTHER PUBLICATIONS

Mai HL, Boeffard F, Longis J, Danger R, Martinet B, Haspot F, Vanhove B, Brouard S, Soulillou JP., "IL-7 receptor blockade following T cell depletion promotes long-term allograft survival," J Clin Invest. Apr. 2014;124(4):1723-33.

Michel et al., "Patients with relapsing-remitting multiple sclerosis have normal Treg function when cells expressing IL-7 receptor alpha-chain are excluded from the analysis," The journal of clinical investigation, Oct. 2008, pp. 3411-3419, vol. 118 No. 10.

Natalia Marek et al., "The time is crucial for Ex vivo expansion of T regulatory cells for therapy," Cell Transplantation, vol. 20 No. 11, pp. 1747-1758, 2011.

Paul et al., "FV structure and diversity in three dimensions," Fundamental immunology, 3rd Edition, 1993, pp. 292-295, Chapter 9, Raven press Ltd., New York.

Racape et al., "Interleukin 7 Receptor Alpha as potential therapeutic target in transplantation," Archivum Immunologiae et Therapia Experimentalis, 2009, pp. 253-261.

Rudikoff et al., "Single amino acid substitution altering antigen-binding specifity," Proceedings of the National Academy of Sciences USA, Mar. 1982, pp. 1979-1983, vol. 79.

Tamura et al., "Structural correlates of an anticarcinoma antibody: identification of specificity-determining residues (SDRs) and development of a minimally immunogenic antibody variant by retention of SDRs only," The journal of Immunology, pp. 1432-1441, vol. 164, 2000.

Touil et al., "Depletion of T regulatory cells through selection of CD127-positive cells result in a population enriched in memory T cells: implications for anti-tumor cell therapy," Haematologica, the Hematology journal: Official organ of the European Hematology Association, vol. 97 No. 11, pp. 1678-1685, 2012.

Volker Schirrmacher, "Cancer-reactive memory T cells from bone marrow: Spontaneous induction and therapeutic potential (review)," International journal of Oncology, vol. 47 No. 6, pp. 2005-2016, 2015.

* cited by examiner

ESGYAQNGDLEDAELDDYSFSCYSQLEVNGSQHSLTCAFEDPDVNTTNLE
FEICGALVEVKCLNFRKLQEIYFIETKKFLLIGKSNICVKVGEKSLTCKKIDLTTI
VKPEAPFDLSVIYREGANDFVVTFNTSHLQKKYVKVLMHDVAYRQEKDE
NKWTHVNLSSTKLTLLQRKLQPAAMYEIKVRSIPDHYFKGFWSEWSPSYY
FRTPEINNSSGEMD

Figure 5

MLVLQWLVTALFGGVHCAVQLVESGGGLVQPGGSLKLTCAASGFTFTMAMMWVRQAPGKGLEWVARIKTK

ANNYATYYADSVKGRFTISRDDSKSTVYLQMDSVKTEDTATYYCVWLTTRDYDYWGQGVLVTVSSASTKGP

SVFPLAPSSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFLYSKLTVDKSRWQQGNVFSCSVMHEA

LHNHYTQKSLSLSPGK

FIGURE 6

MKFPAQFLGLVLQPGATGDIVLTQSPSSLPVTPGEPASISCRSSQSLLYSDGYTYLNWFLQKPGQSPKLLIYRMSN

RDSGVPDRFSGSGSGTDFTLKISRVEAEDVGTYYCMQGLEFPYTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACEVTHQGLSSPVTKS

FNRGEC

FIGURE 7

SEQUENCE LISTING

```
<160> NUMBER OF SEQ ID NOS: 109

<210> SEQ ID NO 1
<211> LENGTH: 369
<212> TYPE: DNA
<213> ORGANISM: Artificial Sequence
<220> FEATURE:
<223> OTHER INFORMATION: Effi3 VHvar3

<400> SEQUENCE: 1
gctgtgcagc tggtcgaatc tgggggggggg ctggtccagc ccggcgggtc tctgaaaatc     60
acttgcgccg ctagtgggtt cacctttaca aacgcagcca tgtactgggt ccgacaggct    120
cctggaaagg gcctggagtg ggtggcacgg atcagaacaa aggctaacaa ctacgcaact    180
tactatgccg actcagtgaa gggcaggttc accattagcc gcgacgatag caaatccaca    240
gtctacctgc agatggactc tgtgaagaca gaagatactg ccacctacta ttgtattgtg    300
gtcgtgctga ctactacacg ggattacttt gactattggg gacagggagt gctggtgaca    360
gtgagttca                                                            369

<210> SEQ ID NO 2
<211> LENGTH: 123
<212> TYPE: PRT
<213> ORGANISM: Artificial Sequence
<220> FEATURE:
<223> OTHER INFORMATION: Effi3 VHvar3_aa

<400> SEQUENCE: 2

Ala Val Gln Leu Val Glu Ser Gly Gly Gly Leu Val Gln Pro Gly Gly
1               5                   10                  15

Ser Leu Lys Ile Thr Cys Ala Ala Ser Gly Phe Thr Phe Thr Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Ala Asn Asn Tyr Ala Thr Tyr Tyr Ala Asp
    50                  55                  60

Ser Val Lys Gly Arg Phe Thr Ile Ser Arg Asp Asp Ser Lys Ser Thr
65                  70                  75                  80

Val Tyr Leu Gln Met Asp Ser Val Lys Thr Glu Asp Thr Ala Thr Tyr
                85                  90                  95

Tyr Cys Ile Val Val Leu Thr Thr Thr Arg Asp Tyr Phe Asp Tyr
            100                 105                 110

Trp Gly Gln Gly Val Leu Val Thr Val Ser Ser
        115                 120

<210> SEQ ID NO 3
```

<211> LENGTH: 339
<212> TYPE: DNA
<213> ORGANISM: Artificial Sequence
<220> FEATURE:
<223> OTHER INFORMATION: Effi3 VLvar3

<400> SEQUENCE: 3

```
gacatcgtcc tgactcagtc ccctcttcc ctgccagtga cacctggaga gccagcatct    60
atcagttgcc gaagctccca gtcactgctg actgtcaagg gaattaccag cctgtactgg   120
ttcctgcaga agcccggcca gtcccctaaa ctgctgatct atcggatgtc taacagagac   180
agtggggtgc ccgataggtt ctcaggcagc gggtccgaaa ccgactttac actgaaaatt   240
tctcgcgtgg aggctgaaga tgtcggaacc tactattgcg cacagtttct ggaatacccct   300
cacactttcg gggcaggcac taagctggag ctgaagcgt                          339
```

<210> SEQ ID NO 4
<211> LENGTH: 113
<212> TYPE: PRT
<213> ORGANISM: Artificial Sequence
<220> FEATURE:
<223> OTHER INFORMATION: Effi3 VLvar3_aa

<400> SEQUENCE: 4

```
Asp Ile Val Leu Thr Gln Ser Pro Ser Ser Leu Pro Val Thr Pro Gly
1               5                   10                  15
Glu Pro Ala Ser Ile Ser Cys Arg Ser Ser Gln Ser Leu Leu Thr Val
            20                  25                  30
Lys Gly Ile Thr Ser Leu Tyr Trp Phe Leu Gln Lys Pro Gly Gln Ser
        35                  40                  45
Pro Lys Leu Leu Ile Tyr Arg Met Ser Asn Arg Asp Ser Gly Val Pro
    50                  55                  60
Asp Arg Phe Ser Gly Ser Gly Ser Glu Thr Asp Phe Thr Leu Lys Ile
65                  70                  75                  80
Ser Arg Val Glu Ala Glu Asp Val Gly Thr Tyr Tyr Cys Ala Gln Phe
                85                  90                  95
Leu Glu Tyr Pro His Thr Phe Gly Ala Gly Thr Lys Leu Glu Leu Lys
            100                 105                 110
Arg
```

<210> SEQ ID NO 5
<211> LENGTH: 339
<212> TYPE: DNA
<213> ORGANISM: Artificial Sequence
<220> FEATURE:
<223> OTHER INFORMATION: Effi3-VLvar4

<400> SEQUENCE: 5

```
gacatcgtgc tgacacagag tccctcctcc ctgccagtga cacctggaga gccagcatct    60
atcagttgcc gaagctccca ggacctgctg actgtcaagg gcattacctc actgtactgg   120
ttcctgcaga agcccgggca gagccctaaa ctgctgatct atcggatgtc taacagagac   180
agtggagtgc ccgataggtt ctcaggcagc gggtccggaa ccgactttac actgaaaatt   240
tctcgcgtgg aggctgaaga tgtcggcacc tactattgcg cacagtttct ggagtatccc   300
cacacctttg agcaggcac taagctggag ctgaagcgt                           339
```

<210> SEQ ID NO 6
<211> LENGTH: 113
<212> TYPE: PRT

<213> ORGANISM: Artificial Sequence
<220> FEATURE:
<223> OTHER INFORMATION: Effi3-VLvar4_aa

<400> SEQUENCE: 6

```
Asp Ile Val Leu Thr Gln Ser Pro Ser Leu Pro Val Thr Pro Gly
1               5                  10                  15

Glu Pro Ala Ser Ile Ser Cys Arg Ser Ser Gln Asp Leu Leu Thr Val
            20                  25                  30

Lys Gly Ile Thr Ser Leu Tyr Trp Phe Leu Gln Lys Pro Gly Gln Ser
        35                  40                  45

Pro Lys Leu Leu Ile Tyr Arg Met Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Ala Gln Phe
                85                  90                  95

Leu Glu Tyr Pro His Thr Phe Gly Ala Gly Thr Lys Leu Glu Leu Lys
            100                 105                 110

Arg
```

<210> SEQ ID NO 7
<211> LENGTH: 423
<212> TYPE: DNA
<213> ORGANISM: Artificial Sequence
<220> FEATURE:
<223> OTHER INFORMATION: Effi3 VHvar3 (+signal peptide)

<400> SEQUENCE: 7

```
atgctggtcc tgcagtgggt cctggtcacc gctctgtttc aggggtcca ttgtgctgtg      60 cagctggtcg aatctggggg ggggctggtc cagcccggcg ggtctctgaa aatcacttgc    120
gccgctagtg ggttcacctt tacaaacgca gccatgtact gggtccgaca ggctcctgga    180
aagggcctgg agtgggtggc acggatcaga acaaaggcta caactacgc aacttactat     240 gccgactcag tgaagggcag gttcaccatt agccgcgacg atagcaaatc cacagtctac    300
ctgcagatgg actctgtgaa gacagaagat actgccacct actattgtat tgtggtcgtg    360
ctgactacta cacgggatta ctttgactat tggggacagg gagtgctggt gacagtgagt    420
tca                                                                  423
```

<210> SEQ ID NO 8
<211> LENGTH: 141
<212> TYPE: PRT
<213> ORGANISM: Artificial Sequence
<220> FEATURE:
<223> OTHER INFORMATION: Effi3 VHvar3_aa (+signal peptide)

<400> SEQUENCE: 8

```
Met Leu Val Leu Gln Trp Val Leu Val Thr Ala Leu Phe Gln Gly Val
1               5                  10                  15

His Cys Ala Val Gln Leu Val Glu Ser Gly Gly Gly Leu Val Gln Pro
            20                  25                  30

Gly Gly Ser Leu Lys Ile Thr Cys Ala Ala Ser Gly Phe Thr Phe Thr
        35                  40                  45

Asn Ala Ala Met Tyr Trp Val Arg Gln Ala Pro Gly Lys Gly Leu Glu
    50                  55                  60

Trp Val Ala Arg Ile Arg Thr Lys Ala Asn Asn Tyr Ala Thr Tyr Tyr
65                  70                  75                  80
```

Ala Asp Ser Val Lys Gly Arg Phe Thr Ile Ser Arg Asp Asp Ser Lys
         85                  90                  95

Ser Thr Val Tyr Leu Gln Met Asp Ser Val Lys Thr Glu Asp Thr Ala
            100                 105                 110

Thr Tyr Tyr Cys Ile Val Val Val Leu Thr Thr Arg Asp Tyr Phe
        115                 120                 125

Asp Tyr Trp Gly Gln Gly Val Leu Val Thr Val Ser Ser
    130                 135                 140

<210> SEQ ID NO 9
<211> LENGTH: 399
<212> TYPE: DNA
<213> ORGANISM: Artificial Sequence
<220> FEATURE:
<223> OTHER INFORMATION: Effi3 VLvar3 (+signal peptide)

<400> SEQUENCE: 9
atgaagtttc ctgctcagtt tctgggcctg attgtgctgt gtattcctgg cgctaccgga      60
gacatcgtcc tgactcagtc cccctcttcc ctgccagtga cacctggaga gccagcatct     120
atcagttgcc gaagctccca gtcactgctg actgtcaagg gaattaccag cctgtactgg     180
ttcctgcaga agcccggcca gtcccctaaa ctgctgatct atcggatgtc taacagagac     240
agtggggtgc ccgataggtt ctcaggcagc gggtccgaaa ccgactttac actgaaaatt     300
tctcgcgtgg aggctgaaga tgtcggaacc tactattgcg cacagtttct ggaataccct     360
cacactttcg gggcaggcac taagctggag ctgaagcgt                            399

<210> SEQ ID NO 10
<211> LENGTH: 133
<212> TYPE: PRT
<213> ORGANISM: Artificial Sequence
<220> FEATURE:
<223> OTHER INFORMATION: Effi3 VLvar3_aa (+signal peptide)

<400> SEQUENCE: 10

Met Lys Phe Pro Ala Gln Phe Leu Gly Leu Ile Val Leu Cys Ile Pro
1               5                   10                  15

Gly Ala Thr Gly Asp Ile Val Leu Thr Gln Ser Pro Ser Ser Leu Pro
            20                  25                  30

Val Thr Pro Gly Glu Pro Ala Ser Ile Ser Cys Arg Ser Ser Gln Ser
        35                  40                  45

Leu Leu Thr Val Lys Gly Ile Thr Ser Leu Tyr Trp Phe Leu Gln Lys
    50                  55                  60

Pro Gly Gln Ser Pro Lys Leu Leu Ile Tyr Arg Met Ser Asn Arg Asp
65                  70                  75                  80

Ser Gly Val Pro Asp Arg Phe Ser Gly Ser Gly Ser Glu Thr Asp Phe
            85                  90                  95

Thr Leu Lys Ile Ser Arg Val Glu Ala Glu Asp Val Gly Thr Tyr Tyr
        100                 105                 110

Cys Ala Gln Phe Leu Glu Tyr Pro His Thr Phe Gly Ala Gly Thr Lys
    115                 120                 125

Leu Glu Leu Lys Arg
    130

<210> SEQ ID NO 11
<211> LENGTH: 399
<212> TYPE: DNA
<213> ORGANISM: Artificial Sequence
<220> FEATURE:
<223> OTHER INFORMATION: Effi3-VLvar4 (+signal peptide)

<400> SEQUENCE: 11

```
atgaagttcc ctgctcagtt cctggggctg attgtcctgt gcattcctgg ggcaaccggc      60
gacatcgtgc tgacacagag tccctcctcc ctgccagtga cacctggaga gccagcatct     120
atcagttgcc gaagctccca ggacctgctg actgtcaagg gcattacctc actgtactgg     180
ttcctgcaga agcccgggca gagccctaaa ctgctgatct ccggatgtc taacagagac      240
agtggagtgc ccgataggtt ctcaggcagc gggtccggaa ccgactttac actgaaaatt     300
tctcgcgtgg aggctgaaga tgtcggcacc tactattgcg cacagtttct ggagtatccc     360
cacacctttg gagcaggcac taagctggag ctgaagcgt                            399
```

<210> SEQ ID NO 12
<211> LENGTH: 133
<212> TYPE: PRT
<213> ORGANISM: Artificial Sequence
<220> FEATURE:
<223> OTHER INFORMATION: Effi3-VLvar4_aa (+signal peptide)

<400> SEQUENCE: 12

```
Met Lys Phe Pro Ala Gln Phe Leu Gly Leu Ile Val Leu Cys Ile Pro
1               5                   10                  15
Gly Ala Thr Gly Asp Ile Val Leu Thr Gln Ser Pro Ser Ser Leu Pro
            20                  25                  30
Val Thr Pro Gly Glu Pro Ala Ser Ile Ser Cys Arg Ser Ser Gln Asp
        35                  40                  45
Leu Leu Thr Val Lys Gly Ile Thr Ser Leu Tyr Trp Phe Leu Gln Lys
    50                  55                  60
Pro Gly Gln Ser Pro Lys Leu Leu Ile Tyr Arg Met Ser Asn Arg Asp
65                  70                  75                  80
Ser Gly Val Pro Asp Arg Phe Ser Gly Ser Gly Ser Gly Thr Asp Phe
                85                  90                  95
Thr Leu Lys Ile Ser Arg Val Glu Ala Glu Asp Val Gly Thr Tyr Tyr
            100                 105                 110
Cys Ala Gln Phe Leu Glu Tyr Pro His Thr Phe Gly Ala Gly Thr Lys
        115                 120                 125
Leu Glu Leu Lys Arg
    130
```

<210> SEQ ID NO 13
<211> LENGTH: 27
<212> TYPE: DNA
<213> ORGANISM: Artificial Sequence
<220> FEATURE:
<223> OTHER INFORMATION: Effi3 VHvar3_CDR1

<400> SEQUENCE: 13

```
ttcacctttq caaacgcagc catgtac                                          27
```

<210> SEQ ID NO 14
<211> LENGTH: 9
<212> TYPE: PRT
<213> ORGANISM: Artificial Sequence
<220> FEATURE:
<223> OTHER INFORMATION: Effi3 VHvar3_CDR1-aa

<400> SEQUENCE: 14

```
Phe Thr Phe Thr Asn Ala Ala Met Tyr
```

<210> SEQ ID NO 15
<211> LENGTH: 57
<212> TYPE: DNA
<213> ORGANISM: Artificial Sequence
<220> FEATURE:
<223> OTHER INFORMATION: Effi3 VHvar3_CDR2

<400> SEQUENCE: 15
cggatcagaa caaaggctaa caactacgca acttactatg ccgactcagt gaagggc    57

<210> SEQ ID NO 16
<211> LENGTH: 19
<212> TYPE: PRT
<213> ORGANISM: Artificial Sequence
<220> FEATURE:
<223> OTHER INFORMATION: Effi3 VHvar3_CDR2-aa

<400> SEQUENCE: 16

Arg Ile Arg Thr Lys Ala Asn Asn Tyr Ala Thr Tyr Tyr Ala Asp Ser
1               5                   10                  15

Val Lys Gly

<210> SEQ ID NO 17
<211> LENGTH: 36
<212> TYPE: DNA
<213> ORGANISM: Artificial Sequence
<220> FEATURE:
<223> OTHER INFORMATION: Effi3 VHvar3_CDR3

<400> SEQUENCE: 17
gtcgtgctga ctactacacg ggattacttt gactat                            36

<210> SEQ ID NO 18
<211> LENGTH: 12
<212> TYPE: PRT
<213> ORGANISM: Artificial Sequence
<220> FEATURE:
<223> OTHER INFORMATION: Effi3 VHvar3_CDR3-aa

<400> SEQUENCE: 18

Val Val Leu Thr Thr Thr Arg Asp Tyr Phe Asp Tyr
1               5                   10

<210> SEQ ID NO 19
<211> LENGTH: 48
<212> TYPE: DNA
<213> ORGANISM: Artificial Sequence
<220> FEATURE:
<223> OTHER INFORMATION: Effi3 VLvar3_CDR1

<400> SEQUENCE: 19
cgaagctccc agtcactgct gactgtcaag ggaattacca gcctgtac               48

<210> SEQ ID NO 20
<211> LENGTH: 16
<212> TYPE: PRT
<213> ORGANISM: Artificial Sequence
<220> FEATURE:
<223> OTHER INFORMATION: Effi3 VLvar3-CDR1_aa

<400> SEQUENCE: 20

Arg Ser Ser Gln Ser Leu Leu Thr Val Lys Gly Ile Thr Ser Leu Tyr
1               5                   10                  15

<210> SEQ ID NO 21
<211> LENGTH: 21
<212> TYPE: DNA
<213> ORGANISM: Artificial Sequence
<220> FEATURE:
<223> OTHER INFORMATION: Effi3 VLvar3/4_CDR2

<400> SEQUENCE: 21
cggatgtcta acagagacag t        21

<210> SEQ ID NO 22
<211> LENGTH: 7
<212> TYPE: PRT
<213> ORGANISM: Artificial Sequence
<220> FEATURE:
<223> OTHER INFORMATION: Effi3 VLvar3/4_CDR2aa

<400> SEQUENCE: 22

Arg Met Ser Asn Arg Asp Ser
1               5

<210> SEQ ID NO 23
<211> LENGTH: 27
<212> TYPE: DNA
<213> ORGANISM: Artificial Sequence
<220> FEATURE:
<223> OTHER INFORMATION: Effi3 VLvar3/4_CDR3

<400> SEQUENCE: 23
gcacagtttc tggaataccc tcacact        27

<210> SEQ ID NO 24
<211> LENGTH: 9
<212> TYPE: PRT
<213> ORGANISM: Artificial Sequence
<220> FEATURE:
<223> OTHER INFORMATION: Effi3 VLvar3/4_CDR3aa

<400> SEQUENCE: 24

Ala Gln Phe Leu Glu Tyr Pro His Thr
1               5

<210> SEQ ID NO 25
<211> LENGTH: 48
<212> TYPE: DNA
<213> ORGANISM: Artificial Sequence
<220> FEATURE:
<223> OTHER INFORMATION: Effi3-VLvar4_CDR1

<400> SEQUENCE: 25
cgaagctccc aggacctgct gactgtcaag ggcattacct cactgtac        48

<210> SEQ ID NO 26
<211> LENGTH: 16
<212> TYPE: PRT
<213> ORGANISM: Artificial Sequence
<220> FEATURE:
<223> OTHER INFORMATION: Effi3-VLvar4_CDR1_aa

<400> SEQUENCE: 26

Arg Ser Ser Gln Asp Leu Leu Thr Val Lys Gly Ile Thr Ser Leu Tyr
1               5                   10                  15

<210> SEQ ID NO 27
<211> LENGTH: 993
<212> TYPE: DNA

<213> ORGANISM: Artificial Sequence
<220> FEATURE:
<223> OTHER INFORMATION: IgG1m (E333A)

<400> SEQUENCE: 27

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgcgaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                 993
```

<210> SEQ ID NO 28
<211> LENGTH: 330
<212> TYPE: PRT
<213> ORGANISM: Artificial Sequence
<220> FEATURE:
<223> OTHER INFORMATION: IgG1m (E333A)_aa

<400> SEQUENCE: 28

```
Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Ala Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 29
<211> LENGTH: 984
<212> TYPE: DNA
<213> ORGANISM: Artificial Sequence
<220> FEATURE:
<223> OTHER INFORMATION: IgG4m (S228P)

<400> SEQUENCE: 29
gctagcacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcacctgagt tcctgggggg accatcagtc     360
ttcctgttcc cccaaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctccgggtaa atga                                            984
```

-continued

```
<210> SEQ ID NO 30
<211> LENGTH: 327
<212> TYPE: PRT
<213> ORGANISM: Artificial Sequence
<220> FEATURE:
<223> OTHER INFORMATION: IgG4m (S228P)_aa

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 31
<211> LENGTH: 981
<212> TYPE: DNA
<213> ORGANISM: Artificial Sequence
<220> FEATURE:
<223> OTHER INFORMATION: IgG2b
```

<400> SEQUENCE: 31

```
gctagcacca agggcccatc ggtcttcccc ctggcgccct gctccaggag cacctccgag    60
agcacagcgg ccctgggctg cctggtcaag gactacttcc ccgaaccggt gacggtgtcg   120
tggaactcag gcgctctgac cagcggcgtg cacaccttcc cagctgtcct acagtcctca   180
ggactctact ccctcagcag cgtggtgacc gtgccctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggaccctga ggtcacgtgc    420
gtggtggtgg acgtgagcca cgaagacccc gaggtccagt tcaactggta cgtggacggc   480
gtggaggtgc ataatgccaa gacaaagcca cgggaggagc agttcaacag cacgttccgt   540
gtggtcagcg tcctcaccgt tgtgcaccag gactggctga acggcaagga gtacaagtgc   600
aaggtctcca acaaaggcct cccagccccc atcgagaaaa ccatctccaa aaccaaaggg   660
cagccccgag aaccacaggt gtacaccctg cccccatccc gggaggagat gaccaagaac   720
caggtcagcc tgacctgcct ggtcaaaggc ttctacccca gcgacatcgc cgtggagtgg   780
gagagcaatg ggcagccgga gaacaactac aagaccacgc tcccatgct ggactccgac    840
ggctccttct tcctctacag caagctcacc gtggacaaga gcaggtggca gcaggggaac   900
gtcttctcat gctccgtgat gcatgaggct ctgcacaacc actacacgca gaagagcctc   960
tccctgtctc cgggtaaatg a                                              981
```

<210> SEQ ID NO 32
<211> LENGTH: 326
<212> TYPE: PRT
<213> ORGANISM: Artificial Sequence
<220> FEATURE:
<223> OTHER INFORMATION: IgG2b_aa

<400> SEQUENCE: 32

```
Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 33
<211> LENGTH: 321
<212> TYPE: DNA
<213> ORGANISM: Artificial Sequence
<220> FEATURE:
<223> OTHER INFORMATION: CLkappa

<400> SEQUENCE: 33
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

<210> SEQ ID NO 34
<211> LENGTH: 106
<212> TYPE: PRT
<213> ORGANISM: Artificial Sequence
<220> FEATURE:
<223> OTHER INFORMATION: CLkappa_aa

<400> SEQUENCE: 34

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
```

```
                        85                  90                  95

Val Thr Lys Ser Phe Asn Arg Gly Glu Cys
            100                 105

<210> SEQ ID NO 35
<211> LENGTH: 321
<212> TYPE: DNA
<213> ORGANISM: Artificial Sequence
<220> FEATURE:
<223> OTHER INFORMATION: CLlambda

<400> SEQUENCE: 35
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac acctccaaa    180 caaagcaaca acaagtacgc ggccagcagc tatctgagcc tgacgcctga gcagtggaag   240
tcccacagaa gctacagctg ccaggtcacg catgaaggga gcaccgtgga agacagtgt   300 gcccctacag aatgttcata g                                             321

<210> SEQ ID NO 36
<211> LENGTH: 106
<212> TYPE: PRT
<213> ORGANISM: Artificial Sequence
<220> FEATURE:
<223> OTHER INFORMATION: CLlambda_aa

<400> SEQUENCE: 36

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 37
<211> LENGTH: 330
<212> TYPE: PRT
<213> ORGANISM: Artificial Sequence
<220> FEATURE:
<223> OTHER INFORMATION: HumanFc_IgG1(UniprotP01857)

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 38
<211> LENGTH: 327
<212> TYPE: PRT
<213> ORGANISM: Artificial Sequence
<220> FEATURE:
<223> OTHER INFORMATION: HumanFc_IgG4(UniprotP01861)

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 39
<211> LENGTH: 459
<212> TYPE: PRT
<213> ORGANISM: Artificial Sequence
<220> FEATURE:
<223> OTHER INFORMATION: human CD127 aa

<400> SEQUENCE: 39

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
            50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
            115                 120                 125
```

```
Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
                260                 265                 270

Trp Pro Ser Leu Pro Asp His Lys Lys Thr Leu Glu His Leu Cys Lys
            275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
                340                 345                 350

Asp Val Val Ile Thr Pro Glu Ser Phe Gly Arg Asp Ser Ser Leu Thr
            355                 360                 365

Cys Leu Ala Gly Asn Val Ser Ala Cys Asp Ala Pro Ile Leu Ser Ser
    370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
                420                 425                 430

Gln Gly Gln Pro Ile Leu Thr Ser Leu Gly Ser Asn Gln Glu Glu Ala
            435                 440                 445

Tyr Val Thr Met Ser Ser Phe Tyr Gln Asn Gln
    450                 455

<210> SEQ ID NO 40
<211> LENGTH: 219
<212> TYPE: PRT
<213> ORGANISM: Artificial Sequence
<220> FEATURE:
<223> OTHER INFORMATION: human CD127_21-239 aa

<400> SEQUENCE: 40

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
                20                  25                  30
```

His Ser Leu Thr Cys Ala Phe Glu Asp Pro Asp Val Asn Thr Thr Asn
            35                  40                  45

Leu Glu Phe Glu Ile Cys Gly Ala Leu Val Glu Val Lys Cys Leu Asn
 50                  55                  60

Phe Arg Lys Leu Gln Glu Ile Tyr Phe Ile Glu Thr Lys Lys Phe Leu
 65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
                100                 105                 110

Phe Asp Leu Ser Val Ile Tyr Arg Glu Gly Ala Asn Asp Phe Val Val
            115                 120                 125

Thr Phe Asn Thr Ser His Leu Gln Lys Lys Tyr Val Lys Val Leu Met
  130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
            195                 200                 205

Pro Glu Ile Asn Asn Ser Ser Gly Glu Met Asp
            210                 215

<210> SEQ ID NO 41
<211> LENGTH: 1416
<212> TYPE: DNA
<213> ORGANISM: Artificial Sequence
<220> FEATURE:
<223> OTHER INFORMATION: Effi3_VH3_IgG1m(E333A)

<400> SEQUENCE: 41

```
atgctggtcc tgcagtgggt cctggtcacc gctctgtttc aggggggtcca ttgtgctgtg      60 cagctggtcg aatctggggg ggggctggtc agcccggcg ggtctctgaa aatcacttgc      120
gccgctagtg ggttcacctt tacaaacgca gccatgtact gggtccgaca ggctcctgga      180
aagggcctgg agtgggtggc acggatcaga acaaaggcta caactacgc aacttactat      240 gccgactcag tgaagggcag gttcaccatt agccgcgacg atagcaaatc cacagtctac      300
ctgcagatgg actctgtgaa gacagaagat actgccacct actattgtat tgtggtcgtg      360
ctgactacta cacgggatta ctttgactat tggggacagg gagtgctggt gacagtgagt      420
tcagctagca ccaagggccc atcggtcttc cccctggcac cctcctccaa gagcacctct      480
gggggcacag cggccctggg ctgcctggtc aaggactact ccccgaacc ggtgacggtg      540 tcgtggaact caggcgccct gaccagcggc gtgcacacct tcccggctgt cctacagtcc      600
tcaggactct actccctcag cagcgtggtg accgtgccct ccagcagctt gggcacccag      660
acctacatct gcaacgtgaa tcacaagccc agcaacacca aggtggacaa gaaagttgag      720
cccaaatctt gtgacaaaac tcacacatgc ccaccgtgcc cagcacctga actcctgggg      780
ggaccgtcag tcttcctctt cccccaaaa cccaaggaca cctcatgat ctcccggacc      840 cctgaggtca catgcgtggt ggtggacgtg agccacgaag accctgaggt caagttcaac      900
tggtacgtgg acggcgtgga ggtgcataat gccaagacaa agccgcggga ggagcagtac      960
```

```
aacagcacgt accgtgtggt cagcgtcctc accgtcctgc accaggactg gctgaatggc   1020
aaggagtaca agtgcaaggt ctccaacaaa gccctcccag ccccatcgc gaaaaccatc    1080 tccaaagcca agggcagcc ccgagaacca caggtgtaca ccctgccccc atcccgggag    1140
gagatgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaatga                             1416
```

<210> SEQ ID NO 42
<211> LENGTH: 471
<212> TYPE: PRT
<213> ORGANISM: Artificial Sequence
<220> FEATURE:
<223> OTHER INFORMATION: Effi3_VH3_IgG1m(E333A)_aa

<400> SEQUENCE: 42

```
Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Gly Gly Ser Leu Lys Ile Thr Cys Ala Ala Ser Gly Phe Thr Phe Thr
        35                  40                  45

Asn Ala Ala Met Tyr Trp Val Arg Gln Ala Pro Gly Lys Gly Leu Glu
    50                  55                  60

Trp Val Ala Arg Ile Arg Thr Lys Ala Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Thr Val Tyr Leu Gln Met Asp Ser Val Lys Thr Glu Asp Thr Ala
            100                 105                 110

Thr Tyr Tyr Cys Ile Val Val Leu Thr Thr Thr Arg Asp Tyr Phe
        115                 120                 125

Asp Tyr Trp Gly Gln Gly Val Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285
```

```
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Ala Lys Thr Ile Ser Lys Ala Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 43
<211> LENGTH: 1407
<212> TYPE: DNA
<213> ORGANISM: Artificial Sequence
<220> FEATURE:
<223> OTHER INFORMATION: Effi3_VH3_IgG4(S228P)

<400> SEQUENCE: 43
atgctggtcc tgcagtgggt cctggtcacc gctctgtttc aggggtccca ttgtgctgtg      60
cagctggtcg aatctggggg ggggctggtc agcccggcg  ggtctctgaa aatcacttgc     120
gccgctagtg gcttcacctt tacaaacgca gccatgtact gggtccgaca ggctcctgga     180
aagggcctgg agtgggtggc acggatcaga acaaaggcta caactacgc  aacttactat     240 gccgactcag tgaagggcag gttcaccatt agccgcgacg atagcaaatc cacagtctac     300
ctgcagatgg actctgtgaa gacagaagat actgccacct actattgtat tgtggtcgtg     360
ctgactacta cacgggatta ctttgactat tggggacagg gagtgctggt gacagtgagt     420
tcagctagca ccaagggccc atcggtcttc cccctggcgc cctgctccag gagcacctcc     480
gagagcacag ccgccctggg ctgcctggtc aaggactact ccccgaaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacgaag     660
acctacacct gcaacgtaga tcacaagccc agcaacacca aggtggacaa gagagttgag     720
tccaaatatg gtcccccatg cccaccatgc ccagcacctg agttcctggg gggaccatca     780
gtcttcctgt tccccccaaa acccaaggac actctcatga tctcccggac ccctgaggtc     840
acgtgcgtgg tggtggacgt gagccaggaa gaccccgagg tccagttcaa ctggtacgtg     900
gatggcgtgg aggtgcataa tgccaagaca aagccgcggg aggagcagtt caacagcacg     960
```

```
taccgtgtgg tcagcgtcct caccgtcctg caccaggact ggctgaacgg caaggagtac   1020
aagtgcaagg tctccaacaa aggcctcccg tcctccatcg agaaaaccat ctccaaagcc   1080
aaagggcagc cccgagagcc acaggtgtac accctgcccc catcccagga ggagatgacc   1140
aagaaccagg tcagcctgac ctgcctggtc aaaggcttct accccagcga catcgccgtg   1200
gagtgggaga gcaatgggca gccggagaac aactacaaga ccacgcctcc cgtgctggac   1260
tccgacggct ccttcttcct ctacagcagg ctaaccgtgg acaagagcag gtggcaggag   1320
gggaatgtct tctcatgctc cgtgatgcat gaggctctgc acaaccacta cacacagaag   1380
agcctctccc tgtctccggg taaatga                                       1407
```

<210> SEQ ID NO 44
<211> LENGTH: 468
<212> TYPE: PRT
<213> ORGANISM: Artificial Sequence
<220> FEATURE:
<223> OTHER INFORMATION: Effi3_VH3_IgG4(S228P)_aa

<400> SEQUENCE: 44

```
Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Gly Gly Ser Leu Lys Ile Thr Cys Ala Ala Ser Gly Phe Thr Phe Thr
        35                  40                  45

Asn Ala Ala Met Tyr Trp Val Arg Gln Ala Pro Gly Lys Gly Leu Glu
    50                  55                  60

Trp Val Ala Arg Ile Arg Thr Lys Ala Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Thr Val Tyr Leu Gln Met Asp Ser Val Lys Thr Glu Asp Thr Ala
            100                 105                 110

Thr Tyr Tyr Cys Ile Val Val Leu Thr Thr Thr Arg Asp Tyr Phe
        115                 120                 125

Asp Tyr Trp Gly Gln Gly Val Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

Gln Glu Asp Pro Glu Val Gln Phe Asn Trp Tyr Val Asp Gly Val Glu
        290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 45
<211> LENGTH: 1404
<212> TYPE: DNA
<213> ORGANISM: Artificial Sequence
<220> FEATURE:
<223> OTHER INFORMATION: Effi3_VH3_IgG2b

<400> SEQUENCE: 45
atgctggtcc tgcagtgggt cctggtcacc gctctgtttc aggggtccca ttgtgctgtg      60
cagctggtcg aatctggggg ggggctggtc cagcccggcg ggtctctgaa aatcacttgc     120
gccgctagtg ggttcacctt tacaaacgca gccatgtact gggtccgaca ggctcctgga     180
aagggcctgg agtgggtggc acggatcaga acaaaggcta caactacgc aacttactat     240 gccgactcag tgaagggcag gttcaccatt agccgcgacg atagcaaatc cacagtctac     300
ctgcagatgg actctgtgaa gacagaagat actgccacct actattgtat tgtggtcgtg     360
ctgactacta cacgggatta ctttgactat tggggacagg gagtgctggt gacagtgagt     420
tcagctagca ccaagggccc atcggtcttc cccctggcgc cctgctccag gagcacctcc     480
gagagcacag cggccctggg ctgcctggtc aaggactact ccccgaaccc ggtgacggtg     540
tcgtggaact caggcgctct gaccagcggc gtgcacacct tcccagctgt cctacagtcc     600
tcaggactct actccctcag cagcgtggtg accgtgccct ccagcaactt cggcacccag     660
acctacacct gcaacgtaga tcacaagccc agcaacacca aggtggacaa gacagttgag     720
cgcaaatgtt gtgtcgagtg cccaccgtgc ccagcaccac ctgtggcagg accgtcagtc     780
ttcctcttcc ccccaaaacc caaggacacc ctcatgatct cccggacccc tgaggtcacg     840
tgcgtggtgg tggacgtgag ccacgaagac cccgaggtcc agttcaactg gtacgtggac     900
ggcgtggagg tgcataatgc caagacaaag ccacgggagg agcagttcaa cagcacgttc     960

```
cgtgtggtca gcgtcctcac cgttgtgcac caggactggc tgaacggcaa ggagtacaag    1020
tgcaaggtct ccaacaaagg cctcccagcc cccatcgaga aaaccatctc caaaaccaaa    1080
gggcagcccc gagaaccaca ggtgtacacc ctgcccccat cccgggagga gatgaccaag    1140
aaccaggtca gcctgacctg cctggtcaaa ggcttctacc ccagcgacat cgccgtggag    1200
tgggagagca atgggcagcc ggagaacaac tacaagacca cgcctcccat gctggactcc    1260
gacggctcct tcttcctcta cagcaagctc accgtggaca gagcaggtg gcagcagggg    1320 aacgtcttct catgctccgt gatgcatgag gctctgcaca accactacac gcagaagagc    1380
ctctccctgt ctccgggtaa atga                                          1404
```

<210> SEQ ID NO 46
<211> LENGTH: 467
<212> TYPE: PRT
<213> ORGANISM: Artificial Sequence
<220> FEATURE:
<223> OTHER INFORMATION: Effi3_VH3_IgG2b_aa

<400> SEQUENCE: 46

```
Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Gly Gly Ser Leu Lys Ile Thr Cys Ala Ala Ser Gly Phe Thr Phe Thr
        35                  40                  45

Asn Ala Ala Met Tyr Trp Val Arg Gln Ala Pro Gly Lys Gly Leu Glu
    50                  55                  60

Trp Val Ala Arg Ile Arg Thr Lys Ala Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Thr Val Tyr Leu Gln Met Asp Ser Val Lys Thr Glu Asp Thr Ala
            100                 105                 110

Thr Tyr Tyr Cys Ile Val Val Leu Thr Thr Arg Asp Tyr Phe
        115                 120                 125

Asp Tyr Trp Gly Gln Gly Val Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Gln Phe Asn Trp Tyr Val Asp Gly Val Glu Val
    290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 47
<211> LENGTH: 720
<212> TYPE: DNA
<213> ORGANISM: Artificial Sequence
<220> FEATURE:
<223> OTHER INFORMATION: Effi3_VL4_CLkappa

<400> SEQUENCE: 47
atgaagttcc ctgctcagtt cctggggctg attgtcctgt gcattcctgg ggcaaccggc      60
gacatcgtgc tgacacagag tccctcctcc ctgccagtga cacctggaga gccagcatct    120
atcagttgcc gaagctccca ggacctgctg actgtcaagg cattacctc actgtactgg     180
ttcctgcaga agcccgggca gagccctaaa ctgctgatct atcggatgtc taacagagac    240
agtggagtgc ccgataggtt ctcaggcagc gggtccggaa ccgactttac actgaaaatt    300
tctcgcgtgg aggctgaaga tgtcggcacc tactattgcg cacagtttct ggagtatccc    360
cacaccttg agcaggcac taagctggag ctgaagcgta cggtggctgc accatctgtc     420
ttcatcttcc cgccatctga tgagcagttg aaatctggaa ctgcctctgt tgtgtgcctg    480
ctgaataact ctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720

<210> SEQ ID NO 48
<211> LENGTH: 239
<212> TYPE: PRT
<213> ORGANISM: Artificial Sequence
<220> FEATURE:
<223> OTHER INFORMATION: Effi3_VL4_CLkappa_aa
```

<400> SEQUENCE: 48

```
Met Lys Phe Pro Ala Gln Phe Leu Gly Leu Ile Val Leu Cys Ile Pro
1               5                   10                  15
Gly Ala Thr Gly Asp Ile Val Leu Thr Gln Ser Pro Ser Ser Leu Pro
            20                  25                  30
Val Thr Pro Gly Glu Pro Ala Ser Ile Ser Cys Arg Ser Ser Gln Asp
        35                  40                  45
Leu Leu Thr Val Lys Gly Ile Thr Ser Leu Tyr Trp Phe Leu Gln Lys
    50                  55                  60
Pro Gly Gln Ser Pro Lys Leu Leu Ile Tyr Arg Met Ser Asn Arg Asp
65                  70                  75                  80
Ser Gly Val Pro Asp Arg Phe Ser Gly Ser Gly Ser Gly Thr Asp Phe
                85                  90                  95
Thr Leu Lys Ile Ser Arg Val Glu Ala Glu Asp Val Gly Thr Tyr Tyr
            100                 105                 110
Cys Ala Gln Phe Leu Glu Tyr Pro His Thr Phe Gly Ala Gly Thr Lys
        115                 120                 125
Leu Glu Leu Lys Arg Thr Val Ala Ala Pro Ser Val Phe Ile Phe Pro
    130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
        195                 200                 205
Ala Asp Tyr Glu Lys His Lys Val Tyr Ala Cys Glu Val Thr His Gln
    210                 215                 220
Gly Leu Ser Ser Pro Val Thr Lys Ser Phe Asn Arg Gly Glu Cys
225                 230                 235
```

<210> SEQ ID NO 49
<211> LENGTH: 720
<212> TYPE: DNA
<213> ORGANISM: Artificial Sequence
<220> FEATURE:
<223> OTHER INFORMATION: Effi3_VL3_Clkappa

<400> SEQUENCE: 49

```
atgaagtttc ctgctcagtt tctgggcctg attgtgctgt gtattcctgg cgctaccgga    60
gacatcgtcc tgactcagtc cccctcttcc ctgccagtga cacctggaga gccagcatct   120
atcagttgcc gaagctccca gtcactgctg actgtcaagg gaattaccag cctgtactgg   180
ttcctgcaga agcccggcca gtcccctaaa ctgctgatct atcggatgtc aacagagac    240
agtggggtgc ccgataggtt ctcaggcagc gggtccgaaa ccgactttac actgaaaatt   300
tctcgcgtgg aggctgaaga tgtcggaacc tactattgcg cacagtttct ggaataccct   360
cacactttcg gggcaggcac taagctggag ctgaagcgta cggtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
```

```
gtcacccatc agggcctgag ctcgcccgtc acaaagagct tcaacagggg agagtgttag      720
```

<210> SEQ ID NO 50
<211> LENGTH: 239
<212> TYPE: PRT
<213> ORGANISM: Artificial Sequence
<220> FEATURE:
<223> OTHER INFORMATION: Effi3_VL3_CLkappa_aa

<400> SEQUENCE: 50

```
Met Lys Phe Pro Ala Gln Phe Leu Gly Leu Ile Val Leu Cys Ile Pro
1               5                   10                  15

Gly Ala Thr Gly Asp Ile Val Leu Thr Gln Ser Pro Ser Ser Leu Pro
            20                  25                  30

Val Thr Pro Gly Glu Pro Ala Ser Ile Ser Cys Arg Ser Ser Gln Ser
        35                  40                  45

Leu Leu Thr Val Lys Gly Ile Thr Ser Leu Tyr Trp Phe Leu Gln Lys
    50                  55                  60

Pro Gly Gln Ser Pro Lys Leu Leu Ile Tyr Arg Met Ser Asn Arg Asp
65                  70                  75                  80

Ser Gly Val Pro Asp Arg Phe Ser Gly Ser Gly Ser Glu Thr Asp Phe
                85                  90                  95

Thr Leu Lys Ile Ser Arg Val Glu Ala Glu Asp Val Gly Thr Tyr Tyr
            100                 105                 110

Cys Ala Gln Phe Leu Glu Tyr Pro His Thr Phe Gly Ala Gly Thr Lys
        115                 120                 125

Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 51
<211> LENGTH: 720
<212> TYPE: DNA
<213> ORGANISM: Artificial Sequence
<220> FEATURE:
<223> OTHER INFORMATION: Effi3_VL4_Cllambda

<400> SEQUENCE: 51

```
atgaagttcc ctgctcagtt cctggggctg attgtcctgt gcattcctgg ggcaaccggc       60
gacatcgtgc tgacacagag tccctcctcc ctgccagtga cacctggaga gccagcatct      120
atcagttgcc gaagctccca ggacctgctg actgtcaagg gcattacctc actgtactgg      180
ttcctgcaga gcccgggca gagccctaaa ctgctgatct atcggatgtc taacagagac      240
agtggagtgc cgataggtt ctcaggcagc gggtccggaa ccgactttac actgaaaatt      300
tctcgcgtgg aggctgaaga tgtcggcacc tactattgcg cacagttttct ggagtatccc      360
```

```
cacaccttg gagcaggcac taagctggag ctgaagcgtg gtcagcccaa ggctgccccc      420
tcggtcactc tgttcccgcc ctcctctgag gagcttcaag ccaacaaggc cacactggtg      480
tgtctcataa gtgacttcta cccgggagcc gtgacagtgg cctggaaggc agatagcagc      540
cccgtcaagg cgggagtgga gaccaccaca ccctccaaac aaagcaacaa caagtacgcg      600
gccagcagct atctgagcct gacgcctgag cagtggaagt cccacagaag ctacagctgc      660
caggtcacgc atgaagggag caccgtggag aagacagtgg cccctacaga atgttcatag      720
```

```
<210> SEQ ID NO 52
<211> LENGTH: 239
<212> TYPE: PRT
<213> ORGANISM: Artificial Sequence
<220> FEATURE:
<223> OTHER INFORMATION: Effi3_VL4_CLlambda_aa

<400> SEQUENCE: 52

Met Lys Phe Pro Ala Gln Phe Leu Gly Leu Ile Val Leu Cys Ile Pro
  1               5                  10                  15

Gly Ala Thr Gly Asp Ile Val Leu Thr Gln Ser Pro Ser Ser Leu Pro
             20                  25                  30

Val Thr Pro Gly Glu Pro Ala Ser Ile Ser Cys Arg Ser Ser Gln Asp
         35                  40                  45

Leu Leu Thr Val Lys Gly Ile Thr Ser Leu Tyr Trp Phe Leu Gln Lys
     50                  55                  60

Pro Gly Gln Ser Pro Lys Leu Leu Ile Tyr Arg Met Ser Asn Arg Asp
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Thr Tyr Tyr
            100                 105                 110

Cys Ala Gln Phe Leu Glu Tyr Pro His Thr Phe Gly Ala Gly Thr Lys
        115                 120                 125

Leu Glu Leu Lys Arg Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Gln Val Thr His
    210                 215                 220

Glu Gly Ser Thr Val Glu Lys Thr Val Ala Pro Thr Glu Cys Ser
225                 230                 235
```

```
<210> SEQ ID NO 53
<211> LENGTH: 720
<212> TYPE: DNA
<213> ORGANISM: Artificial Sequence
<220> FEATURE:
<223> OTHER INFORMATION: Effi3_VL3_CLlambda

<400> SEQUENCE: 53
atgaagtttc ctgctcagtt tctgggcctg attgtgctgt gtattcctgg cgctaccgga       60
```

```
gacatcgtcc tgactcagtc ccctcttcc ctgccagtga cacctggaga gccagcatct    120
atcagttgcc gaagctccca gtcactgctg actgtcaagg gaattaccag cctgtactgg    180
ttcctgcaga agcccggcca gtcccctaaa ctgctgatct atcggatgtc taacagagac    240
agtggggtgc ccgataggtt ctcaggcagc gggtccgaaa ccgactttac actgaaaatt    300
tctcgcgtgg aggctgaaga tgtcggaacc tactattgcg cacagtttct ggaataccct    360
cacactttcg gggcaggcac taagctggag ctgaagcgtg gtcagcccaa ggctgccccc    420
tcggtcactc tgttcccgcc ctcctctgag gagcttcaag ccaacaaggc cacactggtg    480
tgtctcataa gtgacttcta cccgggagcc gtgacagtgg cctggaaggc agatagcagc    540
cccgtcaagg cgggagtgga gaccaccaca ccctccaaac aaagcaacaa caagtacgcg    600
gccagcagct atctgagcct gacgcctgag cagtggaagt cccacagaag ctacagctgc    660
caggtcacgc atgaagggag caccgtggag aagacagtgg cccctacaga atgttcatag    720
```

<210> SEQ ID NO 54
<211> LENGTH: 239
<212> TYPE: PRT
<213> ORGANISM: Artificial Sequence
<220> FEATURE:
<223> OTHER INFORMATION: Effi3_VL3_CLlambda_aa
<400> SEQUENCE: 54

```
Met Lys Phe Pro Ala Gln Phe Leu Gly Leu Ile Val Leu Cys Ile Pro
1               5                   10                  15

Gly Ala Thr Gly Asp Ile Val Leu Thr Gln Ser Pro Ser Ser Leu Pro
            20                  25                  30

Val Thr Pro Gly Glu Pro Ala Ser Ile Ser Cys Arg Ser Ser Gln Ser
        35                  40                  45

Leu Leu Thr Val Lys Gly Ile Thr Ser Leu Tyr Trp Phe Leu Gln Lys
    50                  55                  60

Pro Gly Gln Ser Pro Lys Leu Leu Ile Tyr Arg Met Ser Asn Arg Asp
65                  70                  75                  80

Ser Gly Val Pro Asp Arg Phe Ser Gly Ser Gly Ser Glu Thr Asp Phe
                85                  90                  95

Thr Leu Lys Ile Ser Arg Val Glu Ala Glu Asp Val Gly Thr Tyr Tyr
            100                 105                 110

Cys Ala Gln Phe Leu Glu Tyr Pro His Thr Phe Gly Ala Gly Thr Lys
        115                 120                 125

Leu Glu Leu Lys Arg Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Gln Val Thr His
    210                 215                 220

Glu Gly Ser Thr Val Glu Lys Thr Val Ala Pro Thr Glu Cys Ser
225                 230                 235
```

<210> SEQ ID NO 55

```
<211> LENGTH: 27
<212> TYPE: PRT
<213> ORGANISM: Artificial Sequence
<220> FEATURE:
<223> OTHER INFORMATION: CD127 peptide

<400> SEQUENCE: 55

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu
            20                  25

<210> SEQ ID NO 56
<211> LENGTH: 123
<212> TYPE: PRT
<213> ORGANISM: Artificial Sequence
<220> FEATURE:
<223> OTHER INFORMATION: MD707-3 VH

<400> SEQUENCE: 56

Ala Val His Leu Val Glu Ser Gly Gly Gly Leu Val Gln Pro Lys Glu
1               5                   10                  15

Ser Leu Lys Ile Ser Cys Ala Ala Ser Gly Phe Thr Phe Ser Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Ala Asn Asn Tyr Ala Thr Tyr Tyr Ala Glu
    50                  55                  60

Ser Val Lys Gly Arg Phe Thr Ile Ser Arg Asp Asp Ser Lys Ser Met
65                  70                  75                  80

Val Tyr Leu Gln Met Asp Asn Val Lys Thr Asp Thr Ala Met Tyr
                85                  90                  95

Tyr Cys Ile Val Val Val Leu Thr Thr Thr Arg Asp Tyr Phe Asp Tyr
            100                 105                 110

Trp Gly Gln Gly Val Met Val Thr Val Ser Ser
        115                 120

<210> SEQ ID NO 57
<211> LENGTH: 113
<212> TYPE: PRT
<213> ORGANISM: Artificial Sequence
<220> FEATURE:
<223> OTHER INFORMATION: MD707-3 VL

<400> SEQUENCE: 57

Asp Ile Val Leu Thr Gln Ala Pro Leu Ser Val Ser Val Thr Pro Gly
1               5                   10                  15

Glu Ser Ala Ser Ile Ser Cys Arg Ser Ser Gln Ser Leu Leu Thr Val
            20                  25                  30

Lys Gly Ile Thr Ser Leu Tyr Trp Phe Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Arg Gly Ser Gly Ser Glu Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro His Thr Phe Gly Ala Gly Thr Lys Leu Glu Leu Lys
            100                 105                 110
```

Arg

```
<210> SEQ ID NO 58
<211> LENGTH: 15
<212> TYPE: PRT
<213> ORGANISM: Artificial Sequence
<220> FEATURE:
<223> OTHER INFORMATION: PEPT1

<400> SEQUENCE: 58

Glu Ser Gly Tyr Ala Gln Asn Gly Asp Leu Glu Asp Ala Glu Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: PEPT2

<400> SEQUENCE: 59

Ala Gln Asn Gly Asp Leu Glu Asp Ala Glu Leu Asp Asp Tyr Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: PEPT3

<400> SEQUENCE: 60

Asp Leu Glu Asp Ala Glu Leu Asp Asp Tyr Ser Phe Ser Cys Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: PEPT4

<400> SEQUENCE: 61

Ala Glu Leu Asp Asp Tyr Ser Phe Ser Cys Tyr Ser Gln Leu Glu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: PEPT5

<400> SEQUENCE: 62

Asp Tyr Ser Phe Ser Cys Tyr Ser Gln Leu Glu Val Asn Gly Ser
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: PEPT6

<400> SEQUENCE: 63

Ser Cys Tyr Ser Gln Leu Glu Val Asn Gly Ser Gln His Ser Leu
1               5                   10                  15
```

<210> SEQ ID NO 64
<211> LENGTH: 15
<212> TYPE: PRT
<213> ORGANISM: Artificial Sequence
<220> FEATURE:
<223> OTHER INFORMATION: PEPT7

<400> SEQUENCE: 64

Gln Leu Glu Val Asn Gly Ser Gln His Ser Leu Thr Cys Ala Phe
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: PEPT8

<400> SEQUENCE: 65

Asn Gly Ser Gln His Ser Leu Thr Cys Ala Phe Glu Asp Pro Asp
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: PEPT9

<400> SEQUENCE: 66

His Ser Leu Thr Cys Ala Phe Glu Asp Pro Asp Val Asn Thr Thr
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: PEPT10

<400> SEQUENCE: 67

Cys Ala Phe Glu Asp Pro Asp Val Asn Thr Thr Asn Leu Glu Phe
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: PEPT11

<400> SEQUENCE: 68

Asp Pro Asp Val Asn Thr Thr Asn Leu Glu Phe Glu Ile Cys Gly
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: PEPT12

<400> SEQUENCE: 69

Asn Thr Thr Asn Leu Glu Phe Glu Ile Cys Gly Ala Leu Val Glu
1               5                   10                  15

```
<210> SEQ ID NO 70
<211> LENGTH: 15
<212> TYPE: PRT
<213> ORGANISM: Artificial Sequence
<220> FEATURE:
<223> OTHER INFORMATION: PEPT13

<400> SEQUENCE: 70

Leu Glu Phe Glu Ile Cys Gly Ala Leu Val Glu Val Lys Cys Leu
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: PEPT14

<400> SEQUENCE: 71

Ile Cys Gly Ala Leu Val Glu Val Lys Cys Leu Asn Phe Arg Lys
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: PEPT15

<400> SEQUENCE: 72

Leu Val Glu Val Lys Cys Leu Asn Phe Arg Lys Leu Gln Glu Ile
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: PEPT16

<400> SEQUENCE: 73

Lys Cys Leu Asn Phe Arg Lys Leu Gln Glu Ile Tyr Phe Ile Glu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: PEPT17

<400> SEQUENCE: 74

Phe Arg Lys Leu Gln Glu Ile Tyr Phe Ile Glu Thr Lys Lys Phe
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: PEPT18

<400> SEQUENCE: 75

Gln Glu Ile Tyr Phe Ile Glu Thr Lys Lys Phe Leu Leu Ile Gly
1               5                   10                  15
```

-continued

```
<210> SEQ ID NO 76
<211> LENGTH: 15
<212> TYPE: PRT
<213> ORGANISM: Artificial Sequence
<220> FEATURE:
<223> OTHER INFORMATION: PEPT19

<400> SEQUENCE: 76

Phe Ile Glu Thr Lys Lys Phe Leu Leu Ile Gly Lys Ser Asn Ile
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: PEPT20

<400> SEQUENCE: 77

Lys Lys Phe Leu Leu Ile Gly Lys Ser Asn Ile Cys Val Lys Val
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: PEPT21

<400> SEQUENCE: 78

Leu Ile Gly Lys Ser Asn Ile Cys Val Lys Val Gly Glu Lys Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: PEPT22

<400> SEQUENCE: 79

Ser Asn Ile Cys Val Lys Val Gly Glu Lys Ser Leu Thr Cys Lys
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: PEPT23

<400> SEQUENCE: 80

Val Lys Val Gly Glu Lys Ser Leu Thr Cys Lys Lys Ile Asp Leu
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: PEPT24

<400> SEQUENCE: 81

Glu Lys Ser Leu Thr Cys Lys Lys Ile Asp Leu Thr Thr Ile Val
1               5                   10                  15

<210> SEQ ID NO 82
```

-continued

```
<211> LENGTH: 15
<212> TYPE: PRT
<213> ORGANISM: Artificial Sequence
<220> FEATURE:
<223> OTHER INFORMATION: PEPT25

<400> SEQUENCE: 82

Thr Cys Lys Lys Ile Asp Leu Thr Thr Ile Val Lys Pro Glu Ala
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: PEPT26

<400> SEQUENCE: 83

Ile Asp Leu Thr Thr Ile Val Lys Pro Glu Ala Pro Phe Asp Leu
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: PEPT27

<400> SEQUENCE: 84

Thr Ile Val Lys Pro Glu Ala Pro Phe Asp Leu Ser Val Ile Tyr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: PEPT28

<400> SEQUENCE: 85

Pro Glu Ala Pro Phe Asp Leu Ser Val Ile Tyr Arg Glu Gly Ala
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: PEPT29

<400> SEQUENCE: 86

Phe Asp Leu Ser Val Ile Tyr Arg Glu Gly Ala Asn Asp Phe Val
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: PEPT30

<400> SEQUENCE: 87

Val Ile Tyr Arg Glu Gly Ala Asn Asp Phe Val Val Thr Phe Asn
1               5                   10                  15

<210> SEQ ID NO 88
<211> LENGTH: 15
```

-continued

```
<210> SEQ ID NO 89
<211> LENGTH: 15
<212> TYPE: PRT
<213> ORGANISM: Artificial Sequence
<220> FEATURE:
<223> OTHER INFORMATION: PEPT31

<400> SEQUENCE: 88

Glu Gly Ala Asn Asp Phe Val Val Thr Phe Asn Thr Ser His Leu
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: PEPT32

<400> SEQUENCE: 89

Asp Phe Val Val Thr Phe Asn Thr Ser His Leu Gln Lys Lys Tyr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: PEPT33

<400> SEQUENCE: 90

Thr Phe Asn Thr Ser His Leu Gln Lys Lys Tyr Val Lys Val Leu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: PEPT34

<400> SEQUENCE: 91

Ser His Leu Gln Lys Lys Tyr Val Lys Val Leu Met His Asp Val
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: PEPT35

<400> SEQUENCE: 92

Lys Lys Tyr Val Lys Val Leu Met His Asp Val Ala Tyr Arg Gln
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: PEPT36

<400> SEQUENCE: 93

Lys Val Leu Met His Asp Val Ala Tyr Arg Gln Glu Lys Asp Glu
1               5                   10                  15

<210> SEQ ID NO 94
<211> LENGTH: 15
<212> TYPE: PRT
```

```
<213> ORGANISM: Artificial Sequence
<220> FEATURE:
<223> OTHER INFORMATION: PEPT37

<400> SEQUENCE: 94

His Asp Val Ala Tyr Arg Gln Glu Lys Asp Glu Asn Lys Trp Thr
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: PEPT38

<400> SEQUENCE: 95

Tyr Arg Gln Glu Lys Asp Glu Asn Lys Trp Thr His Val Asn Leu
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: PEPT39

<400> SEQUENCE: 96

Lys Asp Glu Asn Lys Trp Thr His Val Asn Leu Ser Ser Thr Lys
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: PEPT40

<400> SEQUENCE: 97

Lys Trp Thr His Val Asn Leu Ser Ser Thr Lys Leu Thr Leu Leu
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: PEPT41

<400> SEQUENCE: 98

Val Asn Leu Ser Ser Thr Lys Leu Thr Leu Leu Gln Arg Lys Leu
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: PEPT42

<400> SEQUENCE: 99

Ser Thr Lys Leu Thr Leu Leu Gln Arg Lys Leu Gln Pro Ala Ala
1               5                   10                  15

<210> SEQ ID NO 100
<211> LENGTH: 15
<212> TYPE: PRT
<213> ORGANISM: Artificial Sequence
```

```
<220> FEATURE:
<223> OTHER INFORMATION: PEPT43

<400> SEQUENCE: 100

Thr Leu Leu Gln Arg Lys Leu Gln Pro Ala Ala Met Tyr Glu Ile
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: PEPT44

<400> SEQUENCE: 101

Arg Lys Leu Gln Pro Ala Ala Met Tyr Glu Ile Lys Val Arg Ser
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: PEPT45

<400> SEQUENCE: 102

Pro Ala Ala Met Tyr Glu Ile Lys Val Arg Ser Ile Pro Asp His
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: PEPT46

<400> SEQUENCE: 103

Tyr Glu Ile Lys Val Arg Ser Ile Pro Asp His Tyr Phe Lys Gly
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: PEPT47

<400> SEQUENCE: 104

Val Arg Ser Ile Pro Asp His Tyr Phe Lys Gly Phe Trp Ser Glu
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: PEPT48

<400> SEQUENCE: 105

Pro Asp His Tyr Phe Lys Gly Phe Trp Ser Glu Trp Ser Pro Ser
1               5                   10                  15

<210> SEQ ID NO 106
<211> LENGTH: 15
<212> TYPE: PRT
<213> ORGANISM: Artificial Sequence
<220> FEATURE:
```

```
<223> OTHER INFORMATION: PEPT49

<400> SEQUENCE: 106

Phe Lys Gly Phe Trp Ser Glu Trp Ser Pro Ser Tyr Tyr Phe Arg
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: PEPT50

<400> SEQUENCE: 107

Trp Ser Glu Trp Ser Pro Ser Tyr Tyr Phe Arg Thr Pro Glu Ile
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: PEPT51

<400> SEQUENCE: 108

Ser Pro Ser Tyr Tyr Phe Arg Thr Pro Glu Ile Asn Asn Ser Ser
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: PEPT52

<400> SEQUENCE: 109

Tyr Phe Arg Thr Pro Glu Ile Asn Asn Ser Ser Gly Glu Met Asp
1               5                   10                  15
```

NON-ANTAGONISTIC ANTIBODIES DIRECTED AGAINST THE ALPHA CHAIN OF THE IL7 RECEPTOR EXTRACELLULAR DOMAIN AND USE THEREOF IN CANCER TREATMENT

CROSS REFERENCE TO RELATED APPLICATIONS

This patent application is 35 U.S.C. § 371 U.S. National Phase Application of International Patent Application No. PCT/IB2017/000293, filed Feb. 28, 2017 and incorporated by reference in its entirety, which claims the benefit of U.S. Provisional Application No. 62/301,127, filed Feb. 29, 2016 and incorporated herein by reference in its entireties.

BACKGROUND

The invention concerns humanized antibody directed against the extracellular domain of the alpha chain of the receptor for interleukin7 (IL-7), especially the receptor for human IL-7 expressed on human cells (also designated human IL-7Ralpha or IL-7Ra or CD127) and which does not interfere with the IL-7 or TSLP signaling pathways.

IL-7R signalling. Binding of IL-7 to IL-7R triggers the activation of several signalling pathways, including the Janus kinases (JAK)-1 and -3, signal transducer and activator of transcription 5 (STAT5) and phosphatidylinostol 3-kinase (PI3-k). STAT1 and STAT3 pathways are reported to be activated, although they do not seem to be the main pathways. The activation of the STAT5 pathway is required for the induction of the anti-apoptotic protein Bcl-2 and the prevention of the entry of the pro-apoptotic protein Bax in the mitochondrion and thus for survival of thymic developing T cell precursors. The activation of the PI3-k pathway results in the phosphorylation and cytoplasmic retention of the pro-apoptotic protein Bad.

The importance of the IL7-CD127 pathway for naïve T-cell homeostasis is underlined by several recent studies showing that expression levels of membrane-bound IL-7Ra on conventional CD4+ T cells correlate with frequencies of recent thymic emigrant (RTE)-CD4+ T cells in healthy individuals and HIV-infected patients as well as in patients with multiple sclerosis (MS) (Albuquerque et al., 2007) (Broux et al., 2010).

Thymic Stromal Lymphopoietin, (TSLP) is an epithelial Cell Cytokine that is active in lymphopoiesis and in particular is involved in regulation of development of cells of the immune system, said regulation impacting in particular the maturation of said cells. Human TSLP (Accession number AF338732) is a factor which exerts polarization of dendritic cells, promote T and B cell proliferation and differentiation and which has been shown to play a role in skin and lung diseases (He and Geha, 2010).

Accordingly TSLP has been shown to associate to various pathologies including airway inflammatory disease and atopic dermatitis in human and mice (Ying et al., 2008) (Jariwala et al., 2011). In addition TSLP has been shown to associate to regulation of intestinal immunity and inflammation (Taylor et al., 2009). TSLP signaling pathways have been shown different, at the molecular level, from IL-7-induced signaling (Rochman et al., 2010).

SUMMARY

The invention concerns humanized antibody directed against the extracellular domain of the alpha chain of the receptor for interleukin7 (IL-7), especially the receptor for human IL-7 expressed on human cells (also designated human IL-7Ralpha or IL-7Ra or CD127) and which does not interfere with the IL-7 or TSLP signaling pathways.

The antibody of the invention does not have antagonistic effect on the IL-7 receptor, but may still present cytotoxic activity against CD127 positive cells. In a particular embodiment the antibody does not have or agonistic effect on the IL-7 receptor.

The invention provides as an example, an antibody which recognizes a human CD127 epitope comprising sequence of SEQ ID No55 of table 6.

Accordingly the antibodies of the invention are suitable for use in order to treat Cancer related with proliferation of CD127 positive cells or with an infiltration of CD127 positive cells that block the immune system in a tolerant condition.

The invention also concerns fragments of the antibodies, in particular antigen-binding fragments of these antibodies, or molecules comprising such antibodies or such fragments as components for the preparation of therapeutic agents, in particular immunotherapeutic agents.

Figure 1A:
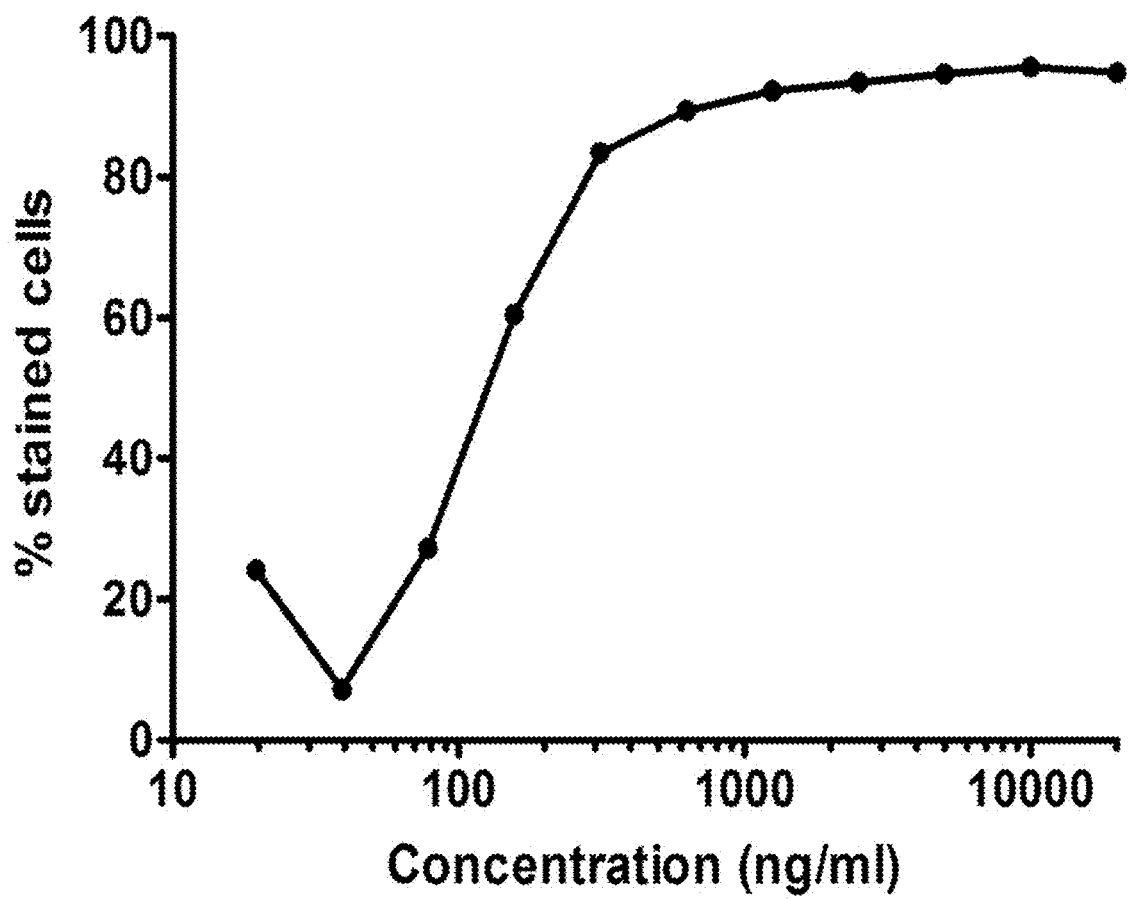
FIG. 1

Effi3 Binding Assay to CD127 by Facs and ELISA. A. Shows the percentage of CD127 positive cells over a dose response of Effi3 staining. B. Effi3 binding activity. A. Binding activity assay, anti-CD127 antibodies were tested on Sandwich ELISA: MD707-3 (start line), Effi3 variant VH3VL3 (Triangle line) and Effi3 variant VH3VL4 (square line).

FIG. 2

Stability assay by ELISA over time at different temperature: the figure shows the absorbance of the Effi3 antibody from DO to 28 and stored at RT (triangle line), 4° C. (square line), 37° C. (cross line), −80° C. (stare line) or defrosted 3 times at −80° C. (bar line).

FIG. 3

Effect of the binding of Effi3 on CD127 after IL7 or TSLP stimulation. A. Inhibition of IL-7 induced pSTAT5+T lymphocyte in dose-response to MD707-3 mAb (black squares), no effect of the Effi3 mAb (empty squares) on IL7-dependent P-STAT5. B. Effect of TSLP-induced TARC production by anti-human CD127 antibodies. Quantification by ELISA of TARC production in supernatant of human blood CD1C+ dendritic cells cultured for 24 hours with 15 ng/ml of TSLP and different concentration of anti-human CD127 antibodies: MD707-3, Effi3 or anti-TSLP antibody as a positive control of inhibition.

FIG. 4

Cytotoxicity study of Effi3 variants, humanized clones of MD707-3, at different concentration and different ratio between Effector and target cells. Antibody-dependent cellular cytotoxicity (ADCC) after incubation with NK human as effector (E) cells of Effi3 H3L3 and Effi3 H3L4 on 51Cr-labeled LAL-T DND41 (CD127+)human T-cell acute lymphoblastic leukemia (T-ALL) cell lines at different ratio: (E:T=30:1; 10:1 and 3:1). Percentage of specific cytotoxicity was determined by 51Cr release.

FIG. 5

Human CD127 Amino acid sequence (SEQ ID NO: 40): the bold amino acids is the linear epitope sequence recognize by Effi3 antibody.

FIG. 6

Amino acid (aa) sequence of the Effi3 VH3 with IgG1m isotype (SEQ ID NO: 2): aa in grey shaded box: signal peptide; aa in bold and italic: CDR1, CDR2 and CDR3; aa underlined: IgG1m constant region; taller bold aa: humanized aa.

FIG. 7

Amino acid (aa) sequence of the Effi3 VL4 with CLkappa constant region (SEQ ID NO: 6): aa 1-20 in grey shaded box: signal peptide, aa in bold and italic: CDR1, CDR2 and CDR3; aa underlined: CLkappa constant region; taller bold aa in shaded boxes: humanized aa.

DETAILED DESCRIPTION

"CD127-positive cells" as used in the present invention designates cells expressing CD127 at their cell surface, in particular human cells expressing human CD127. In most cases, CD127-positive cells express CD127 in a complex forming the IL-7R (IL-7R-positive cells) and/or in a complex forming the TSLPR (TSLPR-positive cells). CD127 is expressed by various cells, including by both memory and naive T cells. CD127 is in particular expressed by effector T cells (Teff), including resting and memory T cells, and by immature B cells, and is also expressed by resting natural regulatory T cells (natural Treg), although at considerably lower levels. IL-7Ra is essential for promoting thymocyte differenciation and clonal expansion of lymphocytes.

The antagonist properties as disclosed in the present invention may be in particular antagonism toward IL-7R signaling induced by IL-7, especially human IL-7. An antagonist of IL-7R signaling induced by IL-7 can be identified by measuring the inhibition of STAT5 phosphorylation as described in the Examples. The IL7-induced phosphorylation of STAT5 is a marker of IL7R activation and an antibody antagonizing IL7-IL7R interaction is expected to decrease IL7-induced phosphorylation of STAT5.

In a particular embodiment, the invention relates to the use of antibodies defined herein in order to deplete subpopulations of lymphocytes, or other cell populations expressing CD127, especially human CD127 (including normal or pathologic T and B lymphocytes, NK cells, dendritic cells and other cell types including epithelial cells) as a result of cytotoxic action of the antibodies, possibly but not exclusively through ADCC (Antibody-Dependent Cellular Cytotoxicity) and optionally through CDC (Complement-Dependent Cytotoxicity). Accordingly the invention concerns the use of the antibodies in the treatment of pathologic conditions involving the alteration of immune response in a human patient leading to dominant tolerogenic state involving CD127 positive cells as well as destruction of malignant CD127-positive cells such as in hematologic cancers.

The invention thus provides means suitable for use in pathologies such as those induced by autoimmune diseases, graft rejection, allergic diseases, respiratory diseases, chronic viral infections, lymphoma, leukemia or other cancer diseases including those resulting from solid tumors (e.g. breast cancer) when these pathologies are associated with CD127 positive cells (such as described in Ujiie et al, OncoImmunology 4:6, e1009285; June 2015). Naive T cells are partly responsible for acute rejection of transplanted organs and tissues. These cells can be controlled by current immunosuppressive drugs (calcineurin inhibitors) and by monoclonal antibodies that block costimulation (anti-adhesion, CD80/86 inhibitors). Memory T cells are also responsible for transplant rejection. Memory T cells accumulate in man due to the acquired immune history, mainly former reactions against viruses. It has been shown that memory T cells can be reactivated by alloantigens as a result of "heterologous immunity", which is the cross-reaction of our anti-viral defenses with alloantigens (Adams et al., 2003). Heterologous immunity represents a potent barrier to tolerance induction since memory T cells, in contrast to naive T cells, are programmed to activate quickly, with a reduced requirement for costimulatory signals. Memory T cells may also be involved in chronic rejection. Beside their role in organ and tissue transplantation, naïve and memory T cells are also co-responsible for many autoimmune diseases. This is the case for ulcerative colitis (Shinohara et al., 2011), rheumatoid arthritis, psoriasis or graft-versus-host disease.

Furthermore, several malignant cells have been shown to display IL-7R. This is the case for Sezary cutaneous lymphoma (60% of them), or childhood acute lymphoblastic leukemia in which about 15% of the cases develop gain-of-function mutation in CD127, rendering these tumors partially IL-7 dependent (Shochat et al., 2011).

The depletion of T lymphocytes has been an obvious immunosuppressive approach to counteract allograft rejection or fight autoimmunity. However, total T cell depletion might not be favorable for the induction of immunological tolerance.

Targeting T cell subpopulations or selectively activated (effector) T cells, without modifying Treg cells, could constitute a pro-tolerogenic approach (Haudebourg et al., 2009). CD127 may thus be regarded as a potential attractive therapeutic target for monoclonal antibodies (Mabs) aimed at modulating immune responses since such monoclonal antibodies could have the potential of depleting effector but not regulatory lymphocytes. It has been assumed accordingly that they might show efficacy in transplantation, autoimmunity (Michel et al., 2008) and malignancies by antagonizing access of IL-7 to IL7-R and thereby limiting T and B cell function and growth.

A therapy with a monoclonal antibody against CD127+ cells without interfering with IL-7 and TSLP pathways could fulfill that goal by eliminating/neutralizing naïve and memory T cells while preserving Treg cells or by eliminating CD127-positive malignant cells.

In this context, monoclonal antibodies against IL-7Ra having antagonist properties toward IL-7Ra have been disclosed in WO2010/017468 and their humanized versions in WO2011/094259 with a view to treat autoimmune diseases like multiple sclerosis. The described antibodies are said to be antagonist for IL-7 binding to its receptor, and active against $T_H17$ and $T_H1$ cells expansion and survival which were said to require IL-7 interaction with their CD127 receptor. Similarly, anti-CD127 antibodies reported in WO2011/104687 or in WO2013/056984, which are contemplated for use in the treatment of diabetes, lupus, rheumatoid arthritis and other autoimmune diseases, have not been discussed with respect to their possible effect on their interaction with TSLP-induced signalling has not been reported.

In a publication (Racapé et al., 2009) the authors analysed the interest of the IL-7 receptor alpha as a potential therapeutic target in transplantation. Having reviewed the expression of IL-7Ralpha on various T cells and IL-7 responsive cells, the authors determined whether targeting memory T cells expressing IL-7Ralpha could prolong allograft survival in mice and conclude that targeting IL-7 or IL-7Ralpha would advantageously spare Treg cells. Among the perspectives, the authors pointed out that targeting either IL-7 or IL-7Ralpha in therapeutic treatment might have different consequences on the survival of the cells expressing CD127 and might elicit different types of lymphopenia. The question of the effects of antibodies that would be directed against IL-7Ralpha depending upon whether they would be blocking or neutralizing or cytotoxic antibodies was also posed from a conceptual point of view. The authors nevertheless did not show having obtained and assayed such antibodies and rather expressed the need for further study to assess the relevance of the hypothesis. In view of the drawbacks of available therapeutic approaches in immune related diseases and other diseases involving the IL-7/IL-7Ralpha such as different types of cancers, including some breast cancers, there is still a need for further drug candidates, especially for candidates active with respect to more selective targets for the purpose of controlling e.g. modulating immune activation in human patients.

Such an antibody could be efficient in a combination approach for cancer therapy with first line treatment radiotherapy, chemotherapy, immunotherapy particularly with check point inhibitors such as anti-CTLA4 or anti-PDL1 or anti-Sirpalpha antibodies.

The inventors fulfil this need in providing antibodies that have the capacity to recognize and eliminate effector T cells while preserving regulatory T cells capable of inducing tolerance in transplantation and that have shown ability to eliminate malignant CD127+ leukemia cells.

Figure 3A:
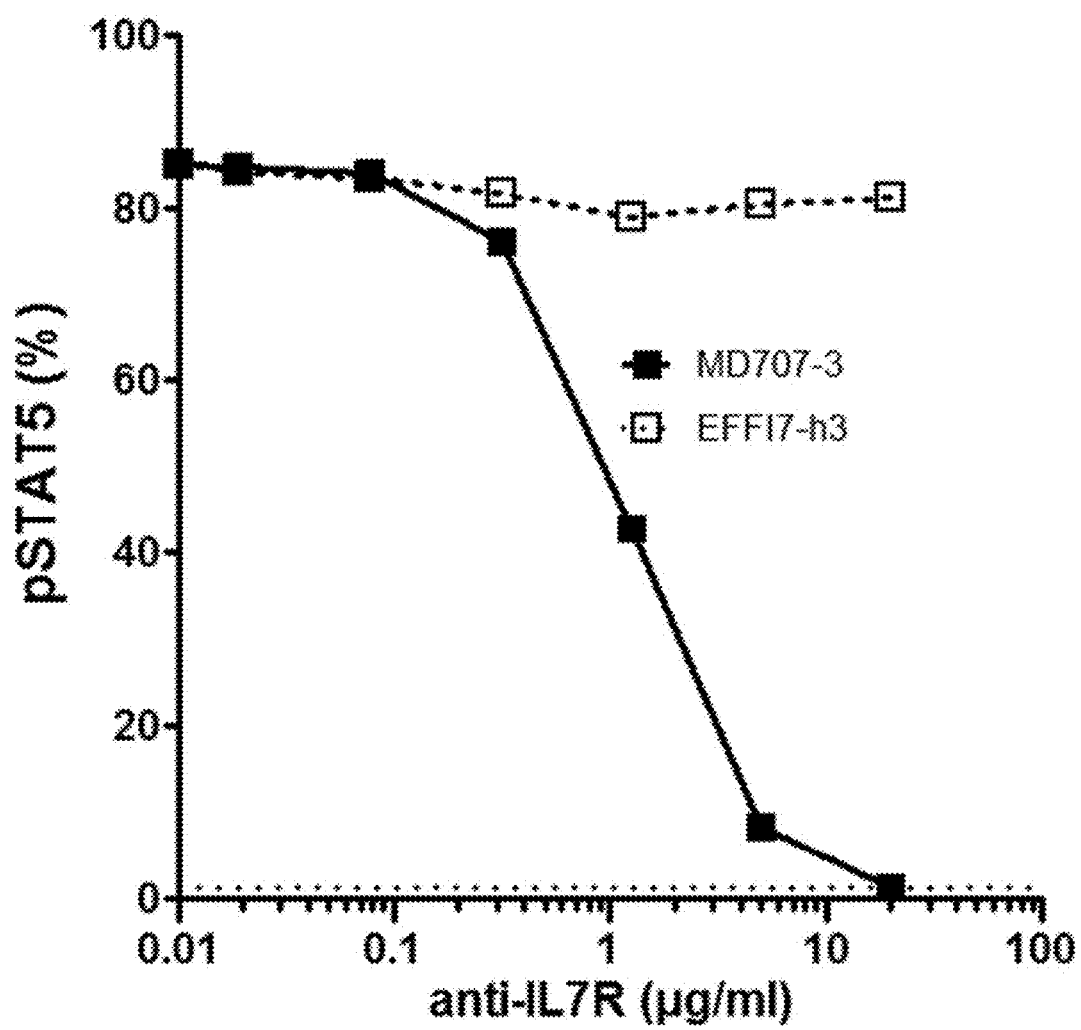
Figure 3B:
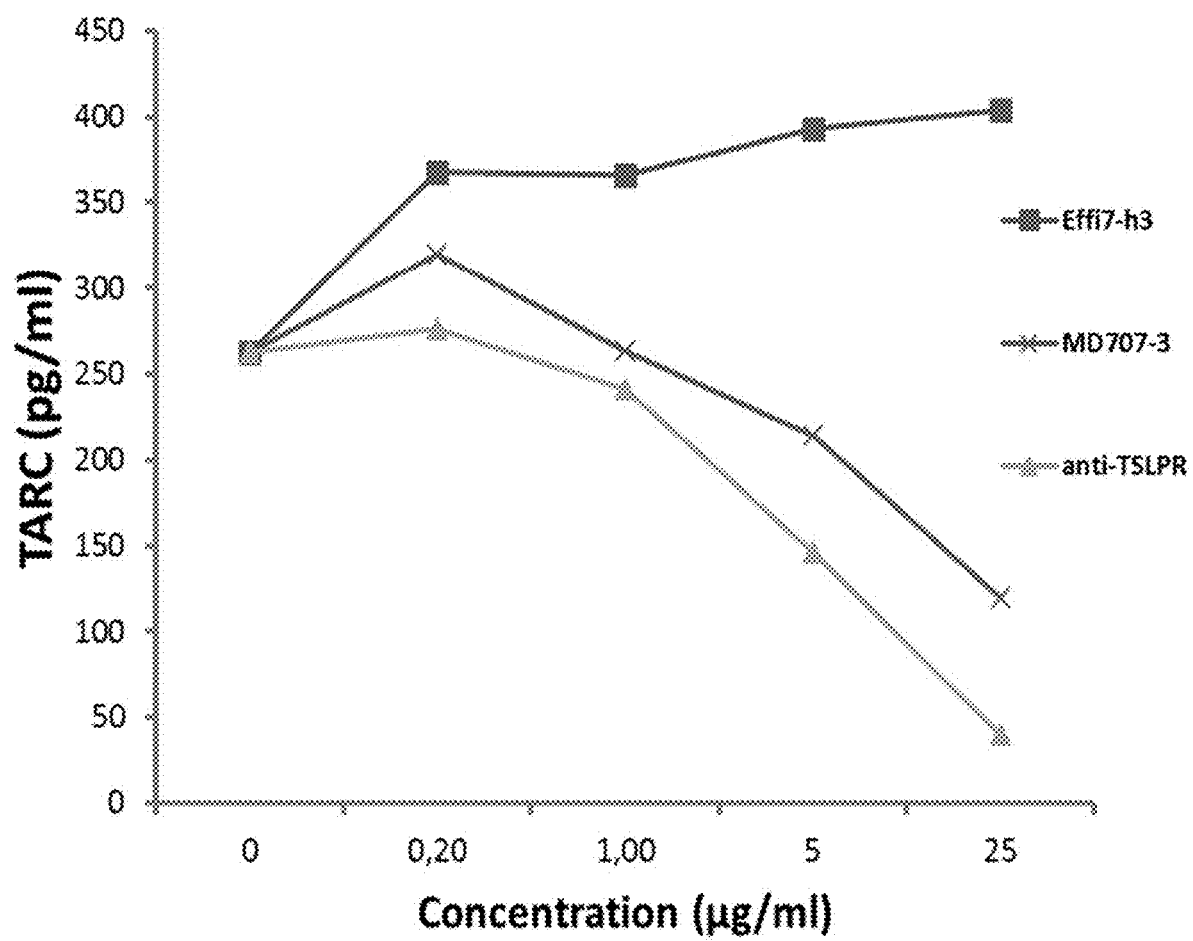

The international patent application WO2013056984 discloses antibodies directed against the extracellular domain of the alpha chain of the human IL7-R with an antagonist activity and a cytotoxic activity in order to deplete subpopulations of lymphocytes or other cell populations expressing CD127. The disclosed MD707-3 antibody comprises the VH and VL chains (Sequences 56 and 57 in Table 6) which served to derive the present antibody. The MD707-3 antibodies are antagonists of the IL7-R and in particular inhibit the phosphorylation of Stat5 induced by IL7. By contrast, the humanized antibody of the present invention, derived from MD707-3, surprisingly is not an IL7-R antagonist while retaining good binding to the extracellular domain of CD127 and the possibility to mediate cyotoxic effect on cells expressing CD127. Furthermore, the MD707-3 antibody is a TSLPR antagonist, as shown in FIG. 3.b herein, while the humanized antibody derived therefrom, designated Effi3 herein, is not.

The inventors provide means suitable in this context, as they obtained monoclonal antibodies against IL-7Ra and that does not interfere with the TSLP pathway contrary to what was observed by the inventors with MD707-3 antibody, parent of the antibody of the present invention. MD707-3 showed TSLP antagonist properties and potentiate the maturation of dendritic cells characterized by the expression at cell surface of CD80 and CD86 (data not shown). The antibody of the present invention constitutes a new products for evaluating therapeutic benefits of targeting CD127+ cells with depleting action and without antagonizing nor activating IL7 pathway nor TSLP pathway.

The invention thus concerns an antibody or an antigen-binding fragment thereof which (i) binds specifically the extracellular domain of the alpha chain of the receptor to IL-7 (designated CD127), especially of the alpha chain of the IL-7 receptor expressed by human CD127 positive cells, and which optionally exhibits cytotoxic activity against human T cells expressing CD127 (CD127+ cells), and (ii) is not an IL7-R or TSLP-R antagonist, in particular is not a human IL-7 or a human TSLP antagonist and in particular does not inhibit STAT5 phosphorylation induced by IL7 and/or does not inhibit TARC (Thymus and Activation Regulated Chemokine, also designated CCL17) production by blood derived human dendritic cells stimulated by TSLP.

The expression "binds specifically" or any equivalent refers to the capability of the antibody or the antigen-binding fragment of the invention to interact with CD127 and to bind with CD127, preferably human CD127, while they do not bind or they bind with a significantly weaker binding affinity to other molecules, in particular to other proteins. Binding and binding specificity can be assayed by SPR (Surface Plasmon Resonance e.g. Biacore), ELISA or Western Blot analysis. In a particular embodiment, the antibody or the antigen-binding fragment thereof or the chimeric molecules comprising said antibody or antigen-binding fragments target and bind to CD127 as an isolated protein with a dissociation constant (Kd) lower than 5E-10M, in particular lower than 3E-10M.

Although it is not specified in each disclosed embodiment, the defined properties or features of the antibodies and antigen-binding fragments thereof and the defined properties or features of products made using these antibodies or antigen-binding fragments thereof are especially defined with respect to the cited molecules when these molecules are human molecules (such as CD127, IL-7, TSLP . . . ).

The invention provides in particular two variants of an antibody, designated Effi3, which comprise:

A heavy chain variable domain designated Effi3-VH3 or VH3 or Effi3-VHvar3 or VHvar3 (sequence of SEQ ID No2 in Table 6, or sequence of SEQ ID No8 which includes a signal peptide), which comprises CDRs designated as VH3-CDR1, VH3-CDR2, VH3-CDR3 or equivalent designations with Effi3-VH3, Effi3-VHvar3 or VHvar3 prefixes; and either, for the variant designated Effi3-VH3VL3, a light chain variable domain designated Effi3-VL3 or VH3 or Effi3-VLvar3 or VLvar3 (sequence of SEQ ID No4 in Table 6, or sequence of SEQ ID No10 which includes a signal peptide), which comprises CDRs designated as VL3-CDR1, VL3-CDR2, VL3-CDR3 or equivalent designations with Effi3-VL3, Effi3-VLvar3 or VLvar3 prefixes;

or, for the variant designated Effi3-VH3VL4, a light chain variable domain designated Effi3-VL4 or VH3 or Effi3-VLvar4 or VLvar4 (sequence of SEQ ID No6 in Table 6, or sequence of SEQ ID No12 which includes a signal peptide), which comprises CDRs designated as VL4-CDR1, VL4-CDR2, VL4-CDR3 or equivalent designations with Effi3-VL4, Effi3-VLvar4 or VLvar4 prefixes.

Since the VL-CDR2 and VL-CDR3 are identical for the VL3 and VL4 light chains, they are indifferently designated VL3-CDR2, VL4-CDR2 or VL3/4-CDR2 and VL3-CDR3, VL4-CDR3 or VL3/4-CDR3, respectively.

The Effi3 antibody is provided in particular with the constant domains IgG1m E333A (sequence of SEQ ID No28) and CLkappa (sequence of SEQ ID No34) for the heavy and light chains, respectively. The antibody of the invention is humanized. Accordingly, in addition to the substitutions in the CDR sequences disclosed herein, the antibodies of the invention are modified in the framework residues of their VH and/or VL sequences by substitution of amino acid residues, relatively to the rat MD707-3 antibody, in particular such residues are modified to more closely match naturally occurring human antibodies. Humanization can be performed by resurfacing or by CDR grafting according to known techniques. Example substitutions are disclosed in the Examples section. Resurfacing is especially achieved by the substitution of rodent residues for human amino acid residues. The substitution is performed in a way that maintains the framework structure of the original antibody and also the CDRs presentation, thereby enabling that the frameworks and CDRs interactions in the resurfaced antibody preserve native conformation of the surface contacting the antigen so that it retains antigen binding affinity.

The following substitutions within the CDRs were introduced in the present antibody, relatively to the MD707-3 rat antibody (whose sequence is disclosed as SEQ ID No56 for the heavy chain and SEQ ID No57 for the light chain, thereby providing the reference for the positions of the substituted amino acid residues): S30T in VH-CDR1 and E64D in VH-CDR2, these two substitutions defining the CDRs of Effi3-VH3; L59R in VL-CDR2 and A60D in VL-CDR2, these two substitutions defining the CDRs of Effi3-VL3. In addition to the substitutions of Effi3-VL3 chains, the CDRs of Effi4-VL4 chain have an additional S28D substitution in VL-CDR1.

In particular preferred embodiments, the antibody or antigen-binding fragment thereof comprises or consists in:
  a heavy chain with the CDRs of the VH3 heavy chain disclosed herein as sequence of SEQ ID No2 in Table 6, in particular with VH3-CDR1, VH3-CDR2 and VH3-CDR3 having the sequences of SEQ ID No14, 16 and 18, respectively, in Table 6; and
  a light chain with the CDRs of the VL3 or of the VL4 light chain disclosed herein as sequences of SEQ ID No No4 and 6, respectively, in particular with VL3-CDR1, VL3-CDR2 and VL3-CDR3 having the sequences of SEQ ID No20, 22 and 24 respectively, or with VL4-CDR1, VL3-CDR2 and VL3-CDR3 having the sequences of SEQ ID No26, 22 and 24 respectively.

In a particular embodiment, the antibody or antigen-binding fragment additionally has the V101T and/or V102T substitution(s) in VH-CDR3 (CDR3 of the heavy chain).

In another embodiment, the antibody or antigen-binding fragment additionally has no substitution at positions V101 and/or V102 in VH-CDR3 (CDR3 of the heavy chain) or has no V101 or V102 substitution.

In a particular embodiment of the invention, the humanized antibody is characterized by the presence in their VH and/or VL chains of one or several of the following additional amino acid residue substitutions at positions identified with respect to the Kabat numbering in the framework regions of the chains, with respect to the MD707-3 VH and VL sequences (the indicated residue results from the substitution, the original rat residue of MD707-3 are disclosed in e.g. Tables 1 to 4 in the Examples):
  in the VH sequence: at position 3 a residue Q, at position 15 a residue G, at position 16 a residue G, at position 21 a residue T, at position 80 a residue T, at position 87 a residue S, at position 91 a residue E, at position 95 a residue T, at position 118 a residue L, and/or
  in the VL sequence: at position 7 a residue S, at position 9 a residue S, at position 11 a residue L, at position 12 a residue P, at position 18 a residue P, at position 47 a residue Q, at position 50 a residue K, at position 68 a residue S, at position 73 a residue G, at position 82 a residue R, at position 85 a residue A, at position 90 a residue T.

In particular embodiments where the antibody of the invention has the S28D substitution in VL-CDR1 (i.e. has the VL-CDR1 of VL4, with the sequence of SEQ ID No26), the antibody has at least the E73G framework substitution disclosed above.

In particularly preferred embodiments, the antibody of the invention has all of the framework residue substitutions disclosed above in the heavy chain. In particularly preferred embodiments, the antibody of the invention has all of the framework residue substitutions disclosed above in the light chain, or all of the framework residue substitutions disclosed above but for the G in position 73, which is preserved as an E residue. In a particular embodiment the antibody or antigen-fragment thereof has a VL3-CDR1 with the sequence of SEQ ID No20 and has in position 73 a preserved E residue.

In particularly preferred embodiments, the antibody of the invention has (or the antigen binding fragment comprises):
  a heavy chain with the sequence of VH3, i.e. sequence of SEQ ID No2; and
  a light chain with the sequence of VL3 (sequence of SEQ ID No4) or of VL4 (sequence of SEQ ID No6).

These features relating to so-called "humanized positions" can be combined with any or all embodiments of the definition of the antibodies of the invention.

In a particular embodiment of the invention, the antibodies of the invention or their antigen-binding fragments directed against the CD127 molecule present in the IL-7 receptor have furthermore the property of being cytotoxic against human cells, especially human T cells expressing said receptor and in a preferred embodiment against tumoral T cells.

In a particular embodiment of the invention, the antibodies or antigen binding fragments thereof target and bind the same IL7-R alpha chain when it is combined with TSLP-Receptor (also known as CCRF2; Accession Number AF338733) as a receptor for TSLP (Reche P. A. et al, 2001).

An "antigen-binding fragment" of an antibody of the invention is a part of the antibody, i.e. a molecule corresponding to a portion of the structure of the antibody of the invention that exhibits antigen-binding capacity for alpha chain of the IL-7 receptor for human IL-7, possibly in its native form; such fragment especially exhibits the same or substantially the same antigen-binding specificity for said antigen compared to the antigen-binding specificity of the corresponding four-chain antibody. Advantageously, the antigen-binding fragments have a similar binding affinity as the corresponding 4-chain antibodies. However, antigen-binding fragment that have a reduced antigen-binding affinity with respect to corresponding 4-chain antibodies are also encompassed within the invention. The antigen-binding capacity can be determined by measuring the affinity of the antibody and of the considered fragment. These antigen-binding fragments may also be designated as functional fragments of antibodies. Antigen-binding fragments of antibodies are fragments which comprise their hypervariable domains designated CDRs (Complementary Determining Regions) or part(s) thereof encompassing the recognition site for the antigen, i.e., IL-7Ra of human IL-7, thereby defining antigen recognition specificity. Each Light and Heavy chain (respectively VL and VH) of a four-chain immunoglobulin has three CDRs, designated VL-CDR1, VL-CDR2, VL-CDR3 and VH-CDR1, VH-CDR2, VH-CDR3, respectively.

Thus the invention relates to fragments of antibodies of the invention, which comprise or consist in all of CDRs among VL-CDR1, VL-CDR2, VL-CDR3 and VH-CDR1, VH-CDR2 and VH-CDR3 of VL3 or VL4 and of VH3, respectively.

The skilled person will be able to determine the location of the various regions/domains of antibodies by reference to the standard definitions in this respect set forth, including a reference numbering system (Martin, 2001) Protein Sequence and Structure Analysis of Antibody Variable Domains. In: Antibody Engineering Lab Manual, ed.: Duebel, S. and Kontermann, R., Springer-Verlag, Heidelberg] or by reference to the numbering system of Kabat (Sequences of Proteins of Immunological Interest, $4_{th}$ Ed., U.S. Department of Health and Human Services, NIH, 1987) or by application of the IMGT "collier de perle" algorithm (http://www.imgt.org/IMGTindex/Colliers.html). In this respect, for the definition of the sequences of the invention, it is noted that the delimitation of the regions/domains may vary from one reference system to another. Accordingly, the regions/domains as defined in the present invention encompass sequences showing variations in length of +/−10%, and the localization of the concerned sequences within the full-length sequence of the antibodies may vary by +/−10%.

In a particular embodiment of the invention, the humanized antibody or antigen binding fragment thereof has the herein defined CDRs sequences (i.e. the CDR sequences of VH3 and of VL3 or VL4, possibly with the additional V101T and/or V102T substitution(s) in VH-CDR3), and further comprises in its framework regions, at positions determined in accordance to the Kabat numbering, one or several of the following amino acid residues:
  in the VH sequence: at position 3 a residue Q at position 15 a residue G, at position 16 a residue G, at position 21 a residue T, at position 80 a residue T, at position 87 a residue S, at position 91 a residue E, at position 95 a residue T, at position 118 a residue L,
  in the VL sequence: at position 7 a residue S, at position 9 a residue S, at position 11 a residue L, at position 12 a residue P, at position 18 a residue P, at position 47 a residue Q, at position 50 a residue K, at position 68 a residue S, at position 73 a residue G or a residue E, in particular a residue E, at position 82 a residue R, at position 85 a residue A, at position 90 a residue T.

The position of the above mentioned residues in the frameworks of the antibody or antigen-binding fragment thereof can also be retrieved from the sequences of the MD707 variable domains of the heavy and light chains as discloses in SEQ ID No56 (VH) and SEQ ID No57 (VL).

In another embodiment, the humanized antibody or antigen binding fragment thereof has the herein defined CDRs sequences (i.e. the CDR sequences of VH3 and of VL3 or VL4), and further comprises in its framework regions, at positions determined in accordance to the Kabat numbering, one or several of the following amino acid residues, in particular all of them:
  in the VH sequence: at position 3 a residue Q, at position 15 a residue G, at position 16 a residue G, at position 21 a residue T, at position 80 a residue T, at position 87 a residue S, at position 91 a residue E, at position 95 a residue T, at position 118 a residue L,
  in the VL sequence: at position 7 a residue S, at position 9 a residue S, at position 11 a residue L, at position 12 a residue P, at position 18 a residue P, at position 47 a residue Q, at position 50 a residue K, at position 68 a residue S, at position 73 a residue G or a residue E, in particular a residue E, at position 82 a residue R, at position 85 a residue A, at position 90 a residue T.

In particular embodiments where the humanized antibody or antigen-binding fragment thereof comprises a D residue at position 28 (in VL-CDR1, as in VL4-CDR1), said antibody or fragment comprises a G residue at position 73 (in the VL framework residues).

In particular embodiments where the humanized antibody or antigen-binding fragment thereof comprises a S residue at position 28 (in VL-CDR1, as in VL3-CDR1), said antibody or fragment comprises a E residue at position 73 (in the VL framework residues).

In particular preferred embodiments, the antibody or antigen-binding fragment thereof has all of the above-indicated residues at the indicated framework position in its heavy chain. In particular preferred embodiments, the antibody or antigen-binding fragment thereof has all of the above-indicated residues at the indicated framework position in its light chain, or has all of the above-indicated residues at the indicated framework position, but for position 73 in its light chain where an E residue is found.

Based on the structure of four-chain immunoglobulins, antigen-binding fragments can thus be defined by comparison with sequences of antibodies in the available databases and prior art (Martin, 2001), and especially by comparison of the location of the functional domains in these sequences, noting that the positions of the framework and constant domains are well defined for various classes of antibodies, especially for IgGs, in particular for mammalian IgGs. Such comparison also involves data relating to 3-dimensional structures of antibodies.

For illustration purpose of specific embodiments of the invention, antigen binding fragments of an antibody that contain the variable domains comprising the CDRs of said antibody encompass Fv, dsFv, scFv, Fab, Fab', F(ab')2 which are well defined with reference to Kabat (NIH 1987), Martin A. C. R. et al and also Roitt I. et al (Fundamental and Applied Immunology MEDSI/McGraw-Hill). Fv fragments consist of the VL and VH domains of an antibody associated together by hydrophobic interactions; in dsFv fragments, the VH:VL heterodimer is stabilised by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen binding sites, like the native immunoglobulin molecule; on the other hand, Fv (a VHVL dimmer constituting the variable part of Fab), dsFv, scFv, Fab, and Fab' fragments are monovalent, i.e. they comprise a single antigen-binding site (For review see (Chan and Carter, 2010).

Accordingly the invention relates to antigens-binding fragments encompassing the sequences which are disclosed herein and which are monovalent or divalent fragments with respect to antigen recognition and are the following:
  Fv fragment consisting of the VL and VH chains associated together by hydrophobic interactions;
  dsFv fragment wherein the VH:VL heterodimer is stabilised by a disulphide bond;
  scFv fragment wherein the VL and VH chains are connected to one another via a flexible peptide linker thus forming a single-chain protein;
  Fab fragment which is a monomeric fragment comprising the entire L chain, and a VH-CH1 fragment of the H chain, bound together through a disulfide bond;

Fab' fragment;

F(ab')2 fragment which comprises two Fab' fragments, and additionally a portion of the hinge region of an antibody.

These basic antigen-binding fragments of the invention can be combined together to obtain multivalent antigen-binding fragments, such as diabodies, tribodies or tetrabodies. These multivalent antigen-binding fragments are also part of the present invention.

Several researches to develop therapeutic antibodies had lead to engineer the Fc regions to optimize antibody properties allowing the generation of molecules that are better suited to the pharmacology activity required of them (Strohl, 2009). The Fc region of an antibody mediates its serum half-life and effector functions, such as complement-dependent cytotoxicity (CDC), antibody-dependent cellular cytotoxicity (ADCC) and antibody-dependent cell phagocytosis (ADCP). Several mutations located at the interface between the CH2 and CH3 domains, such as T250Q/M428L (Hinton et al., 2004) and M252Y/S254T/T256E+H433K/N434F (Vaccaro et al., 2005), have been shown to increase the binding affinity to FcRn and the half-life of IgG1 in vivo. However, there is not always a direct relationship between increased FcRn binding and improved half-life (Datta-Mannan et al., 2007). One approach to improve the efficacy of a therapeutic antibody is to increase its serum persistence, thereby allowing higher circulating levels, less frequent administration and reduced doses. Engineering Fc regions may be desired to either reduce or increase the effector function of the antibody. For antibodies that target cell-surface molecules, especially those on immune cells, abrogating effector functions is required. Conversely, for antibodies intended for oncology use, increasing effector functions may improve the therapeutic activity. The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns et al., 2009). Binding of IgG to the FcγRs or C1q depends on residues located in the hinge region and the CH2 domain. Two regions of the CH2 domain are critical for FcγRs and C1q binding, and have unique sequences in IgG2 and IgG4 (Armour et al., 1999) (Shields et al., 2001) (Idusogie et al., 2000) (Steurer et al., 1995) (Lazar et al., 2006) (Ryan et al., 2007) (Richards et al., 2008) (Labrijn et al., 2009).

In particular embodiments, the antibody of the invention has the following constant domains:
for the heavy chain, the IgG1m-E333A constant domain (sequence of SEQ ID No28 in Table 6) or the IgG4m-S228P (sequence of SEQ ID No30) or IgG2b (sequence of SEQ ID No32) domains;
for the light chain, the CLkappa constant domain (sequence of SEQ ID No34) or the CLlambda (sequence of SEQ ID No36) domain.

The antibody of the invention, in particular the humanized antibody may be a monoclonal antibody. Human cells expressing CD127 as a chain of IL-7 receptor, which are the target of the antibodies of the invention and fragments thereof, are mainly T lymphocytes and more precisely are subpopulations of effector T lymphocytes including naïve and memory T cells but are not regulatory T cells, especially not resting natural Treg. Memory T cells are generated as a result of antigen priming and mainly defined by their functional characteristics, including ability to undergo recall proliferation upon re-activation and differentiation into secondary effector and memory cells.

According to an embodiment of the invention, the antibodies and antigen binding fragments thereof, having "cytotoxic activity against T cells" or cytotoxic properties (cytotoxic antibodies) give rise to depletion in the effector T cell population by killing these cells and accordingly reduce the number of these cells when administered. To the contrary, these antibodies do not alter the subpopulation of regulatory T cells or do not alter it to a significant extent, allowing the Treg cells to perform their function.

According to a particular embodiment of the invention, the cytotoxic antibodies show Antibody-Dependent Cellular Cytotoxicity (ADCC). Antibody ADCC potential was considered positive when specific cytoxicity was superior to 5%.

In particular embodiments, the antibody of the invention comprises a heavy chain with the constant domain of human IgG1, with the E333A mutation, i.e. sequence of SEQ ID No28 (in Table 6). In particular embodiments, the antibody of the invention comprises a light chain with the CLkappa constant domain of human IgG1, with sequence of SEQ ID No34.

In particular embodiments, the antibody of the invention has a heavy chain disclosed herein as Effi3_VH3_IgG1m (E333A) with the sequence of SEQ ID No42. In particular embodiments, the antibody of the invention has a light chain disclosed herein as Effi3_VL3_ClKappa with the sequence of SEQ ID No50, or has a light chain disclosed herein as Effi3_VL4_Clkappa, with the sequence of SEQ ID No48.

ADCC properties can be evaluated in an ADCC assay such as the test described in the Examples. When the antibody is a rat antibody the effector cells used in the ADCC assay are LAK (Lymphokine-activated killer) cells of rat. When the antibodies are humanized the ADCC assay can be carried out on human NK cells.

According to another embodiment, an antibody or an antigen-binding fragment thereof within the frame of the invention is not an antagonist of IL7 and/or is not an antagonist of TSLPR. An "Antagonist of IL-7R" means that antibodies or antigen-binding fragments thereof of the invention, which target the IL-7Ralpha, have the effect of preventing the accessibility of the IL-7 receptor expressed on CD127 cells, especially human effector T cells, in particular human memory T cells, for its binding partner IL-7, especially human IL-7, while the antibodies or fragments themselves do not trigger signaling by the IL7-R receptor. The same definition applies similarly to "antagonists of the TSLPR", which bind to TSLPR, prevent binding of the ligand, and do not themselves trigger signaling. According to a particular embodiment of the invention, an antibody or an antigen-binding fragment thereof within the frame of the invention is not an "antagonist of CD127" which means that it is neither an antagonist of IL-7 nor an antagonist of TSLP. In this respect non antagonism with respect to IL-7 and TSLP may be defined as a combination of any embodiments provided hereafter as the particular embodiments for the definition of not being an antagonist of the IL-7R or not being an antagonism of TSLP. As a result of not being an antagonist of the IL-7 receptor, contrary to the antibodies of the prior art, the antibody of the invention or its functional fragment does not lead to strong lymphopenia due to the prevention of IL-7-dependent thymic T cells generation. A test for measurement of the antagonist properties of the antibodies or functional fragments thereof of the invention is described in the Examples. In particular embodiments, the antibody or antigen-binding fragment of the invention is an antagonist of CD127. In particular embodiments, the antibody or antigen-binding fragment of the invention is an antagonist of the IL7-R. In particular embodiments, the antibody or antigen-binding fragment of the invention is an antagonist of the TSLPR.

In particular embodiments, the antibody and antigen-binding fragments thereof, does not reduce TARC production of TSLP stimulated dendritic cells when administered. In particular embodiments, TARC production in TSLP-stimulated dendritic cells, in particular in conditions disclosed in the Examples section, is reduced by no more than 20%, preferably no more than 10% and even more preferably no more than 5% in the presence of antibodies at a concentration of 5 µg/mL or more (or in presence of an equivalent concentration of antigen-binding fragment), and/or is reduced by no more than 80%, preferably no more than 50%, more preferably no more than 25% and even more preferably no more than 10% in the presence of antibodies at concentrations of 25 µg/mL or more (or in presence of an equivalent concentration of antigen-binding fragment).

In particular embodiments, the antibody or antigen-binding fragment thereof does not inhibit STAT-5 signaling of the IL7-R induced by IL-7. In particular embodiments, STAT-5 phosphorylation in IL-7 stimulated cells, in particular in conditions disclosed in the Examples section, is reduced by no more than 30%, preferably by no more than 25% and even more preferably by no more than 20% in the presence of antibodies at a concentration of 0.1 µg/mL or more and preferably at a concentration of 0.5 µg/mL or more (or in the presence of an equivalent concentration of antigen-binding fragment) and/or is reduced by no more than 50%, preferably by no more than 35% and even more preferably by no more than 20% in the presence of antibodies at a concentration of 1 µg/mL or more (or in the presence of an equivalent concentration of antigen-binding fragment) and/or is reduced by no more than 90%, preferably by no more than 70%, more preferably by no more than 50% and even more preferably by no more than 20% in the presence of antibodies at a concentration of 5 µg/mL or more and preferably at a concentration of 10 µg/mL or more (or in the presence of an equivalent concentration of antigen-binding fragment).

Antibodies against the extracellular domain of the IL7-receptor (or the TSLPR), and in particular of CD127, may act as agonists of the IL7-R (or the TSLPR), i.e. they may compete with binding of the ligand, while their binding may lead to activation of all or part of the signaling pathways of the IL7-R (or the TSLPR) in the absence of ligand and/or to increased activation in the presence of ligand. In particular embodiments, the antibody or antigen-binding fragment of the invention is not an agonist of CD127. In particular embodiments, the antibody or antigen-binding fragment of the invention is not an agonist of the IL7-R. In particular embodiments, the antibody or antigen-binding fragment of the invention is not an agonist of the TSLPR. In a particular embodiment, the antibody or antigen-binding fragment of the invention is neither an agonist of the IL-7 pathway nor an agonist of the TSLPR pathway.

In particular embodiments, the antibody and antigen-binding fragments thereof, does not increase TARC production of TSLP-stimulated dendritic cells when administered. In particular embodiments, TARC production in TSLP-stimulated dendritic cells, in particular in conditions disclosed in the Examples section, is increased by no more than 60%, and more preferably by no more than 50% in the presence of antibodies at a concentration of 0.2 µg/mL or more, preferably at a concentration of 1 µg/mL or more and more preferably in the presence of 25 µg/mL or more (or in presence of an equivalent concentration of antigen-binding fragment). In particular embodiments, the antibody and antigen-binding fragment of the invention do not induce the production of TARC in cells in the absence of TSLP, in particular the production of TARC in the presence of the above concentrations of antibody or antigen-binding fragment and in the absence of TSLP is 35% or less, preferably 20 or less, and more preferably 10% or less, of that in the presence of TSLP and in the absence of the antibody or antigen-binding fragment.

In particular embodiments, the antibody or antigen-binding fragment thereof does not increase STAT-5 signaling of the IL7-R induced by IL-7. In particular embodiments, STAT-5 phosphorylation in IL-7 stimulated cells, in particular in conditions disclosed in the Examples section, is increased by no more than 20%, preferably by no more than 10% and even more preferably by no more than 5% in the presence of antibodies at a concentration of 0.1 µg/mL or more, preferably at a concentration of 1 µg/mL or more and even more preferably in at a concentration of 10 µg/mL or more (or in the presence of an equivalent concentration of antigen-binding fragment). In particular embodiments, the phosphorylation of STAT-5 in the absence of IL-7 and in the presence of the antibody or antigen-binding fragment at the above concentrations is 20% or less, preferably 10% or less and even more preferably 5% or less of said phosphorylation in the presence of Il-7 and in the presence of the antibody (or antigen-binging fragment).

The antibodies of the prior art which have both cytotoxic and antagonist properties for CD127 positive cells enable cumulative effects of these properties with respect to the depletion of effector T cells, especially of memory T cells especially, thereby enabling a stronger depletion (exhaustion of the pool of CD127+ cells) and corresponding reduction in the number of target T cells. The antibody of the invention induce a lesser depletion of CD127 T cells that does not induce lymphopenia that could be an adverse effect in some circumstances.

The invention also provides polynucleotides encoding the antibodies (and fragments) of the invention. Such polynucleotides are disclosed in particular in Table 6. They may be provided as isolated polynucleotides. The skilled person will realize that, due to degeneracy of the genetic code, polynucleotide sequences distinct from these explicitly disclosed may encode the same amino acid sequences; such polynucleotide sequences are also encompassed in the present invention.

In a particular embodiment, the polynucleotide is comprising the sequences of SEQ ID No13, 15, 17, 19, 21 and 23, or the sequences of SEQ ID No13, 15, 17, 25, 21 and 23, in particular comprising the sequences of SEQ ID No1 and 3 or the sequences of SEQ ID No1 and 5, in particular comprising the sequences of SEQ ID No41 and 47 or the sequences of SEQ ID No41 and 49.

In a particular embodiment, the invention relates to a vector comprising the polynucleotide of the invention, The vector may be a plasmid suitable for cell transfection or may be a vector suitable for cell transduction, such as a viral vector.

The antibody or antigen-binding fragment thereof may be obtained, in particular, by DNA synthesis. It is possible in particular to synthesize the cDNA of the desired antibody and to clone said cDNA in an appropriate vector. Synthesis, cloning and expression of an antibody (or antigen-binding fragment) may be performed according to methods common in the field and readily available to the skilled person.

An antibody or an antigen-binding fragment thereof of the invention is in particular advantageously raised against a molecule which is the CD127 expressed by human T cells, possibly raised from an immunization under the form of native polypeptide or recombinant molecule. Preferably, the antibody is raised against a polypeptide consisting of or comprising the epitope with the sequence ESG-YAQNGDLEDAELDDYSFSCYSQLE (ID No55 in Table 6).

Immunization can be carried out according to the protocol disclosed in the Examples below: Recombinant CD127 Fc Chimera (10975-H03H Sino Biological, Beijing, China) was used to immunize rats such as rats of the LOU/C IgkIA strain available at the University of Louvain, Belgium). Hybridoma were obtained by fusing spleen mononuclear cells with the LOU rat immunocytoma IR983F, a non secreting and azaguanine resistant cell line, according to a previously described procedure (Chassoux et al, Immunology 1988 65 623-628). Hybridoma were first screened according to the capacity of the secreted monoclonal antibodies to bind to recombinant CD127 molecule (CD127 Fc Chimera; 10975-H03H, Sino Biological, Beijing, China). Hybridoma were then screened for the capacity of their monoclonal antibodies to bind to the CD127 expressed by human T cells.

"Hybridoma cells" according to the invention are cells generated from fusion of antibody producing cells (B Lymphocytes) from an animal previously immunized with a selected immunogen and fusion partner which are myeloma cells enabling to provide immortality to the resulting fusion cell. Myeloma cells and antibody producing cells (B cells such as splenocytes) can be of the same origin, and are eukaryotic cells in particular mammalian cells of the same animal. They can be alternatively of different origin, thus giving rise to an heterohybridoma. Myeloma cells such as the LOU rat immunocytoma IR983F, a non-secreting and azaguanine resistant cell line are chosen among cells that fail to produce immunoglobulins in order to enable the prepared hybridoma to secrete only monoclonal antibodies of the desired specificity. Other cells suitable for promoting ADCC such as those described in the following pages for the preparation of the antibodies through expression in recombinant cells may be used instead of the rat immunocytoma. Such cells are advantageously cells having a low or no fucosylation capacity. Preparation of hybridoma suitable for carrying out the invention is performed according to conventional techniques. Embodiments are described in detail in the Examples of the present application of which the particular disclosed features can be adapted to other cells used as fusion partners. A particular hybridoma disclosed in the present invention is MD707-3 deposited under No I-4532 on Sep. 28, 2011 at the CNCM (Collection Nationale de Cultures de Microorganismes, Paris, France) under the provisions of the Budapest Treaty. Said hybridoma enables production of a rat antibody designated MD707-3 that has been modified according to the invention to provide humanized antibodies Effi3.

The antigen-binding fragments of the antibody may be obtained starting from the antibody, especially by using enzymatic digestion according to well known techniques including papain or pepsin digestion, or using any appropriate cleavage technique. They may be alternatively expressed in host cells modified by recombination with nucleic acid sequences encoding the amino acid sequence of said fragments, or may be synthesized, especially chemically synthesized.

Accordingly, the antibodies of the invention, including the modified antibodies, and the antigen-binding fragments of the antibodies can also be prepared by classical genetic engineering techniques, such as those described by Sambrook et al. [Molecular Cloning, A Laboratory Manual, 2nd Ed., Cold Spring Harbor Laboratory Press, Cold Spring Harbor, N. Y., (1989), and updated versions].

In accordance to the invention, "binding" to the IL-7Rα protein refers to an antigen-antibody type interaction and encompasses "specific binding" properties of the antibodies or antigen-binding fragments thereof which specific binding means that the antibodies or antigen-binding fragments bind to the IL-7Rα protein and furthermore do not bind or bind with a significant weaker affinity to other proteins (e.g. common cytokine receptor γ-chain). Binding specificity and binding can be assayed in accordance with the tests disclosed in the Examples and in particular can be assayed by ELISA, or Western Blot analysis.

The invention accordingly relates to the versions of the VH and VL polypeptides as disclosed above, that encompass the signal peptide or not. The signal peptide may be necessary during the preparation of the polypeptides in cells.

As the most significant property of a therapeutic antibody is the activity, it is important that substitutions proposed during the resurfacing and de-immunisation do not affect the affinity or stability of the antibody. A large amount of information has been collected in the last 20 years on humanization and grafting of the CDRs (Jones et al., 1986) (Ewert et al., 2003), the biophysical properties of antibodies (Ewert et al., 2003), the conformation of the CDR-loops (Chothia and Lesk, 1987) (Al-Lazikani et al., 1997) (North et al., 2011) and for the framework (Vargas-Madrazo and Paz-Garcia, 2003) (Honegger et al., 2009), which along with advances in protein modelling (Desmet et al., 2002) (Almagro et al., 2014) makes it possible to predictively humanize and de-immunise antibodies with retained binding affinity and stability. However, it generally remains necessary to test for the desired properties of an antibody with a modified sequence. Tests for the features of the antibody (or antigen-binding fragment) are disclosed herein, in particular in the Examples section.

The specific sequences disclosed herein for e.g. Effi3_VH3VL3 and Effi3_VH3VL4 are humanized to a large extent and further humanization would generally not be considered necessary, while reverting some substitutions to restore the original rat residues would generally not be considered advantageous at least if a humanized antibody is sought, in particular for administration in humans. In particular embodiments, the antibody is humanized and/or de-immunized. In particular embodiments, the antibody or antigen-binding fragment is suitable for administration in humans, and in particular does not induce an adverse immune reaction in humans due to the presence of non-human sequences, or does not induce such a reaction at a clinically unacceptable level. The skilled person would be aware that, if any improvement of a feature was sought by substitutions in the variant domain relative to the sequences disclosed in Table 6, only a limited number of substitutions would be expected to provide such improvement while preserving other features (whether or not said substitutions have the effect of restoring the original amino acids of the rat MD707-3 sequence). A small number of variants would therefore need to be tested, and could readily be tested using the methods herein and methods known to the skilled person for important features of the antibody, in particular binding to the extracellular domain of CD127, optionally competition with IL-7 and/or TLSP, antagonist effect to CD127, the IL7-R and/or TSLPR, optionally agonist effect to these receptors, effect on STAT-5 phosphorylation and/or TARC production and optionally cytotoxic, in particular ADCC-mediated, effect. Such variant sequences are encompassed in the present invention and comprise in particular:

variants having the CDR sequences of VH3 and VL3 or VL4 and wherein substitutions relative to said sequences are limited to framework residues, in particular wherein less than 20% (or less than 25 residues), preferably less than 10% (or less than 12 residues), more preferably less than 5% (or less than 6 residues) and even more preferably 3, 2 or 1 framework residue(s) are(is) substituted relative to said sequences;

variants having no more than 2 and preferably no more than 1 substitution(s) in each of their CDRs relative to the CDRs of VH3 and VL3 or VL4, preferably wherein at least 3, more preferably at least 4 and even more preferably 5 CDRs are unmodified (the modified CDRs each having 2 or less and preferably only one substitution); such variants optionally additionally having substitutions in the framework residues, with the preferred limitations above;

variants having V101T and/or V102T substitution(s) in VH-CDR3 and optionally additional substitutions in the CDRs and/or framework residues with the preferred limitations above;

variants having no V101T or V102T substitutions and in particular variants having no V101 and V102 substitutions wherein preferred variants either have either an S residue at position 28 in VL-CDR1 (i.e. has the VL-CDR1 of VL3, with the sequence of SEQ ID No20) and an E residue at position 73 in the VL framework sequences (as in VL3 with sequence of SEQ ID No4), or a D residue at position 28 in VL-CDR1 (i.e. has the VL-CDR1 of VL4, with the sequence of SEQ ID No26) and a G residue at position 73 in the VL framework sequences (as in VL4 with sequence of SEQ ID No6).

The invention also relates to a chimeric molecule comprising an antibody or a fragment thereof as defined herein, wherein said chimeric molecule is:

a chimeric protein, in particular an artificial protein, which retains the antigen-binding capacity of said antibody or antigen-binding fragment and which is an antigen-binding antibody mimetic or, a complex molecule having a plurality of functional domains which collectively provide recognition, binding, anchoring, signalling functions to said molecule, in particular a chimeric antigen receptor (CAR) comprising in association in a recombinant molecule, in particular in a fusion protein, (i) an ectodomain which derives from a scFv fragment of said antibody or antigen-binding fragment as defined herein or is such scFv fragment, (ii) a transmembrane domain for anchoring into a cell membrane and (iii) an endodomain which comprises at least one intracellular signalling domain.

In a particular embodiment, the chimeric molecule is a CAR molecule which comprises at least 2, advantageously at least 3 signalling domains wherein the signalling domains collectively enable at least one of the following properties:

initiation of T cell activation, such as provided by CD3 cytoplasmic domain

T cell mediated cytotoxicity, amplification of the T cell activation signal or costimulation of said signal, such as provided by costimulatory elements derived from receptors such as 4-1BB, CD28 or ICOS or OX40.

The invention also concerns a cell comprising an antibody or an antigen-binding fragment thereof as disclosed herein or comprising a chimeric molecule as defined herein, wherein the antibody or antigen-binding fragment thereof is exposed as an ectodomain at the surface of the cell. The cell may advantageously be a T cell, such as an autologous T cell of a patient or an allogenic T cell.

The signalling domain encompassed in the chimeric molecule may advantageously be derived from CD3 or from the Fc receptor Y chain.

The invention also relates to the use of these chimeric molecules such as mimetics or CAR molecules to target CD127+ T cells, in particular tumoral CD127+ T cells.

The invention also concerns a method or preparation of Chimeric Antigen Receptor (CAR) which comprises the steps of:

a. providing a polynucleotide encoding an antibody or an antigen-binding fragment thereof, in particular a scFv fragment, b. recombining said polynucleotide of a) at its C-terminal end with polynucleotides encoding from N- to C-terminal a transmembrane domain and at least one, in particular two intracellular signalling domain(s) suitable for providing stimulatory signal(s) to a cell, in particular to a T cell, more particularly to a human T cell.

c. expressing the recombinant molecule obtained in b) in a cell, especially in a T cell, more particularly in a human T cell, d. optionally selecting the produced chimeric antigen receptor for its properties after contacting the same with a cell expressing human CD127.

Among chimeric molecules the invention relates in particular to antigen-binding antibody mimetics, I.e., artificial proteins with the capacity to bind antigens mimicking that of antibodies. Such proteins comprise affitins and anticalins. Affitins are artificial proteins with the ability to selectively bind antigens. They are structurally derived from the DNA binding protein Sac7d, found in *Sulfolobus acidocaldarius*, a microorganism belonging to the archaeal domain. By randomizing the amino acids on the binding surface of Sac7d, e.g. by generating variants corresponding to random substitutions of 11 residues of the binding interface of Sac7d, an affitin library may be generated and subjecting the resulting protein library to rounds of ribosome display, the affinity can be directed towards various targets, such as peptides, proteins, viruses and bacteria. Affitins are antibody mimetics and are being developed as tools in biotechnology. They have also been used as specific inhibitors for various enzymes (Krehenbrink et al., J. mol. Biol., 383:5, 2008). The skilled person may readily develop affitins with the required binding properties using methods know in the art, in particular as disclosed in patent application WO2008068637 and the above-cited publication, in particular the generation of phage display and/or ribosome display libraries and their screening using an antigen as disclosed herein. Anticalins are artificial proteins that are able to bind to antigens, either to proteins or to small molecules. They are antibody mimetic derived from human lipocalins which are a family of naturally binding proteins. Anticalins are about eight times smaller with a size of about 180 amino acids and a mass of about 20 kDa (Skerra, Febs J., 275:11, 2008). Anticalin phage display libraries have been generated which allow for the screening and selection, in particular of anticalins with specific binding properties. The skilled person may readily develop affitins with the required binding properties using methods know in the art, in particular as disclosed in EP patent EP1270725 B1, U.S. Pat. No. 8,536,307 B2, (Schlehuber and Skerra, Biophys. Chem., 96:2-3, 2002) and the above-cited publication, in particular the generation of phage display and/or ribosome display libraries and their screening using an antigen as disclosed herein. Anticalins and affitins may both be produced in a number of expression systems comprising bacterial expression systems. Thus, the invention provides affitins, anticalins and other similar antibody mimetics with the features of the antibodies described herein, in particular with regard to the binding to CD127, the non-effect on the IL7 and/or TSLP signaling pathway all of which are contemplated as macromolecules of the invention.

The invention also concerns a method of manufacturing an antibody of the invention comprising the steps of immunizing a non-human animal, in particular a non-human mammal, against a polypeptide having the sequence of SEQ ID No55 and in particular collecting the resulting serum from said immunised non-human animal to obtain antibodies directed against said polypeptide.

In a particular embodiment of the method of manufacturing an antibody of the invention, additional steps may be performed in order to assess the properties of the prepared antibodies. Steps can in particular comprise the following carried out independently of each other:

a. testing (e.g. according to a method described in the Examples in sections titled "IL7R binding assay by cytofluorometry" and "rCD127 recognition of anti-h-CD127 Mabs assessed by ELISA") the ability of an antibody, an antigen-binding fragment or mimetic of such an antibody to bind to the extracellular domain of CD127, in particular to polypeptide comprising or consisting of the epitope with the sequence of SEQ ID No55, b. testing (e.g. according to a method described in the Examples in section titled "Phospho Stat5 activity assay") the effect of an antibody, an antigen-binding fragment or mimetic of such an antibody on the IL-7 signaling pathway, c. testing (e.g. according to a method described in the Examples in section titled "TARC secretion assay") the effect of an antibody, an antigen-binding fragment or mimetic of such an antibody on the TSLP signaling pathway, d. testing (e.g. according to a method described in the Examples in section titled "Antibody-Dependent Cellular Cytotoxicity") the cytotoxic activity, in particular ADCC activity of an antibody, an antigen-binding fragment or mimetic of such an antibody;

The method of manufacturing an antibody or antigen-binding fragment thereof or antigen-binding antibody mimetic of the invention may further comprise the following step selecting an antibody, an antigen-binding fragment or mimetic of such an antibody which specifically binds to the extracellular domain of CD127 which exhibits at least one of the following properties:

it is not an antagonist of CD127 and it does not inhibit IL-7 induced phosphorylation of STAT5 in cells expressing the IL7-R and/or, it does not inhibit TSLP-stimulated secretion of TARC in cells expressing the TSLP-R and/or, it is not an agonist of CD127 and/or, it does not increase IL-7 induced phosphorylation of STAT5 in cells expressing the IL7-R and/or, it does not increase TSLP-stimulated secretion of TARC in cells expressing the TSLP-R.

A particular embodiment of the method provides an antibody or antigen-binding fragment thereof or mimetic which specifically binds to the extracellular domain of CD127 and is not an antagonist of CD127 and does not inhibit IL-7 induced phosphorylation of STAT5 in cells expressing the IL7-R and does not inhibit TSLP-stimulated secretion of TARC in cells expressing the TSLP-R and is not an agonist of CD127 and/or does not increase IL-7 induced phosphorylation of STAT5 in cells expressing the IL7-R and does not increase TSLP-stimulated secretion of TARC in cells expressing the TSLP-R.

Another object of the invention is a pharmaceutical composition comprising an antibody or an antigen-binding fragment thereof or a chimeric molecule, according to the invention, with a pharmaceutical vehicle, wherein said pharmaceutical composition optionally further comprises a different active ingredient.

The invention also relates to a composition comprising as an active ingredient, an antibody or an antigen-binding fragment thereof or a chimeric molecule or a cell or a polynucleotide according to the definitions provided herein or a pharmaceutical composition, in a formulation suitable for controlling human CD127 positive cells survival or expansion, in particular human CD127 positive effector cells, especially CD127+ memory T cells survival or expansion, especially memory T cells which are both CD127+ and CD8+, or which are both CD127+ and CD4+ cells, when administered to a human patient.

A composition of the invention may further comprise an additional compound having a therapeutic immunomodulator effect, in particular on cells involved in allergy or autoimmunity. For illustration purpose immunomodulators of interest are other monoclonal antibodies targeting T cells, such as anti-CD3, anti-ICOS or anti-CD28 antibodies or recombinant proteins or antibodies targeting accessory cells such as CTLA4Ig or anti-CD40 antibodies.

According to another embodiment, a composition of the invention may further comprise immunotherapeutic agents useful in the context of the invention are selected from the group consisting of therapeutic vaccines (DNA, RNA or peptide vaccines), immune checkpoint blockers or activators or immunoconjugates such as antibody-drug conjugates.

Immunotherapeutic agents that could take cancer vaccines from interesting biological phenomena to effective therapeutic agents include: T-cell growth factors to increase number and repertoire of naive T cells, growth factors to increase the number of dendritic cells (DCs), agonists to activate DCs and other antigen-presenting cells (APCs), adjuvants to allow and augment cancer vaccines, agonists to activate and stimulate T cells, inhibitors of T-cell checkpoint blockade, T-cell growth factors to increase the growth and survival of immune T cells, agents to inhibit, block, or neutralize cancer cell and immune cell-derived immunosuppressive cytokine.

Numerous targets and immune checkpoint blockers or activators are known in the art. In the context of the invention, examples of targets, in particular immune checkpoint blockers or activators that could be useful are anti-PDL1, anti-PD1, anti-CTLA4, anti-CD137, anti-Her2, anti-EGFR, anti-CD20, anti-CD19, anti-CD52, anti-CD-137, anti-CD2, anti-CD28, anti-CD40, HVEM, BTLA, CD160, TIGIT, TIM-1/3, LAG-3, 2B4 and OX40.

The invention accordingly concerns combination therapeutic means comprising as active ingredients:

an antibody or an antigen-binding fragment thereof, a chimeric molecule, a cell or a polynucleotide, as defined herein at least one further therapeutic agent selected from the group of chemotherapeutic agents, radiotherapeutic agents, surgery agents, immunotherapeutic agents, probiotics and antibiotics, wherein said active ingredients are formulated for separate, simultaneous, or combination therapy, in particular for combined or sequential use.

The invention relates in an embodiment to a combination product which is suitable for administration to a human patient in need thereof, and which comprises as active ingredients: (i) an antibody or an antigen-binding fragment thereof, a chimeric molecule, a cell or a polynucleotide, as defined herein and (ii) an additional immunotherapeutic agent, in particular an immunotherapeutic agent involving T cells, such as a T cell bearing a CAR molecule as defined herein or a CAR molecule targeting a cell receptor or antigen such as, CD19, CD20 CD52 or Her2. In a particular embodiment, the antibodies used are IgG1 antibodies and are used as a cytotoxic agent.

The invention concerns also an antibody or an antigen-binding fragment thereof or a chimeric molecule or a cell or a polynucleotide as defined or illustrated herein, for use as active ingredient in a combination or add-on therapeutic regimen in a patient in need thereof.

An antibody or an antigen-binding fragment thereof or a chimeric molecule or a cell or a polynucleotide according to the invention, a pharmaceutical composition or a composition as defined herein are in particular proposed for use in a human patient for treating pathologic conditions influenced by immune responses, especially by memory T cells responses. Accordingly, the inventors proposed that the antibody or antigen-binding fragment thereof, chimeric molecule according to the invention, pharmaceutical composition or composition as defined herein be used for the treatment of autoimmune or allergic diseases in particular allergic skin disorders, intestinal disorders or for transplant rejection or for the treatment of leukemia such as acute lymphoblastic leukemia (e.g. T-ALL) or lymphoma such as Hodgkin lymphoma, or the treatment of a cancer disease such as breast cancer associated with CD127+ cells, renal cancer, bladder cancer, lung cancer, pancreatic cancer, or for the treatment of a T cell cutaneous lymphoma, such as Sezary lymphoma, or for the treatment of the acute lymphoblastoid leukemia with gain-mutation of the IL7-R/TSLP pathway, mesothelioma.

In view of their particular activity in targeting CD127 positives cells and cytotoxic activity, the antibodies of the invention or antigen-binding fragments thereof are in particular suitable for use in treating respiratory diseases such as asthma, cystic fibrosis, eosinophilic cough, bronchitis, sarcoidosis, pulmonary fibrosis, rhinitis, sinusitis, chronic viral infections such as infections due to HIV, to papilloma virus, hepatitis virus, allergic diseases such as allergic asthma allergic rhinosinusitis, allergic conjunctivitis, atopic dermatitis, food allergies, lymphoma or leukemia (e.g. pre-B ALL), and autoimmune diseases involving a type Th2 deleterious response such as lupus, psoriasis, sjögren syndrome, ulcerative colitis, rhumatoId polyarthritis type 1 diabetes. The composition or the combination therapeutic means according to the invention are also suitable for use in treatment of a patient presenting with a disease involving CD127+ cell, such as the above cited ones. In particular the composition or the combination therapeutic means according to the invention are suitable for the treatment of a patient presenting with a cancer with CD127 positive tumor cells, in particular a cancer where CD127+ cell constitute a marker of poor prognosis such as in lung cancer or mesothelioma.

By "treatment" or "therapeutic treatment", it is meant that the performed steps of administration result in improving the clinical condition of an animal or a human patient in need thereof, who suffers from disorder(s) associated with the IL-7 and TSLP pathways, i.e involving the proliferation or an accumulation of CD127 positive cells or the differentiation/maturation/proliferation of cells in response to TSLP. Such treatment aims at improving the clinical status of the animal or human patient, by eliminating or alleviating the symptoms associated with the disorder(s) related to the presence of these cells, i.e; involving the proliferation and/or accumulation of CD127 positive cells or differentiation/maturation/proliferation of cells in response to TSLP, and/or in a preferred embodiment, the treatment according to the invention enables restoring to health.

The invention also relates to the use of an anti-CD127 antibody or antigen-binding fragment thereof or antigen-binding antibody mimetic as defined herein in a diagnostic test, particularly in a diagnostic test for personalized medicine, more particularly in a companion diagnostic test.

The invention also concerns an in vitro or ex vivo method of diagnosis, in particular a method of diagnostic suitable for use in personalized medicine, more particularly in a companion diagnosis, wherein an anti-CD127 antibody of the invention or an antigen-binding fragment thereof or an antigen-binding mimetic thereof is used for the detection of CD127+ cells in a sample previously obtained from a subject and optionally for the quantification of the expression of CD127.

In a particular embodiment, the invention also concerns the use of an anti-CD127 antibody of the invention or an antigen-binding fragment thereof or an antigen-binding mimetic thereof in the manufacture of a medicament suitable for use in a diagnostic test, in particular for use in personalized medicine, or in a companion diagnostic test.

In another aspect of the invention, an anti-CD127 antibody of the invention or an antigen-binding fragment thereof or an antigen-binding mimetic thereof is used in a method of in vitro or ex vivo determining the presence of CD127+ cells in a sample previously obtained from a subject.

In a particular embodiment this method comprises determining in vitro the expression and/or the level of expression of CD127, in a biological sample of said subject using the anti-human CD127 antibody or antigen-binding fragment thereof or antigen-binding antibody mimetic of the invention.

In another embodiment this method comprises determining presence of CD127 as a biomarker that is predictive for the response of a subject to a treatment, in particular a response of a subject diagnosed with a cancer wherein said method comprises:

determining the expression level of CD127 in a tumor sample of a subject, in particular with anti-CD127 antibody or antigen-binding fragment thereof or antigen-binding antibody mimetic of the invention, and comparing the expression level of CD127 to a value representative of an expression level of CD127 in a non-responding subject population, wherein a higher expression level of CD127 in the tumor sample of the subject is indicative for a subject who will respond to the treatment.

Determining the expression level according to the method may encompass quantitating the CD127 molecule on cells of the sample.

Additional features and properties of the invention will be apparent from the Examples which follow.

EXAMPLES

Examples/Materiel and Methods/Results

Humanisation

The MD707-3 clone was humanized by de-immunisation and resurfacing in silico methods as described above.

Antibody MD707-3 consist of the light chain (Sequence of SEQ ID No57 in Table 6) and Heavy chain (Sequence of SEQ ID No56 in Table 6). Analysis of the domain content of MD707-3 showed it to be an Fv, presumably from a full length IgG1 antibody. The variable domains were isolated and annotated with kabat CDR definitions and numbering. Sequence alignments comparing MD707-3 variable domains to the human germlines were generated. Based on overall sequence identity, matching interface positions and similarly classed CDR caonical positions, a germline family was identified for each chains. MD707-3 was found to be similar to the light chain germline KK2-A3 and Heavy VH3-3-73. The structural models of the Parental and the de-immunised sequences were constructed.

TABLE 1

Resurfacing residues

| Chain | Region | Substiitution | Description |
|---|---|---|---|
| L | FR1 | A7S | Conservative substitution of Alanin for Serine brings the position in line with the closest human germlines. |
| L | FR1 | L9S | Resurface protruding Leucine to Serine. Anough Leucine occurs at this position, it is a fully exposed hydrophobic residue that can be substituted |
| L | FR1 | V11L | Substitution of Valine for Leucine at position 11 is part of a large resurfacing and reshaping of FR1, including positions 12 and 18. The three substitutions will alter the surface to resemble that of the closest human germlines. Resurfacing Valine to Leucine in conjunction with Serine to Proline at position 12. |
| L | FR1 | S12P | Resurfacing Serine to Proline in conjunction with Valine to Leucine at position 11 |
| L | FR1 | S18P | Resurfacing Serine to Proline |
| L | L2 | L59R | Both Leucine and Arginine is allowed at the position. However, the most similar human germlines all have Arginine. As the position lies within CDR L2 and even though it is not involved in binding Leucine was retained in the first resurfaced chain. Arginine was evaluated in the second resurfaced chain. |
| L | FR3 | R68S | Resurface protruding foreign Arginine to Serine |
| L | FR3 | K82R | Conservative substitution of Lysine for Arginine brings the position in line with the closest human germlines. |
| L | FR3 | T85A | Conservative substitution of Threonine for Alanine brings the position in line with the closest human germlines. |
| H | FR1 | H3Q | Histidine is a foreign residue, resurface to Glutamine. |
| H | FR1 | K15G | Resurfacing foreign protruding Lysine for Glycine. Substitute in concert with Glutamic acid at position 16 for charge neutrailty. |
| H | FR1 | E16G | Resurfacing foreign protruding Glutamic acid for Glycine. Substitute in concert with Lysine at position 15 for charge neutrality. |
| H | H2 | E64D | Conservative substitution of Glutamic for Aspartic acid to bring the position in line with the closest human germlines. |
| H | FR3 | M80T | Resurface exposed hydrophobic Methionine to Threonine |
| H | FR3 | N87S | Resurface Asparagine to Serine |
| H | FR3 | D91E | Conservative substitution of Aspartic for Glutamic acid to bring the position in line with the closest human germlines. |
| H | FR3 | M95V | Resurface surface exposed Methionine to Valine. Threonine is also frequentiy found at the position. However, the closest human germlines contain Valine. |
| H | FR4 | M118L | Resurface exposed hydrophobic Methionine to Leucine. The position should be Leucine or Methionine and Leucine cannot oxidise. |

Resurfacing substitutions have been designed based on this specific context and may have a different effect if performed in some other sequence context.

TABLE 2

De-immunized substitutions

| Chain | Region | Substitution | Description |
|---|---|---|---|
| L | L1 | S28D | Substitution to Aspartic add completely removes two promiscuous epitopes. This CDR substitution is attempted due to its effectiveness at reducing predicted immonogenicity. The position is outside of the likely binding interface. The introduction os a charge here would replace the toss of the spatially close charge at position 73, L:E73G. |

TABLE 2-continued

De-immunized substitutions

| Chain | Region | Substitution | Description |
|---|---|---|---|
| L | FR2 | K47Q | De-immunising substitution of Lysine to Glutamine that removes binding for 8 HLA-DRBI allotypes. Substitution ensures retained charge neutrality when substitution Q50K is performed. |
| L | FR2 | Q50K | De-immunising substitution of Glutamine for Lysine is not that effective at reducing predicted immunogenicity but brings the domain in line with the expected set of residues in the charge cluster tocated in the VK domains lower half. The introduction of the charge is compensated for by a resurfacing substitution at position 47. |
| L | L2 | A60D | Position 60 is at the bottom of the loop, far away from the binding interface Aspartic acid is acceptable at the position and is effective at reducing predicted immunogenicity |
| L | FR3 | E73G | Position 73 is commonly glycine in human antibodies and is close to the CDRs. The Glutamic acid should be removed both for resurfacing and de-immunisation reasons. However, due to the proximity to the CDRs the substitution is only performed together with the re-introduction of a charge at the spatiafiy close position 28. The substitution removes 4 promiscuous epitopes. |
| L | FR3 | V90T | De-immunising substitution of solvent exposed Valine for Threonine. Substitution removes binding to 7 HLA-DR81 allotypes |
| H | FR1 | S21T | De-immunising substitution in FR1 which removes binding to 9 HLA-DRB1 aliotypes. |
| H | FR1 | S30T | The position is close to the binding interface. However, given the location and direction it is facing a conservative de-immunising substitution of Serine to Threonine should be evaluated. The substitution removes binding to 4 HLA-DRB1 allotypes including the common DRB1*03:01 allotype. |
| H | FR3 | M95T | Substitution from Methionine to Threonine is more effective at reducing predicted immunogenicity compared to Valine, removing binding to an additional 19 HLA-DRB1 allotypes. |
| H | H3 | V101T | Substitutions at position 101 and 102 are aimed at removing a cluster of epitopes spanning from FR3 and H3. The substitutions are effective at reducing the predicted immunogenicity, together removing binding for 26 HLA-DRB1 allotypes. Careful structural analysis has indicated that substitution to the Threonine with its similarly beta-branched ssde-cbain could be tolerated |
| H | H3 | V102T | Effective de-immunising substitution that could be tolerated. |

De-immunising substitutions have been designed based on the resurfaced sequences and may have a different effect if performed in some other sequence context.

A total of four resurfaced/de-immunised light chains and four resurfaced/de-immunised heavy chains have been proposed. 15 variants were designed and have been recommended to be expressed and characterized in vitro.

TABLE 3

| Conserved position into the VH/VL interface | |
|---|---|
| Domain | Positions |
| VL | 34, 36, 38, 43, 44, 46, 87, 88, 89, 91, 96, 98 |
| VH | 35b*, 37, 39, 45, 47, 91, 93, 95 100-100k**, 101, 103 |

All positions are according to Kabat numbering
*The numbering of the position one N-terminal to position 36 is dependent on CDR H1 length
**The numbering of the position one N-terminal to position 101 differs by CDR H3 length

TABLE 4

| Position determining CDRs canonical class | |
|---|---|
| CDR | Key Residues |
| L1 | 2, 25, 27b, 27c, 28, 33, 71 |
| L2 | 34 |
| L3 | 99, 94, 95, 97 |
| H1 | 24, 26, 29, 35a**, 94 |
| H2 | 54, 55, 71 |

All positions are according to Kabat numbering
**The numbering of the position two N-terminal to position 36 is dependent on CDR H1 length Nucleotides and Amino Acid Sequences of Anti-Human CD127 Mabs VH and VL regions of the Effi3 clone were sequenced using the RACE PCR technology. Briefly, total RNA was extracted, reverse transcribed and the resulting cDNA was poly-adenylated at the 3' end of the molecules using dATP and the terminal transferase enzyme. A first 35-cycle PCR reaction was performed using an oligodT anchor primer and Herculease enzyme (Stratagene). A second 35-cycle PCR was performed using nested PCR anchor primers. The resulting PCR product was then TA-cloned in *E. Coli* and after selection on ampicillin, resulting colonies were screened by restriction enzyme profiling and inserted cDNA sequenced Humanised Effi3 Variants were Cloned into pFuse-CHiG or pFuse-CLIg Plasmids Cloning of Sequences of Humanised Mutation of V Stability Assay Humanized Effi3 antibody (clone VH3VL4) was incubated at 4° C., 37° C., at −80° C. or at room Temperature for 28 days. The binding activity was tested by ELISA assay, recombinant hCD127 (Sino Biologicals, Beijing, China; reference 10975-H08H) was immobilized on plastic at 1 µg/ml and dilutions of supernatant were added to measure binding. After incubation and washing, mouse anti-human light chain (kappa specific) plus peroxidase-labeled donkey anti-mouse antibodies were added and revealed by conventional methods. Increase doses of Mabs were added to measure binding. After incubation and washing, peroxidase-labeled mouse anti-rat kappa chain (AbdSerotec) was added and revealed by conventional methods.

Figure 1B:
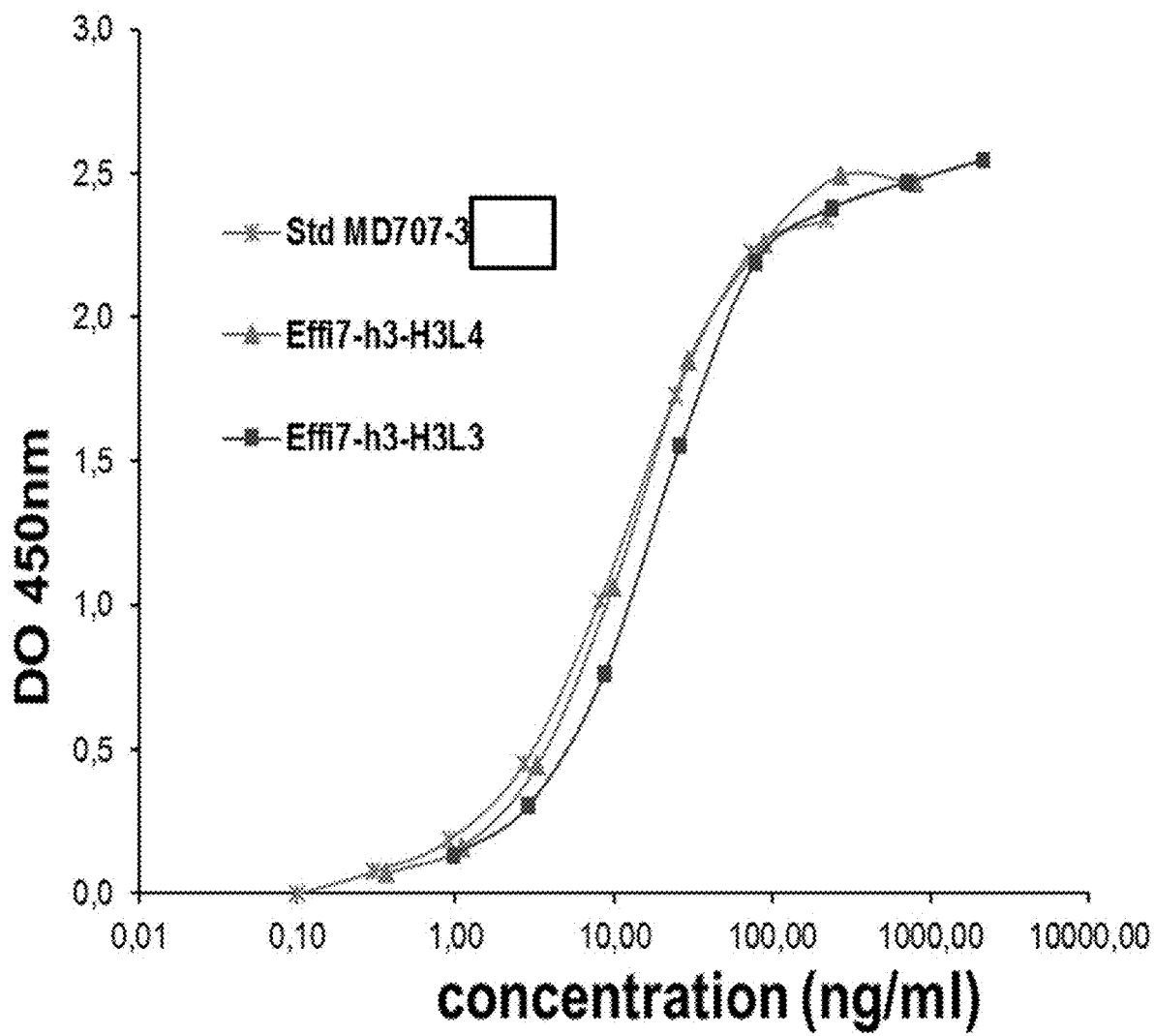
Figure 2:
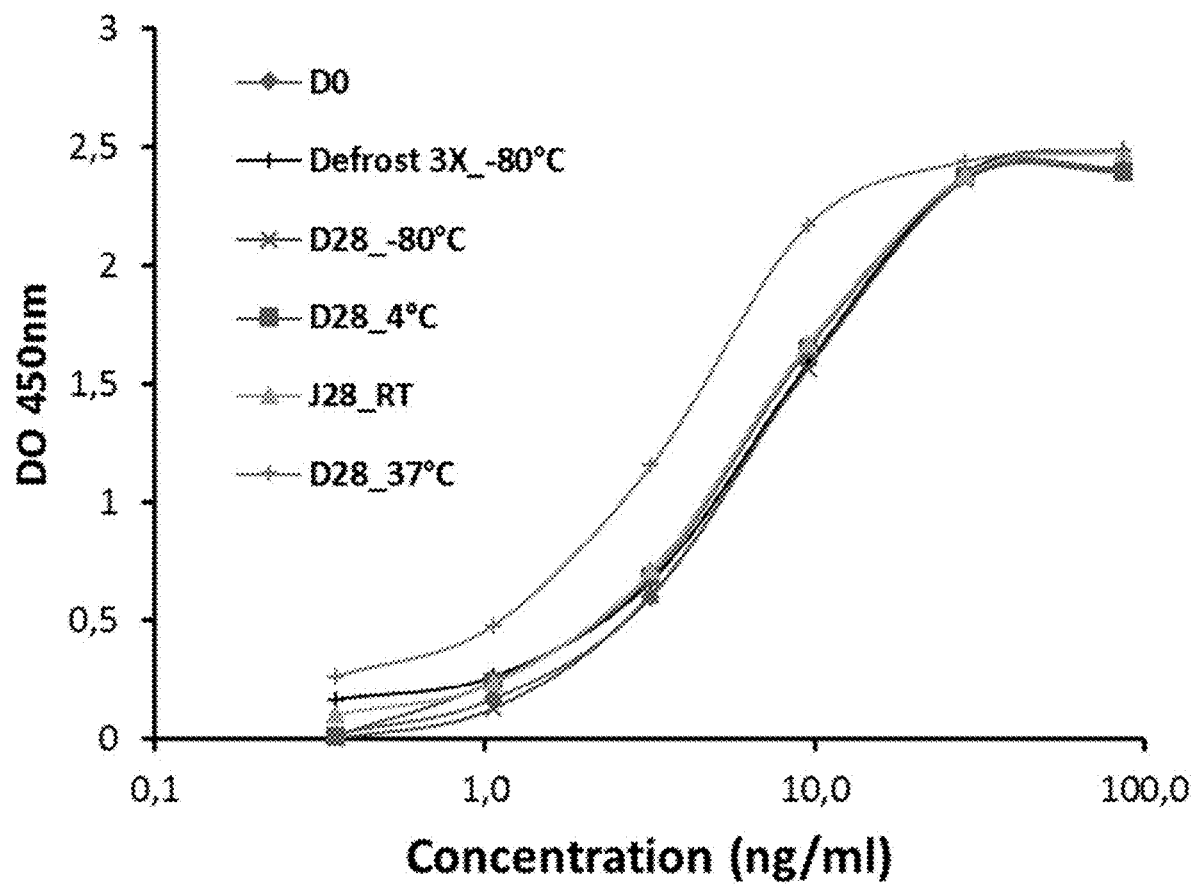

Results FIG. 1 B. show that purified Effi3 is stable over time and after different temperatures of storage.

Phospho Stat5 Activity Assay

Human peripheral blood monocytic cells (PBMC) harvested by ficoll gradient from healthy volunteers were incubated in serum-free media with different concentration of antibodies of interest for 15 minutes at room temperature, before incubation with 0.1 or 5 ng/ml of recombinant human IL-7 (rhIL-7; AbD Serotec ref PHP046) for 15 minutes at 37° C. PBMC untreated with rhIL-7 were analyzed as the background signal, while IL-7 treated cells without antibody were set as negative control. PBMC were then quickly chilled and washed with FACS buffer to stop the reaction. Cells were then incubated for 15 minutes with cold Cytofix/Cytoperm solution (BD Bioscience, ref 554722), washed twice with Perm/Wash buffer (Bd Bioscience) and stained with an anti-human CD3 FITC antibody (Bd Bioscience ref 557694) for 30 minutes on ice. PBMC were then washed twice with Perm/Wash buffer and permeabilized in BD Perm Buffer III (Bd Bioscience, ref 558050) for 30 minutes. Cells were then washed twice in FACS buffer (and/or PBS with 1% BSA and 0.1% azide) and incubated for 30 minutes at room temperature with anti-human pSTAT5 Alexa 647 antibody (BD Bioscience, ref 612599). Samples were analyzed on BD CANTO II FACS instrument. As shown in FIG. 3 A., Effi3 antibody (variant VH3VL4) derived from the MD707-3 antibody, has no more inhibitory activity of STAT5 phosphorylation compare to the parent antibody MD707-3.

TARC Secretion Assay Myeloid dendritic cells (DC) were isolated with CD1c (BDCA-1)+ Dendritic cell isolation kit (Miltenyi Biotec, Bergisch Gladbach, Germany) from blood of healthy volunteers (Etablissement Français du Sang, Nantes, France). Myeloid dendritic cells were cultured in RPMI containing 10% fetal calf serum, 1% pyruvate, 1% Hepes, 1% L-glutamine and 1% penicillin-streptomycin. Cells were seeded at 5.104 cells/well in flat-96-well plates, in the presence of TSLP (15 ng/ml), LPS (1 µg/ml) or culture medium alone, and addition of different human CD127 antibodies (MD707-3, Effi3-VH3VL4) or anti-TSLP antibody at different concentrations. At 24 hours of culture, supernatants were collected and analyzed for TARC production by ELISA assay (R&D sytems, Minneapolis, USA).

The inhibition of TSLP-induced production of TARC was assessed by measuring said production as described above in the absence of antibody or in the presence of MD707-3 or Effi3 or commercial anti-TSLPR antibody (R&Dsystems ref. AF981) at 0.2, 1, 5 or 25 µg/ml. As shown in 3 B., Effi3 did not anymore inhibit TSLP-induced TARC production compare to its parent antibody MD707-3 and the positive control anti-TSLP antibody.

Antibody-Dependent Cellular Cytotoxicity (ADCC)

ADCC of anti-human CD127 Mabs ADCC refers to as the binding of an antibody to an epitope expressed on target cells and the subsequent Fc-dependent recruitment of effector immune cells expressing Fc receptors (essentially NK cells and activated lymphocytes), resulting in the killing of target cells mainly by granzyme/perforin-based mechanisms.

For use of the antibody in its original (rat) format, the effectors cells were rat Lymphokine-Activated Killer (LAK) cells generated from spleen cells cultured with 1000 UI/ml of IL-2 (Roche, Basel, Switzerland) in tissue culture flasks (Corning Glass Works, Corning, N.Y.).

When antibody was humanized, the effector cells were fresh primary human NK cells isolated from peripheral blood mononuclear cells by negative selection using magnetic beads (NK isolation kit, Miltenyi Biotec, Bergisch Gladbach, Germany) using an AutoMACS cell sorting instrument. NK cells were incubated over-night at 37° C., 5% CO2, in RPMI 1640 Medium (Life Technologies, Carlsbad, Calif.) complemented with 10% FBS (Life Technologies), 100 IU/ml penicillin (Life Technologies), 0.1 mg/ml streptomycin (Life Technologies), 2 mM L-glutamine (Life Technologies) and 150 IU/ml of human IL-2 (Roche, Basel, Switzerland).

The target cells were labeled with 100 µCi (3.7 MBq) of 51Cr (PerkinElmer) for 1 h at 37° C. and washed three times with culture medium. Target cells were incubated with diluted antibodies or with excipient (culture medium) for 15 min at room temperature and 10 000 cells were placed in a 96-well U-bottom plate. Effector T cells were added at the indicated E:T (effector:target) cell ratio (final volume: 200 µl) for a 4 hours incubation period at 37° C. A total of 25 µl of the supernatant was then harvested and counted in a gamma counter (Packard Instrument). Percentage of specific cytotoxicity was determined by 51Cr release.

Figure 4:
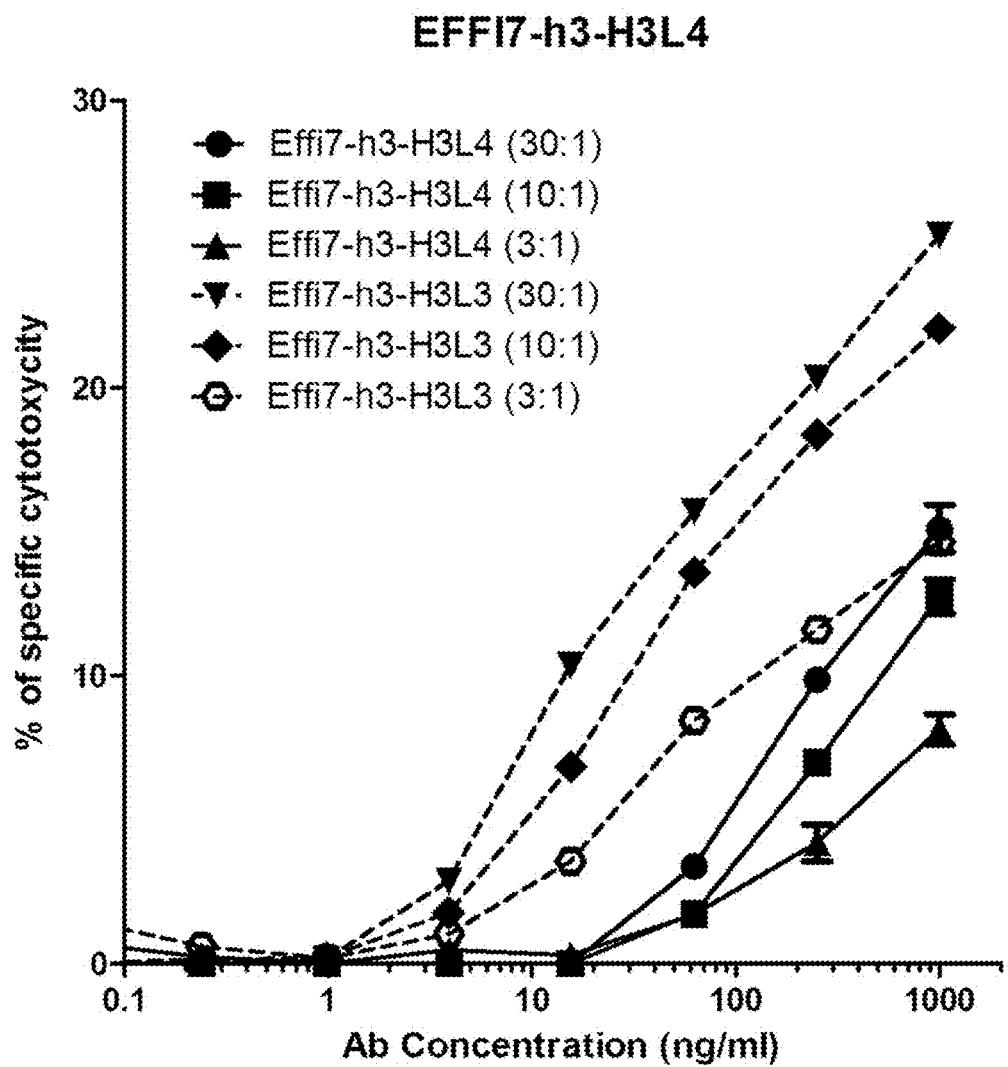

The results presented FIG. 4, shows that Effi3 H3L4 and H3L3 variant antibodies induced ADCC, in dose-dependent manner.

Antibody Profiling Using Peptide Microarray

The peptide Technologies PepStar™ peptide microarrays comprise purified synthetic peptides derived from antigens or other sources that are chemoselectively and covalently immobilized on a glass surface. An optimized hydrophilic linker moiety is inserted between the glass surface and the antigen-derived peptide sequence to avoid false negatives caused by sterical hindrance. For technical reasons all peptides contain a C-terminal glycine. Profiling experiments of samples were performed on a peptide library consisting of 52 peptides. The complete list of peptides is shown below:

TABLE 5

List of peptides used in peptide microarray assays

| Nb | Sequence |
|---|---|
| 58 | ESGYAQNGDLEDAEL |
| 59 | AQNGDLEDAELDDYS |
| 60 | DLEDAELDDYSFSCY |
| 61 | AELDDYSFSCYSQLE |
| 62 | DYSFSCYSQLEVNGS |
| 63 | SCYSQLEVNGSQHSL |

TABLE 5-continued

List of peptides used in peptide microarray assays

| Nb | Sequence |
|---|---|
| 64 | QLEVNGSQHSLTCAF |
| 65 | NGSQHSLTCAFEDPD |
| 66 | HSLTCAFEDPDVNTT |
| 67 | CAFEDPDVNTTNLEF |
| 68 | DPDVNTTNLEFEICG |
| 69 | NTTNLEFEICGALVE |
| 70 | LEFEICGALVEVKCL |
| 71 | ICGALVEVKCLNFRK |
| 72 | LVEVKCLNFRKLQEI |
| 73 | KCLNFRKLQEIYFIE |
| 74 | FRKLQEIYFIETKKF |
| 75 | QEIYFIETKKFLLIG |
| 76 | FIETKKFLLIGKSNI |
| 77 | KKFLLIGKSNICVKV |
| 78 | LIGKSNICVKVGEKS |
| 79 | SNICVKVGEKSLTCK |
| 80 | VKVGEKSLTCKKIDL |
| 81 | EKSLTCKKIDLTTIV |
| 82 | TCKKIDLTTIVKPEA |
| 83 | IDLTTIVKPEAPFDL |
| 84 | TIVKPEAPFDLSVIY |
| 85 | PEAPFDLSVIYREGA |
| 86 | FDLSVIYREGANDFV |
| 87 | VIYREGANDFVVTFN |
| 88 | EGANDFVVTFNTSHL |
| 89 | DFVVTFNTSHLQKKY |
| 90 | TFNTSHLQKKYVKVL |
| 91 | SHLQKKYVKVLMHDV |
| 92 | KKYVKVLMHDVAYRQ |
| 93 | KVLMHDVAYRQEKDE |
| 94 | HDVAYRQEKDENKWT |
| 95 | YRQEKDENKWTHVNL |
| 96 | KDENKWTHVNLSSTK |
| 97 | KWTHVNLSSTKLTLL |
| 98 | VNLSSTKLTLLQRKL |
| 99 | STKLTLLQRKLQPAA |
| 100 | TLLQRKLQPAAMYEI |
| 101 | RKLQPAAMYEIKVRS |
| 102 | PAAMYEIKVRSIPDH |
| 103 | YEIKVRSIPDHYFKG |
| 104 | VRSIPDHYFKGFWSE |
| 105 | PDHYFKGFWSEWSPS |
| 106 | FKGFWSEWSPSYYFR |
| 107 | WSEWSPSYYFRTPEI |
| 108 | SPSYYFRTPEINNSS |
| 109 | YFRTPEINNSSGEMD |

A total of 9 samples were incubated on microarray slides using a Multiwell-format. For N13B2 antibody and the other samples, 4 different concentrations were applied (10, 1, 0.1 et 0.01 µg/ml). One negative control incubation (secondary antibody only) was performed in parallel. Human and mouse IgG proteins were co-immobilized alongside each set of peptides to serve as assay controls. All incubations were performed in parallel using two slides. Two peptide-mini-arrays on each slide were used as a control incubation by applying the fluorescence labelled detection antibody alone to assess false-positive binding to the peptides. After washing and drying of the slides they were scanned with a high-resolution laser scanner at 635 nm to obtain images of fluorescence intensities. The images were quantified to yield a mean pixel value for each peptide. Secondary antibody anti-rat IgG (JIR 212-175-082) labeled with Cy5 at 1 µg/ml. Buffers and solutions The buffer used were TBS-buffer including 0.05% Tween20 (JPT) and Assay buffer T20 (Pierce, SuperBlock TBS T20, #37536). Acquisition and analysis were performed using Peptide microarrays (JPT Peptide Technologies GmbH, Berlin, Germany; batch #2668, Multi-Well incubation chamber, Axon Genepix Scanner 4200AL, Spot-recognition software GenePix and Microsoft Excel.

Result presented FIG. 5 show the sequence of the linear epitope that is recognized by the Effi3 antibody on CD127.

The following table (Table 6) discloses the sequence described herein. "Nb" stands for the SEQ ID NO of each sequence; "Type" discloses the nature of the sequence, either DNA or amino acid sequence (PRT) and "len" stands for the length of the sequence.

| Nb | Name | Type | Sequence | Len |
|---|---|---|---|---|
| 1 | Effi3 VHvar3 | DNA | GCTGTGCAGCTGGTCGAATCTGGGGGGGGCTGGTCCAGCCTGGGGGGTCTCTGAAAATCACTTGCGCCGCTAGTGGTT CACCTTTACAAACGCAGCCATGTACTACAACTTACTATGCCGACTCAGTGAAGGGCCAGGTCACCATTAGCCGCGACAGATAGCAATCA AAGGCTAACAACTACCGACATGGACTCTGTGAAGACAGAGATACTGCCACCTACTATTGTATTGTGCTGCTGACTACTACAC CAGTCTACCTGCCAGATGGACTCTGTGAAGACAGAGATACTGCCACCTACTATTGTATTGTGCTGCTGACTACTACAC GGGATTACTTTGACTATTGGGGACAGGGAGTCGTGACAGTGAGTTCA | 369 |
| 2 | Effi3 VHvar3_aa | PRT | AVQLVESGGGLVQPGGSLKITCAASGFTFTNAAMYWVRQAPGKGLEWVARIRTKANNYATYYADSVKGRFTISRDDSKSTV YLQMDSVKTEDTATYYCIVVVLTTTRDYFDYWGQGVLVTVSS | 123 |
| 3 | Effi3 VLvar3 | DNA | GACATCGTCCTCGACTCAGTCCCCTCTTCCCTGCCAGTGACACCTGGAGAGCCAGCATCTATCAGTTGCCGAAGCTCCAG TCACTGCTGACTGTCAAGGAATTACCAGCCTGTACTGGTTCTGCAGAGCGCCGGTCCAGTCCCTAAACTGCTGATCTAT CGGATGTCTAACAGAGACAGTGGGGTTGCCGATAGGTTCAGCGGCAGCGGGTCTGGGACAGTCTTCGCACAGTTTCTGCACATGCCGAACCCCTCAGCATTTCGGGGGCAGGCACT CTCGCGTGGAGGCTGAAGATGTCGGAACCTACTATTGCGCACAGTTTCTGGAATACCCTCACACTTTCGGGGGCAGGCACT AAGCTGAGCTGAAGCGT | 339 |
| 4 | Effi3 VLvar3_aa | PRT | DIVLTQSPSSLPVTPGEPASISCRSSQSLLTVKGITSLYWFLQKPGQSPKWYRMSNRDSGVPDRFSGSGSETDFTLKISRVEAED VGTYYCAQFLEYPHTFGAGTKLELKR | 113 |
| 5 | Effi3-VLvar4 | DNA | GACATCGTGCTGACACAGAGTCCCCTCTGCACAGAGTCCCTGCAGTGACACCTGGTTCTCGAGAGCCAGCATCTATCAGTTGCCGAAGCTCCA ATCGGATGTCTAACAGAGACAGTGAGTGCCGATAGGTTCCGACGATGGGTGGCACGAATCCAGAACCAGTCAACAACTACGCAACTTACTAT TTCTGCGTGGAGGCTGAAGATGTCGGAACCTACTATTGCGCACAGTTTCTGGAGTATCCCCACACTTTGGAGCAGGCAC TAAGCTGGAGCTGAAGCGT | 339 |
| 6 | Effi3-VLvar4_aa | PRT | DIVLTQSPSSLPVTPGEPASISCRSSQDLLTVKGITSLYWFLQKPGQSPKWYRMSNRDSGVPDRFSGSGSETDFTLKISRVEAE DVGTYYCAQFLEYPHTFGAGTKLELKR | 113 |
| 7 | Effi3 VHvar3 (+signal peptide) | DNA | ATGCTGGTCCTGCAGTGGGTCCTGGTCACCGCTCTGTTCCAGGGGGTCCACTGTGCCGTGCAGCTGGTCGAATCTGGGGGG GGGCTTGTCCAGCCCGGCGGGTCTCTGAAAATCACTTGCGCCGCTAGTGGTTCACCTTTACAAACGCAGCCATGTACTG GTCTCGACAGGCCTCCTGGAAAGGGCCTAGTGGGTGGCACGAGATCAGAACAAAGCTAACAACTACGCAACTTACTAT GCCGACTCAGTGAAGGGCAGGTTCACCATTAGCCGCGACGATAGCAAATCCACAGTCTACCTGCAGATGACTCTGTGA AGACAGAAGATACTGCCACCTACTATTGTATTGTGCGTGCTGGACTACTACACGGGATTACTTTGACTATTGGGGACAG GGAGTCGTGGACAGTGAGTTCA | 423 |
| 8 | Effi3 VHvar3_aa (+signal peptide) | PRT | MLVLQWVLVTALFQGVHCAVQLVESGGGLVQPGGSLKITCAASGFTFTNAAMYWVRQAPGKGLEWVARIRTKANNYATYY ADSVKGRFTISRDDSKSTVYLQMDSVKTEDTATYYCIVVVLTTTRDYFDYWGQGVLVTVSS | 141 |
| 9 | Effi3 VLvar3 (+signal peptide) | DNA | ATGAAGTTCTCTGCTCAGTTTCTGGGCTGCTCAGTTTCTGGGGCTGCTGTTCTGTGTATTCTGCCGGCTCAGGTGAGACATCGTCCTGACTCAGTCCC CCCTCTTCCCTGCCAGTGACACCCTGGAGAGCCAGCATCTATCAGTTGCCGAAGCTCCTGACTGTCAAGGGA ATTACCAGCCTGTACTGGTTCCTGCAGAGCAGCGGGTCCAGTCCCTAAACTGCTGATCTATCGGATGTCTAACAGAGACAG TGGGGGTTGCCGATAGGTTCAGCGGCAGCGGGTCTGGGACAGTCTTCGCACTGAAAATTCTCGCGTGGAGGCTGAAGATG TCGGAACCTACTATTGCGCACAGTTTCTGGAATACCCTCACACTTTCGGGGGCAGGCACTAAGCTGGAGCTGAAGCGT | 399 |
| 10 | Effi3 VLvar3_aa (+signal peptide) | PRT | MKFPAQFLGLLVLCIPGATGDIVLTQSPSSLPVTPGEPASISCRSSQSLLTVKGITSLYWFLQKPGQSPKWYRMSNRDSGVPDR FSGSGSETDFTLKISRVEAEDVGTYYCAQFLEYPHTFGAGTKLELKR | 133 |

| Nb | Name | Type | Sequence | Len |
|---|---|---|---|---|
| 11 | Effi3-VLvar4 (+signal peptide) | DNA | ATGAAGTTCCCTGCTCAGTTCCTGGGACTCCTGTGCTGTTCCTGTGCATTCAGTGACACAGGCAACCGGCACATCTGCTGACTGTCAAGAG CCCTCCTCCACTCACTGGTTCCTGCAGAAGCCCGGCAGCCCTAAACTGCTGATCTATCGGATGTCTAACAGACAGA CATTACCTCACTCACTGGTTCCTGCAGAAGCCCGGCAGCCCTAAACTGCTGATCTATCGGATGTCTAACAGACAGA GTGGAGTGCCCGATAGGTTCTCAGGCAGCGGGCTCAGGAACAGACTTTCACACTGAAAATTTCTGCGTGGAGCTGAAGAT GTCGGCACCTACTATTGCGCACAGTTTCTGGAGTATCCCCACACTTTGGAGCAGGCACTAAGCTGAAGCTGAAAGCT | 399 |
| 12 | Effi3-VLvar4_aa (+signal peptide) | PRT | MKFPAQFLGLLLCCSCIRDTQAQFLGLVLCIPGATGDIVLTQSPSSLPVTPGEPASISCRSSQDLLTVKGITSLYWFLQKPGQSPKLLIYRMSNRDSGVPDRFSGSGSGTDFTLKISRVEAEDVGTYYCAQFLEYPHTFGAGTKLELKR | 133 |
| 13 | Effi3 VHvar3_CDR1 | DNA | TTCACCTTTACAAACGCAGCCATGTAC | 27 |
| 14 | Effi3 VHvar3_CDR1-aa | PRT | FTFTNAAMY | 9 |
| 15 | Effi3 VHvar3_CDR2 | DNA | CGGATCAGAACAAAGGCTAACAACTACGCAACTTACTATGCCGACTCAGTGAAGGGC | 57 |
| 16 | Effi3 VHvar3_CDR2-aa | PRT | RIRTKANNYATYYADSVKG | 19 |
| 17 | Effi3 VHvar3_CDR3 | DNA | GTCGTGCTGACTACTACACGGGATTACTTTGACTAT | 36 |
| 18 | Effi3 VHvar3_CDR3-aa | PRT | VVLTTTRDYFDY | 12 |
| 19 | Effi3 VLvar3_CDR1 | DNA | CGAAGCTCCCAGTCACTGCTGACTGTCAAGGGAATTACCAGCCTGTAC | 48 |
| 20 | Effi3 VLvar3-CDR1_aa | PRT | RSSQSLLTVKGITSLY | 16 |
| 21 | Effi3 VLvar3/4_CDR2 | DNA | CGGATGTCTAACAGAGACAGT | 21 |
| 22 | Effi3 VLvar3/4_CDR2aa | PRT | RMSNRDS | 7 |
| 23 | Effi3 VLvar3/4_CDR3 | DNA | GCACAGTTTCTGGAATACCCTCACACT | 27 |
| 24 | Effi3 VLvar3/4_CDR3aa | PRT | AQFLEYPHT | 9 |
| 25 | Effi3-VLvar4_CDR1 | DNA | CGAAGCTCCCAGGACCTGCTGACTGTCAAGGGCATTACCTCACTGTAC | 48 |
| 26 | Effi3-VLvar4_CDR1_aa | PRT | RSSQDLLTVKGITSLY | 16 |
| 27 | IgG1m (E333A) | DNA | GCTAGCACCAAGGGCCCATCCGTCTTCCCCCTGGCACCCTCCTCCAAGAGCACCTCTGGGGGCACAGCGGCCCTGGGCTG CCTGGTCAAGGACTACTTCCCCGAACTGGTGACGGTGTCGTGGAACTCAGGCGCCCTGACCAGCGGCGTGCACACCTTCC CGGCTGTCCTACAGTCCTCAGGACTCTACTCCCTCAGCAGCGTGGTGACCGTGCCCTCCAGCAGCTTGGGCACCCAGACCT ACATCTGCAACGTGAATCACAAGCCCAGCAACACCAAGGTGGACAAGAAAGTTGAGCCCAAATCTTGTGACAAAACTCA CACATGCCCACCGTGCCCAGCACCTGAACTCCTGGGGGGACCGTCAGTCTTCCTCTTCCCCCCAAAACCCAAGGACACCC TCATGATCTCCCGGACCCCTGAGGTCACATGCGTGGTGGTGGACGTGAGCCACGAAGACCCTGAGGTCAAGTTCAACTGG TACGTGGACGGCGTGGAGGTGCATAATGCCAAGACAAAGCCGCGGGAGGAGCAGTACAACAGCACGTACCGTGTGGTC AGCGTCCTCACCGTCCTGCACCAGGACTGGCTGAATGGCAAGGAGTACAAGTGCAAGGTCTCCAACAAAGCCCTCCCAG CCCCCATCGAGAAAACCATCTCCAAAGCCAAAGGGCAGCCCCGAGAACCACAGGTGTACACCCTGCCCCCATCCCGGGA GGAGATGACCAAGAACCAGGTCAGCCTGACCTGCCTGGTCAAAGGCTTCTATCCCAGCGACATCGCCGTGGAGTGGGAG AGCAATGGGCAGCCGGAGAACAACTACAAGACCACGCCTCCCGTGCTGGACTCCGACGGCTCCTTCTTCCTCTACAGCAA GCTCACCGTGGACAAGAGCAGGTGGCAGCAGGGGGAACGTCTTCTCATGCTCCGTGATGCATGAGGCTCTGCACAACCAC TACACGCAGAAGAGCCTCTCCCTGTCTCCGGGTAAATGA | 993 |

| Nb | Name | Type | Sequence | Len |
|---|---|---|---|---|
| 28 | IgG1m(E333A)_aa | PRT | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIAKTISKAKGQPREPQVYTLPPSREEMTKNQVSLTCLVKGFYPSDIAVEWESNGQPENNYKTTPPVLDSDGSFELYSKLTVDKSRWQQGNVFSCSVMHEALHNHYTQKSLSLSPGK | 330 |
| 29 | IgG4m(S228P) | DNA | GCTAGCACCAAGGGCCCATCTTCCCCCTGGCCCCTGCTCTCCAAGGAGCACCTCTGGGCTGCCTGGTCAAGGACTACTTCCCCGAACCGGTGACGGTGTCGTGGAACTCAGGCGCTCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACGAAGACCTACACCTGCAACGTAGATCACAAGCCCAGCAACACCAAGGTGGACAAGAGAGTTGAGTCCAAATCTTGTGACAAAACTCACACATGCCCACCGTGCCCAGCACCTGAGTTCCTGGGGGGACCATCAGTCTTCCTGTTCCCCCCAAAACCCAAGGACACCCTCATGATCTCCCGGACCCCTGAGGTCACGTGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTACCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAATGA | 984 |
| 30 | IgG4m(S228P)_aa | PRT | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 327 |
| 31 | IgG2b | DNA | GCTAGCACCAAGGGCCCATCGGTCTTCCCCCTGGCGCCCTGCTCCAGGAGCACCTCCGAGAGCACAGCGGCCCTGGGCTGCCTGGTCAAGGACTACTTCCCCGAACCGGTGACGGTGTCGTGGAACTCAGGCGCTCTGACCAGCGGCGTGCACACCTTCCCAGCTGTCCTACAGTCCTCAGGACTCTACTCCCTCAGCAGCGTGGTGACCGTGCCCTCCAGCAACTTCGGCACCCAGACCTACACCTGCAACGTAGATCACAAGCCCAGCAACACCAAGGTGGACAAGACAGTTGAGCGCAAATGTTGTGTCGAGTGCCCACCGTGCCCAGCACCACCTGTGGCAGGACCGTCAGTCTTCCTCTTCCCCCCAAAACCCAAGGACACCCTCATGATCTCCCGGACCCCTGAGGTCACGTGCGTGGTGGTGGACGTGAGCCACGAAGACCCCGAGGTCCAGTTCAACTGGTACGTGGACGGCGTGGAGGTGCATAATGCCAAGACAAAGCCACGGGAGGAGCAGTTCAACAGCACGTTCCGTGTGGTCAGCGTCCTCACCGTTGTGCACCAGGACTGGCTGAACGGCAAGGAGTACAAGTGCAAGGTCTCCAACAAAGGCCTCCCAGCCCCCATCGAGAAAACCATCTCCAAAACCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTACCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCCGGCTAACCGTGGACAAGAGCAGGTGGCAGGAGGGGAATGTCTTCTCATGCTCCGTGATGCATGAGGCTCTGCACAACCACTACACGCAGAAGAGCCTCTCCCTGTCTCTGGGTAAATGA | 981 |
| 32 | IgG2b_aa | PRT | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVLHQDWLNGKEYKCKVSNKGLPAPIEKTISKTKGQPREPQVYTLPPSREEMTKNQVSLSPGKGFYPSDIAVEWESNGQPENNYKTTPPMLDSDGSFFLYSKLTVDKSRWQQGNVFSCSVMHEALHNHYTQKSLSLSPGK | 326 |
| 33 | CLkappa | DNA | ACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTAG | 321 |

-continued

| Nb | Name | Type | Sequence | Len |
|---|---|---|---|---|
| 34 | CLkappa_aa | PRT | TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 106 |
| 35 | CLlambda | DNA | GGTCAGCCCAAGGCTGCCCCCTCGGTCACTCTGTTCCCGCCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTATCTGAGCCTGACGCCTGAGCAGTGGAAGTCCCACAGAAGCTACAGCTGCCAGGTCACGCATGAAGGGAGCACCGTGGAGAAGACAGTGGCCCCTACAGAATGTTCATAG | 321 |
| 36 | CLlambda_aa | PRT | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 106 |
| 37 | HumanFc_IgG1 (UniprotP01857) | PRT | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFELYSKLTVDKSRWQQGNVFSCSVMHEALHNHYTQKSLSLSPGK | 330 |
| 38 | HumanFc_IgG4 (UniprotP01861) | PRT | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 327 |
| 39 | human CD127aa | PRT | MTILGTTFGMVFSLLQVVSGESGYAQNGDLEDAELDDYSFSCYSQLEVNGSQHSLTCAFEDPDVNTTNLEFEICGALVEVKCLNFRKLQEIYFIETKKFLLIGKSNICVKVGEKSLTCKKIDLTTIVKPEAPFDLSVIYREGANDFVVTFNTSHLQKKVKLMHDVAYRQEKDENKWTHVNLSSTKLTLLQRKLQPAAMYEIKVRSIPDHYFKGFWSEWSPSYYFRTPEINNSSGEMDPILLTISILSFFVALLVILACVLWKKRIKPIVWPSLPDHKKTLEHLCKPRKNLNVSFNPESFLDCQIHRVDDIQARDEVEGFLQDTFPQQLEESEKQRLGGDVQSPNCPSEDVVITPESFGRDSSLTCLAGNVSACDAPILSSSRSLDCRESGKNPHVYQDLLLSLGTTNSTLPPPSLQSGILTLNPVAQGQPILTSLGSNQEEAVVTMSSFYQNQ | 459 |
| 40 | human CD127_21-239 aa | PRT | ESGYAQNGDLEDAELDDYSFSCYSQLEVNGSQHSLTCAFEDPDVNTTNLEFEICGALVEVKCLNERKLQEIYFIETKKELLIGKSNICVKVGEKSLTCKKIDLTTIVKPEAPFDLSVIYRFGANDFVVTENTSHLQKKVKVLMHDVAYRQEKDENKWTHVNLSSTKLTLLQRKLQPAAMYEIKVRSIPDHYFKGEWSEWSPSYYFRTPEINNSSGEMD | 219 |
| 41 | Effi3_VH3_IgG1m(E333A) | DNA | ATGCTGTCTGTCCTGCAGTGGGTCCTGGTCACCCGCTCTGTTTCAGGGGGTCCATTGTGCTGTGCAGCTGGTCGTGCAGCTGTGTCAGCAGCGGGCTCCTGGAAAGGGCCTGGAGTGCCCACAGATACAAGACGAACGCAGCCATGCTACTATGCTGACCAGACGCTCGTGCAGGTCTCAGTGCAGGGCAGGTTCACCATCAGCCGGGACAATGCCAAGAACACTCTGTACCTGCAGATGAACAGCCTGCGAGCCGAGGACACAGCCGTGTATTACTGTGCGAGAGACATATGCGCACCTATTATGTAGTAGTAGTAGTGACAGGGAGTCTGGTGACAGTGGACACCACGTTCAGCTGAGCCTGGGGCTGCACACCTTTCCCGGCTGTCCTACAGTGTCCTGGAACTCAGGCGCCCTGACCAGCGGCGTGCACACCTTCCCAGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTGGAGCCCAAATCTGTGACAAACCCACCCTCATGATCTCCCGGACCCCTGAGGTCACATGCGTGGTGGTGGACGTGAGCCACGAAGACCCTGAGGTCAAGTTCAATTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGCGGAGAGTGACCAAGACCAAGGGCAGCCCCGAGAACCACAGGTGTACACCCTGCCCCCATCCCGGGAGGAGATGACCAAGAACCAGGTCAGCCTGACCTGCCTGGTCAGTCTTCCTGTACCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAAGGCTTCTATCC | 1416 |

| Nb | Name | Type | Sequence | Len |
|---|---|---|---|---|
| | | | CAGGACATCGCCGTGGAGTGGGAGAGCAAGCTGACCGAGCAACAACTACAAGACCACGCCTCCGTGCTGACTC CGACGGCTCCTTCTTCCTCTACACGAACGTCTTCATGCTCCG TGATGCATGAGGCTCTGCACAACTACACGCAGAAGAGCCTCTCCCTGTCTCCGGGTAAATGA | |
| 42 | Effi3_VH3_IgG1m(E333A)_aa | PRT | MLVLQWNVLVTALFQGVHCAVQLVESGGGLVQPGGSLKITCAASGFTFTNAAMYWVRQAPGKLEWVARIRTKANNYATYY ADSVKGRFTISRDDSKSTVYLQMDSVKTEDTATYYCIVVLTTTRDYFDYWGQGVLVTVSSASTKGPSVFPLAPSSKSTSGTA ALGCLVKDYFPEPVTVSWNSGALTSGVHTFPAVLQSSGLYSLSSVVTVPSSLGTQTYICNVNHKPSNTKVDKKVEPKSCDKT HTCPPCPAPELLGGPSVFLFPPKPKDTLMISRTPEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNHYTQKSLSLSPGK | 471 |
| 43 | Effi3_VH3_IgG4(S228P) | DNA | ATGCTGGTCCTGCAGTGGGTCCTGGTCACCGCTCTGTTTCAGGGGGTCCATTGTGCTGTCCAGCTGGTCGAATCTGGGGGG GGTCTGGTCCAGCCCGGCGGTTCTCTGAAAATCACTTGCGCCGCTAGTGGGTTCACCTTTACAAACGCAGCCATGTACTG GTCCCGACAGGCTCCTGGAAAGGCCTGGAGTGGGTCGCCCGGATAAGCCAAATCACAGTCTACCTGCAGATGGACTCTGTGA GCCGACTCAGTG AAGGGCCAGGTTCACCATTGTATTGTGATCTGACTACAGTCGATCTACACGGATTACTTTGACTATTGGGGACAG AGACAGAAGATACTGCAGTGACAGTGAGTTCAGCTAGCAACGGGATCCACACCTCTGGGGTGCACACCTTTCCAGCTGTC CGAGAGCACAAGACCTATACACTCTCCAGCAGTGTTGGTGACCGTGTCCTCCAGCTCAGCAGCTACCAGGGTGGACAAGAGTT CTGACCAGCAGCTTGGGACGACAATGCTCCCCATGCGAAGACACGAAGCCAGCAACTCAGTTCTGGGGGACACCATCAGT CTGCTTCAAGGAGACAACTGTGAGGGGACGAGAAGTAACCCGCCAAGACAAGCCGGCCCCGCCAGAGAGAGAGAAGTCAAC AGGTCCAGTTACCCGTGTGTCAGGTGTCCTCCGCCCACCGAGAAACCATCTCACAGGACGTGCATAATGCCAAGACAAAG GCAACAAACCGCCAAGGACAGTGCAGCCAAGGAGAGCACAAAAGCCAAAGGGCAGCCCCGAGAACCACAAGTGTACC CTGCCCCCATCCCAAGGAGGAGATGACCAAGAACCAGGTCAGCCTGACCTGCCTGGTCAAAGGCTTCTACCCAAGCGACA TCGCCGTGGAGTGGGAGAGCAATGGGCAGCCGGAGAACAACTACAAGACCACACCTCCCGTGCTGGACTCCGACGGCTC CTTCTTCCTCTACAGCAGGCTAACCGTGGACAAGAGCAGGTGGCAGGAGGGGAATGCTTCTTCTCATGCTCCGTGATGCATG AGGCTCTGCACAACCACTACACACAGAAGAGCCTCTCCCTGTCTCCGGGTAAATGA | 1407 |
| 44 | Effi3_VH3_IgG4(S228P)_aa | PRT | MLVLQWNVLVTALFQGVHCAVQLVESGGGLVQPGGSLKITCAASGFTFTNAAMYWVRQAPGKLEWVARIRTKANNYATYY ADSVKGRFTISRDDSKSTVYLQMDSVKTEDTATYYCIVVLTTTRDYFDYWGQGVLVTVSSASTKGPSVFPLAPCSRSTSESTA ALGCLVKDYFPEPVTVSWNSGALTSGVHTFPAVLQSSGLYSLSSVVTVPSSLGTKTYTCNVDHKPSNTKVDKRVESKYGPPC PPCPAPEFLGGPSVFLFPPKPKDTLMISRTPEVTCVVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSLSLSPGK | 468 |
| 45 | Effi3_VH3_IgG2b | DNA | ATGCTGGTCCTGCAGTGGGTCCTGGTCACCGCTCTGTTTCAGGGGGTCCATTGTGCTGTCCAGCTGGTCGAATCTGGGGGG GGTCTGGTCCAGCCCGGCGGTTCTCTGAAAATCACTTGCGCCGCTAGTGGGTTCACCTTTACAAACGCAGCCATGTACTG GTCCGACAGGCTCCTGGAAAGGCCTGGAGTGGGTCGCACGGATAGCCGGATCAGAACAAAAGCTAACAACTACGCAACTTACTAT GCCGACTCAGTG AAGGGCCAGGTTCACCATTGTATTGTGGTCCGACGGGATAGCAAATCCACAGTCTACCTGCAGATGGACTCTGTGA AGACAGAAGATACTGCCACCTACTATTGTATTGTGCTGACAACGGATTACTTTGACTATTGGGGACAG GGAGTGCTGGTGACAGTGAGTTCAGCTAGCACCAAGGGACCCATCGGTCTTCCCCCCTGGCCCCATGCGAGAGCACCCTC CGAGAGCACAAGACCAGCGGTGACGGTGTCGTGAACCGGTGACGGTGTCGTGAACTCAGGCGCT CTGACCAGCGGCGTGCACACCTTCCCAGCTGTCCTACAGTCCTCAGGACTCTACTCCCTCAGCAGCGTGGTGACCGTGCCC AGCAACTTCGGCACCCAGACCTACACCTGCAACGTAGATCACAAGCCCAGCAACACCAAGGTGGACAAGACAGTTG AGCGCAAATGTTGTGTGAGTCCCCAAATGTCCAGGAATGCCGGGGGGGGGACCGTCAGTCTTCCTCTTCCCCCCAAAAC CCAAGGACACCCTCATGATCTCCCGGACCCCTGAGGTCACGTGCGTGGTGGTGGACGTGAGCCAGGAAGACCCCGAGGT CCAGTTCAACTGGTACGTGGACGGCGTGGAGGTGCATAATGCCAAGACAAAGCCGCGGGAGGAGCAGTTCAACAGCAC GTTCCGTGTGGTCAGCGTCCTCACCGTTGTGCACCAGGACTGGCTGAACGGCAAGGAGTACAAGTGCAAGGTCTCAACA AAGGCCCTCCCAGCCCCCATCGAAAAAACCATCTCCAAAACCAAAGGCAGCCCCGAGAACCACAGGTGTACACCCTGCC | 1404 |

| Nb | Name | Type | Sequence | Len |
|---|---|---|---|---|
| 46 | Effi3_VH3_IgG2b_aa | PRT | MLVLQWVLVTALFQGVHCAVQLVESGGGLVQPGGSLKITCAASGETFTNAAMYWVRQAPGKGLEWVARIRTKANNYATYY ADSVKGRETISRDDSKSTVVLQMDSVKTEDTATYYCIVVLTTTRDYFDYWGQGVLVTVSSASTKGPSVFPLAPCSRSTSESTA ALGCLVKDYFPEPVTVSWNSGALTSGVHTFPAVLQSSGLYSLSSVVTVPSSNEGTQTYTCNVDHKPSNTKVDKTVERKCCVEC PPCPAPPVAGPSVFLEPPKPKDTLMISRTPEVTCVVVDVSHEDPEVQFNWYVDGVEVHNAKTKPREEQFNSTERVVSVLTV VHQDWLNGKEYCKVSNKGLPAPIEKTISKTKGQPREPQVTLPPSREEMTKNQVSLTCLVKGFYPSDIAVEWESNGQPENN YKTTPPMLDSDGSFELYSKLTVDKSRWQQGNVFSCSVMHEALHNHYTQKSLSLSPGK | 467 |
| 47 | Effi3_VL4_CLkappa | DNA | ATGAAGTTCCCTGCTCAGTTCCTGGGCTGATTGTCCTGCATTCCTGGGCTGACCAACCGGCGACATCGTCTGACACAGAGT CCCTCCTCCTGCCCAGTGACACCTGGAGACGCCAGCATCTATCAGTTGCCGAAGCCTCCAGAGCTCCTGACTGTCAAGGG CATTACCCTCACTGTACTGGTTCTGCAGGAGGCCAGCCGGGTCCGGAAGCTGCCGATCTATCGATGTCTAACAGAGACA GTGGAGTGCCCATAGGTTCTGAGGCAGCGGGTCTCGAGTATCCCGAAGCAGGCACTAAGCTGAGCTGAAGCTAC GGTCGCACCACTATTGCGCACAGTTTCTGCACCATCTGATGAGCAGTTGAAATCTGAACTCGGGTACCTGTGCCTGCTG AATAACTTCTATCCCAGAGAGGCAAAGTACAGTGGAAGGTGGATAACGCCCTGACGCTGAGCAAAGCAGACTACAGAGAAAC TCACAGAGCAGGACAGCAAGGACAGCACCTACAGCCTCAGCAGCACCCTGAGCTGCGAAGTCACCCATCAGGGCCTGAGCTCGCCCGTCACAAGGGGAGAGTGTTA ACAAAGTCTACCGCCTGCGAAGTCACCCATCAGGGCCTGAGCTCGCCCGTCACAAGGAGCGCTTCAACAGGGGAGAGTGTTA G | 720 |
| 48 | Effi3_VL4_CLkappa_aa | PRT | MKFPAQFLGLIVLCIPGATGDIVLTQSPSSLPVTPGEPASISCRSSQDLLITVKGITSLYWFLQKPGQSPKLLIYRMSNRDSGVPDR FSGSGSGTDFTLKISRVEAEDVGTYYCAQFLEYPHTFGAGTKLELKRTVAAPSVFIFPPSDEQLKSGTASVVCLLNNFYPREAKV QWKVDNALQSGNSQESVTEQDSKDSTYSLSSTLTLSKADYEKHKVYACEVTHQGLSSPVTKSENRGEC | 239 |
| 49 | Effi3_VL3_Clkappa | DNA | ATGAAGTTCCCTGCTCAGTTTCTGGGCCTCAGTTGACACCTGGAGAGCCAGACATCGTCTGTATTCTGACTCAGCTCCC CTCTTCCCCTGCCAGTGACACCTGGAGACGCCAGCATCTATCAGTTGCCGAAGCCTCCAGTCACTGCTGACTGTCAAGGGA ATTACCAGCTCTACTGGTTCTGCAGGAAGCCCAGTCCGAAACCGACTTTACACTGAAAATTTCGCGTGAGCTAACAGAGACAG TGGGGTGCCCGATAGGTTCTGAGCAGCGGGTCGGAATAACCCTCACACTTTCGGGCAGCACTGAAATCTGGAACTCGGGTGAAGCTACG TCGAACCTACTATTGCGCACAGTTTCTGCATCTTCCCGCACCATCTGATGAGCAGTTGAAATCGGGAACTCGGGTAACCAATCGGTCGCCCCTGCCTGTGA ATAACTTCTATCCCAGAGAGGCAAAGTACAGTGGAAGGTGGATAACGCCCTCCAATCGGGTAACCAATCGGTCGCCCTGCCTGTGA CACAGAGCAGGACAGCAAGGACAGCACCTACAGCCTCAGCAGCACCCTGAGCTGCAAAGCAGACTACAGAGAAC ACAAAGTCTACCGCCTGCGAAGTCACCCATCAGGGCCTGAGCTCGCCCGTCACAAGGAGCGCTTCAACAGGGGAGAGTGTTA G | 720 |
| 50 | Effi3_VL3_CLkappa_aa | PRT | MKFPAQFLGLIVLCIPGATGDIVLTQSPSSLPVTPGEPASISCRSSQSLLITVKGITSLYWFLQKPGQSPKLLIYRMSNRDSGVPDR FSGSGSGTDFTLKISRVEAEDVGTYYCAQFLEYPHTFGAGTKLELKRTVAAPSVFIFPPSDEQLKSGTASVVCLLNNFYPREAKV QWKVDNALQSGNSQESVTEQDSKDSTYSLSSTLTLSKADYEKHKVYACEVTHQGLSSPVTKSENRGEC | 239 |
| 51 | Effi3_VL4_C11ambda | DNA | ATGAAGTTCCCTGCTCAGTTCCTGGGCTGATTGTCCTGCATTCCTGGGCAACCGGCGACATCGTCTGACACAGAGT CCCTCCTCCTGCCCAGTGACACCTGGAGACGCCAGCATCTATCAGTTGCCGAAGCCTCCAGGACCTCCTGACTGTCAAGGG CATTACCCTCACTGTACTGGTTCTGCAGGAGGCCAGCCGGGTCCGGAAGCTGCCGATCTATCGATGTCTAACAGAGACA GTGGAGTGCCCATAGGTTCTGAGGCAGCGGGTCTCGAGTATCCCGAAGCAGGCACTAAGCTGGACTGTGAAGCGTGG TCAGCCCAAGGCTGCCCCTCCGTCACTCTGTTCCCGCCCTCCTCTGAGGAGCTTCAAGCTGCCAACAAGGCCACACTGTGTG | 720 |

-continued

| Nb | Name | Type | Sequence | Len |
|---|---|---|---|---|
| | | | TCTCATAAGTGACTTCTACCGGAGCCGTGACAGTGGCCTGGAAGGCAGATAGCAGCCCCGTCAAGGCGGGAGTGGAG<br>ACCACCACACCCTCCAAACAAAGCAACAACAAGTACGGGCCAGCAGCTATCTGAGCCTGAGCCTGAGCAGTGGAAGT<br>CCCACAGAAGCTACAGCTGCCAGGTCACGCATGAAGGGAGCACCGTGGAGAGACAGTGGCCCCTACAGAATGTTCAT<br>AG | |
| 52 | Effi3_VL4_CL1lambda_aa | PRT | MKEPAQFLGLLIVLCIPGATGDIVLTQSPSSLPVTPGEPASISCRSSQDLLTVKGITSLYWELQKPGQSPKLLIYRMSNRDSGVPDR<br>FSGSGSGTDFTLKISRVEAEDVGTYYCAQFLEYPHTFGAGTKLELKRGQPKAAPSVTLFPPSSEELQANKATLVCLISDFYPGAVT<br>VAWKADSSPVKAGVETTTPSKQSNNKYAASSYLSLTPEQWKSHRSYSCQVTHEGSTVEKTVAPTECS | 239 |
| 53 | Effi3_VL3_CL1lambda | DNA | ATGAAGTTTCCTGCTCAGTTTCTGGGCTTGCTGATTGTGCTGTATTCTGGGCTACCGGAGACATGTCTGACTCAGTCCC<br>CCTCTTCCCTGCCAGTGACACCTGGAGAGCCAGCATCTATCAGTTGCCGAAGCTCCCAGTCTCACTCACTGCTGACTGTCAAGGGA<br>ATTACCAGCCTGTACTGGTTCCTGCAGAAGCCCGGACAGTCCCCTAAACTGCTGATCTATCGGATGTCTAACAGACAG<br>TGGGGTGCCCGATAGGTTCTCAGGCAGCGGCTCCGAAACCGACTTTACACTGAAAATTTCTCGGTGGAGGCTGAAGATG<br>TCGGAACTACTATTGCGCACAGTTTCTGGAATACCCTCACACTTTCGGGGCAGGCACTAAGCTGGAGCTGAAGCGTGGT<br>CAGCCCAAGGCTGCCCCTCCGTCACTCTGTTCCCGCCATCTAGTGAGGAGCTTCAAGCCAACAAGGCCACACTGGTGGTGT<br>CTCATAAGTGACTTCTACCCGGAGCCGTGACAGTGGCCTGGAAGGCAGATAGCAGCCCCGTCAAGGCGGGAGTGGAG<br>ACCACCACACCCTCCAAACAAAGCAACAACAAGTACGCGGCCAGCAGCTATCTGAGCCTGACGCCTGAGCAGTGGAAGT<br>CCCACAGAAGCTACAGCTGCCAGGTCACGCATGAAGGGAGCACCGTGGAGAGACAGTGGCCCCTACAGAATGTTCAT<br>AG | 720 |
| 54 | Effi3_VL3_CL1lambda_aa | PRT | MKFPAQFLGLLIVLCIPGATGDIVLTQSPSSLPVTPGEPASISCRSSQSLLTVKGITSLYWFLQKPGQSPKLLIYRMSNRDSGVPDR<br>FSGSGSETDFTLKISRVEAEDVGTYYCAQFLEYPHTFGAGTKLELKRGQPKAAPSVTLFPPSSEELQANKATLVCLISDFYPGAVT<br>VAWKADSSPVKAGVETTTPSKQSNNKYAASSYLSLTPEQWKSHRSYSCQVTHEGSTVEKTVAPTECS | 239 |
| 55 | CD127 peptide | PRT | ESGYAQNGDLEDAELDDYSFSCYSQLE | 27 |
| 56 | MD707-3 VH | PRT | AVHLVESGGGLVQPKESLKISCAASGFTESNAAMYWVRQAPGKGLEWVARIRTKANNYATYYAESVKGRETISRDDSKSMVY<br>LQMDNVKTDDTAMYYCIVVLTTTRDYFDIWGQGVMVTVSS | 123 |
| 57 | MD707-3 VL | PRT | DIVLTQAPLSVSVTPGESASISCRSSQSLLTVKGITSLYWELQKPGKSPQLLIYRMSNLASGVPDRERGSSETDFTLKISKVETED<br>VGVYYCAQFLEYPHTFGAGTKLELKR | 113 |

REFERENCES

Adams, A. B., Pearson, T. C., and Larsen, C. P. (2003). Heterologous immunity: an overlooked barrier to tolerance. Immunol. Rev. 196, 147-160.

Albuquerque, A. S., Cortesão, C. S., Foxall, R. B., Soares, R. S., Victorino, R. M. M., and Sousa, A. E. (2007). Rate of increase in circulating IL-7 and loss of IL-7Ralpha expression differ in HIV-1 and HIV-2 infections: two lymphopenic diseases with similar hyperimmune activation but distinct outcomes. J. Immunol. Baltim. Md. 1950 178, 3252-3259.

Al-Lazikani, B., Lesk, A. M., and Chothia, C. (1997). Standard conformations for the canonical structures of immunoglobulins. J. Mol. Biol. 273, 927-948.

Almagro, J. C., Teplyakov, A., Luo, J., Sweet, R. W., Kodangattil, S., Hernandez-Guzman, F., and Gilliland, G. L. (2014). Second antibody modeling assessment (AMA-II). Proteins 82, 1553-1562.

Armour, K. L., Clark, M. R., Hadley, A. G., and Williamson, L. M. (1999). Recombinant human IgG molecules lacking Fcgamma receptor I binding and monocyte triggering activities. Eur. J. Immunol. 29, 2613-2624.

Broux, B., Hellings, N., Venken, K., Rummens, J.-L., Hensen, K., Van Wijmeersch, B., and Stinissen, P. (2010). Haplotype 4 of the multiple sclerosis-associated interleukin-7 receptor alpha gene influences the frequency of recent thymic emigrants. Genes Immun. 11, 326-333.

Bruhns, P., Iannascoli, B., England, P., Mancardi, D. A., Fernandez, N., Jorieux, S., and Daëron, M. (2009). Specificity and affinity of human Fcgamma receptors and their polymorphic variants for human IgG subclasses. Blood 113, 3716-3725.

Chan, A. C., and Carter, P. J. (2010). Therapeutic antibodies for autoimmunity and inflammation. Nat. Rev. Immunol. 10, 301-316.

Chothia, C., and Lesk, A. M. (1987). Canonical structures for the hypervariable regions of immunoglobulins. J. Mol. Biol. 196, 901-917.

Datta-Mannan, A., Witcher, D. R., Tang, Y., Watkins, J., Jiang, W., and Wroblewski, V. J. (2007). Humanized IgG1 variants with differential binding properties to the neonatal Fc receptor: relationship to pharmacokinetics in mice and primates. Drug Metab. Dispos. Biol. Fate Chem. 35, 86-94.

Desmet, J., Spriet, J., and Lasters, I. (2002). Fast and accurate side-chain topology and energy refinement (FASTER) as a new method for protein structure optimization. Proteins 48, 31-43.

Ewert, S., Honegger, A., and Plückthun, A. (2003). Structure-based improvement of the biophysical properties of immunoglobulin VH domains with a generalizable approach. Biochemistry (Most.) 42, 1517-1528.

Haudebourg, T., Poirier, N., and Vanhove, B. (2009). Depleting T-cell subpopulations in organ transplantation. Transpl. Int. Off. J. Eur. Soc. Organ Transplant. 22, 509-518.

Hinton, P. R., Johlfs, M. G., Xiong, J. M., Hanestad, K., Ong, K. C., Bullock, C., Keller, S., Tang, M. T., Tso, J. Y., Vasquez, M., et al. (2004). Engineered human IgG antibodies with longer serum half-lives in primates. J. Biol. Chem. 279, 6213-6216.

Honegger, A., Malebranche, A. D., Rothlisberger, D., and Pluckthun, A. (2009). The influence of the framework core residues on the biophysical properties of immunoglobulin heavy chain variable domains. Protein Eng. Des. Sel. PEDS 22, 121-134.

Idusogie, E. E., Presta, L. G., Gazzano-Santoro, H., Totpal, K., Wong, P. Y., Ultsch, M., Meng, Y. G., and Mulkerrin, M. G. (2000). Mapping of the C1q binding site on rituxan, a chimeric antibody with a human IgG1 Fc. J. Immunol. Baltim. Md. 1950 164, 4178-4184.

Jariwala, S. P., Abrams, E., Benson, A., Fodeman, J., and Zheng, T. (2011). The role of thymic stromal lymphopoietin in the immunopathogenesis of atopic dermatitis. Clin. Exp. Allergy J. Br. Soc. Allergy Clin. Immunol. 41, 1515-1520.

Jones, P. T., Dear, P. H., Foote, J., Neuberger, M. S., and Winter, G. (1986). Replacing the complementarity-determining regions in a human antibody with those from a mouse. Nature 321, 522-525.

Labrijn, A. F., Buijsse, A. O., van den Bremer, E. T. J., Verwilligen, A. Y. W., Bleeker, W. K., Thorpe, S. J., Killestein, J., Polman, C. H., Aalberse, R. C., Schuurman, J., et al. (2009). Therapeutic IgG4 antibodies engage in Fab-arm exchange with endogenous human IgG4 in vivo. Nat. Biotechnol. 27, 767-771.

Lazar, G. A., Dang, W., Karki, S., Vafa, O., Peng, J. S., Hyun, L., Chan, C., Chung, H. S., Eivazi, A., Yoder, S. C., et al. (2006). Engineered antibody Fc variants with enhanced effector function. Proc. Natl. Acad. Sci. U.S.A 103, 4005-4010.

Martin, A. C. R. (2001). Protein Sequence and Structure Analysis of Antibody Variable Domains. In Antibody Engineering, D. R. Kontermann, and D. S. Dübel, eds. (Springer Berlin Heidelberg), pp. 422-439.

Michel, L., Berthelot, L., Pettré, S., Wiertlewski, S., Lefrère, F., Braudeau, C., Brouard, S., Soulillou, J.-P., and Laplaud, D.-A. (2008). Patients with relapsing-remitting multiple sclerosis have normal Treg function when cells expressing IL-7 receptor alpha-chain are excluded from the analysis. J. Clin. Invest. 118, 3411-3419.

North, B., Lehmann, A., and Dunbrack, R. L. (2011). A new clustering of antibody CDR loop conformations. J. Mol. Biol. 406, 228-256.

Racapé., Vanhove, B., Soulillou, J.-P., and Brouard, S. (2009). Interleukin 7 receptor alpha as a potential therapeutic target in transplantation. Arch. Immunol. Ther. Exp. (Warsz.) 57, 253-261.

Richards, J. O., Karki, S., Lazar, G. A., Chen, H., Dang, W., and Desjarlais, J. R. (2008). Optimization of antibody binding to FcgammaRIIa enhances macrophage phagocytosis of tumor cells. Mol. Cancer Ther. 7, 2517-2527.

Rochman, Y., Kashyap, M., Robinson, G. W., Sakamoto, K., Gomez-Rodriguez, J., Wagner, K.-U., and Leonard, W. J. (2010). Thymic stromal lymphopoietin-mediated STAT5 phosphorylation via kinases JAK1 and JAK2 reveals a key difference from IL-7-induced signaling. Proc. Natl. Acad. Sci. U.S.A 107, 19455-19460.

Ryan, M. C., Hering, M., Peckham, D., McDonagh, C. F., Brown, L., Kim, K. M., Meyer, D. L., Zabinski, R. F., Grewal, I. S., and Carter, P. J. (2007). Antibody targeting of B-cell maturation antigen on malignant plasma cells. Mol. Cancer Ther. 6, 3009-3018.

Shields, R. L., Namenuk, A. K., Hong, K., Meng, Y. G., Rae, J., Briggs, J., Xie, D., Lai, J., Stadlen, A., Li, B., et al. (2001). High resolution mapping of the binding site on human IgG1 for Fc gamma RI, Fc gamma RII, Fc gamma RIII, and FcRn and design of IgG1 variants with improved binding to the Fc gamma R. J. Biol. Chem. 276, 6591-6604.

Shinohara, T., Nemoto, Y., Kanai, T., Kameyama, K., Okamoto, R., Tsuchiya, K., Nakamura, T., Totsuka, T., Ikuta, K., and Watanabe, M. (2011). Upregulated IL-7 receptor α expression on colitogenic memory CD4+ T cells may participate in the development and persistence of chronic colitis. J. Immunol. Baltim. Md. 1950 186, 2623-2632.

Steurer, W., Nickerson, P. W., Steele, A. W., Steiger, J., Zheng, X. X., and Strom, T. B. (1995). Ex vivo coating of islet cell allografts with murine CTLA4/Fc promotes graft tolerance. J. Immunol. Baltim. Md. 1950 155, 1165-1174.

Strohl, W. R. (2009). Optimization of Fc-mediated effector functions of monoclonal antibodies. Curr. Opin. Biotechnol. 20, 685-691.

Taylor, B. C., Zaph, C., Troy, A. E., Du, Y., Guild, K. J., Comeau, M. R., and Artis, D. (2009). TSLP regulates intestinal immunity and inflammation in mouse models of helminth infection and colitis. J. Exp. Med. 206, 655-667.

Vargas-Madrazo, E., and Paz-Garcia, E. (2003). An improved model of association for VH-VL immunoglobulin domains: asymmetries between VH and VL in the packing of some interface residues. J. Mol. Recognit. JMR 16, 113-120.

Ying, S., O'Connor, B., Ratoff, J., Meng, Q., Fang, C., Cousins, D., Zhang, G., Gu, S., Gao, Z., Shamji, B., et al. (2008). Expression and cellular provenance of thymic stromal lymphopoietin and chemokines in patients with severe asthma and chronic obstructive pulmonary disease. J. Immunol. Baltim. Md. 1950 181, 2790-2798.

The invention claimed is:

1. An antibody or an antigen-binding fragment thereof, which comprises the following CDRs:
   VH-CDR1 the amino acid sequence of which is Effi3-VH3-CDR1 of SEQ ID No14;
   VH-CDR2 the amino acid sequence of which is Effi3-VH3-CDR2 of SEQ ID No16;
   VH-CDR3 the amino acid sequence of which is Effi3-VH3-CDR3 sequence of SEQ ID No18;
   VL-CDR2 the amino acid sequence of which is Effi3-VL3-CDR2 of SEQ ID No22;
   VL-CDR3 the amino acid sequence of which is Effi3-VL3-CDR3 of SEQ ID No24; and
   VL-CDR1 the amino acid sequence of which is Effi3-VL3-CDR1 of SEQ ID No20 or the amino acid sequence of which is Effi3-VL4-CDR1 of SEQ ID No26,
wherein the antibody or the antigen-binding fragment thereof binds specifically to the extracellular domain of human CD127 and is not an antagonist of CD127.

2. The antibody or fragment according to claim 1, which has one or more of the following features:
   said antibody or fragment does not inhibit human IL-7 induced phosphorylation of STAT5 in cells expressing the IL7-R;
   said antibody or fragment does not inhibit human TSLP-stimulated secretion of TARC in cells expressing the TSLP-R;
   said antibody or fragment is not an agonist of human CD127;
   said antibody or fragment does not increase human IL-7 induced phosphorylation of STAT5 in cells expressing the IL7-R;
   said antibody or fragment does not increase human TSLP-stimulated secretion of TARC in cells expressing the TSLP-R.

3. The antibody or an antigen-binding fragment thereof according to claim 1, wherein said antibody or antigen-binding fragment thereof comprises a heavy chain and a light chain wherein:
   the heavy chain comprises the VH-CDR1 of sequence SEQ ID No14, the VH-CDR2 of sequence SEQ ID No16, the VH-CDR3 of sequence SEQ ID No18, and
   the light chain comprises the VL-CDR1 of sequence SEQ ID No20 or 26, the VL-CDR2 of sequence SEQ ID No22, the VL-CDR3 of sequence SEQ ID No24.

4. The antibody or antigen-binding fragment thereof according to claim 3 wherein the heavy chain and/or the light chain comprise in their frameworks one or several of the following amino acid residues at positions identified with respect to Kabat numbering:

in the VH sequence: at position 3 a residue Q, at position 15 a residue G, at position 16 a residue G, at position 21 a residue T, at position 80 a residue T, at position 87 a residue S, at position 91 a residue E, at position 95 a residue T, at position 118 a residue L, and/or in the VL sequence: at position 7 a residue S, at position 9 a residue S, at position 11 a residue L, at position 12 a residue P, at position 18 a residue P, at position 47 a residue Q, at position 50 a residue K, at position 68 a residue S, at position 73 a residue G or a residue E, preferably a residue E, at position 82 a residue R, at position 85 a residue A, at position 90 a residue T.

5. The antibody or antigen-binding fragment thereof according to claim 3 which comprises:
(i) a heavy chain and a light chain wherein the light chain that comprises the VL4-CDR1 of SEQ ID No26 and has an amino acid residue at position 73 which is a residue G or
(ii) preferably a heavy chain and a light chain wherein the light chain that comprises the VL3-CDR1 of SEQ ID No20 and has an amino acid residue at position 73 which is a residue E.

6. The antibody or antigen-binding fragment thereof according to claim 4 wherein the heavy chain and/or the light chain comprise in their frameworks all the following amino acid residues:

in the VH sequence: at position 3 a residue Q, at position 15 a residue G, at position 16 a residue G, at position 21 a residue T, at position 80 a residue T, at position 87 a residue S, at position 91 a residue E, at position 95 a residue T, at position 118 a residue L, and/or in the VL sequence: at position 7 a residue S, at position 9 a residue S, at position 11 a residue L, at position 12 a residue P, at position 18 a residue P, at position 47 a residue Q, at position 50 a residue K, at position 68 a residue S, at position 73 a residue E, at position 82 a residue R, at position 85 a residue A, at position 90 a residue T.

7. The antibody or antigen-binding fragment thereof according to claim 1, which comprises:
a heavy chain comprising or consisting of the sequence of Effi3-VH3 the amino acid sequence of which is sequence of SEQ ID No 2; and
a light chain comprising or consisting of the sequence of Effi3-VL3 the amino acid sequence of which is sequence of SEQ ID No 4 or the sequence of Effi3-VL4 the amino acid sequence of which is sequence of SEQ ID No 6.

8. The antibody or antigen-binding fragment thereof according to claim 1, which has cytotoxic activity on CD127-positive cells.

9. The antigen-binding fragment of an antibody according to claim 1 which is one of the following fragments:
Fv fragment consisting of the VL and VH chains associated together by hydrophobic interactions;
dsFv fragment wherein the VH:VL heterodimer is stabilised by a disulphide bond;
scFv fragment wherein the VL and VH chains are connected to one another via a flexible peptide linker thus forming a single-chain protein;
Fab fragment which is a monomeric fragment comprising the entire L chain, and a VH-CH1 fragment of the H chain, bound together through a disulfide bond;
Fab' fragment; or
F(ab')2 fragment which comprises two Fab' fragments, and additionally a portion of the hinge region of an antibody.

10. The antibody or an antigen-binding fragment thereof according to claim 1 which recognizes a polypeptide consisting of or comprising the epitope with the sequence of SEQ ID No55.

11. The antibody according to claim 1, wherein said antibody is a humanized monoclonal antibody, which comprises:
a heavy chain comprising the constant region of IgG1m-E333A the amino acid sequence of which being the sequence of SEQ ID No28, and
a light chain comprising the constant region of CLkappa the amino acid sequence of which being the sequence of SEQ ID No34.

12. The antibody according to claim 1, wherein said antibody is a humanized monoclonal antibody, which comprises:
a heavy chain comprising the constant region of IgG4m-S228P the amino acid sequence of which being the sequence of SEQ ID No30, or the constant region of IgG2b the amino acid sequence of which being sequence of SEQ ID No32 and
a light chain comprising the constant region of CLkappa the amino acid sequence of which being the sequence of SEQ ID No34 or the constant sequence of CLlambda the amino acid sequence of which being the sequence of SEQ ID No36.

13. A chimeric molecule comprising an antibody or a fragment thereof according to claim 1, which is
a complex molecule having a plurality of functional domains which collectively provides recognition, binding, anchoring, signalling functions to said molecule, said complex molecule being in particular a chimeric antigen receptor (CAR) comprising:
(i) an ectodomain which is from a scFv fragment of said antibody or antigen-binding fragment according to any one of claims 1 to 12 or is such scFv fragment,
(ii) a transmembrane domain for anchoring into a cell membrane, and
(iii) an endodomain which comprises at least one intracellular signalling domain, (i), (ii) and (iii) being one or more associated recombinant molecule(s), in particular one or more fusion protein(s).

14. The chimeric molecule according to claim 13, wherein said molecule is a chimeric antigen receptor which comprises at least 2 signalling domains, wherein the signalling domains collectively enable at least one of the following properties:
initiation of T cell activation,
T cell mediated cytotoxicity,
amplification of the T cell activation signal or costimulation of said signal.

15. An isolated polynucleotide encoding an antibody or an antigen-binding fragment according to claim 1.

16. The polynucleotide according to claim 15, comprising the sequences of SEQ ID No 13, 15, 17, 19, 21 and 23, or the sequences of SEQ ID No13, 15, 17, 25, 21 and 23.

17. A cell comprising an antibody or an antigen-binding fragment according claim 1.

18. A method of preparation of Chimeric Antigen Receptor (CAR) which comprises the steps of:
a. providing a polynucleotide encoding an antibody or an antigen-binding fragment thereof according to claim 1,
b. recombining said polynucleotide of a) at its C-terminal end with polynucleotides encoding from N- to C-terminal a transmembrane domain and at least one signalling domain suitable for providing stimulatory signal(s) to a cell, and c. expressing the recombinant molecule obtained in b) in a cell.

19. A pharmaceutical composition which comprises as an active ingredient, an antibody or an antigen-binding fragment thereof according to claim 1.

20. The pharmaceutical composition of claim 19, wherein the composition further comprises at least one further therapeutic agent selected from the group consisting of a chemotherapeutic agent, radiotherapeutic agent, immunotherapeutic agent, a probiotic, and an antibiotic.

21. The pharmaceutical composition according to claim 20 wherein the further therapeutic agent is an immunotherapeutic agent comprising a T cell, a T cell bearing a CAR molecule, or a CAR molecule targeting a cell receptor or antigen.

22. A method for treating a disease comprising administrating to a subject in need thereof a pharmaceutical composition comprising an antibody or an antigen-binding fragment thereof according to claim 1, wherein the disease is an autoimmune disease, an allergic disease, a transplant rejection, a respiratory disease, a chronic viral infection or cancer.

23. The method of claim 22, wherein the disease is a cancer associated with CD127+ cell, a cancer associated with proliferation of CD127 positive cells and/or a cancer associated with an infiltration of CD127 positive cells.

24. The method of claim 23, wherein the cancer is selected in the group consisting of breast cancer, renal cancer, bladder cancer, lung cancer, pancreatic cancer, a T cell cutaneous lymphoma, Sezary lymphoma, an acute lymphoblastoid leukemia with gain-mutation of the IL7-R/TSLP pathway, and mesothelioma.

25. The method of claim 22, wherein said method further comprises: (i) administering simultaneously, separately, or sequentially a chemotherapeutic agent, a radiotherapeutic agent, an immunotherapeutic agent, a probiotic, or an antibiotic; or (ii) performing surgery either simultaneously, separately, or sequentially.

26. The antibody or antigen-binding fragment thereof according to claim 8, which subsequent to the binding of said antibody or antigen-binding fragment thereof to CD127, recruits effector immune cells expressing Fc receptors, said recruitment being Fc-dependent.

27. The antibody according to claim 11, comprising a heavy chain of Effi3-VH3-IgG1 m-E333A (SEQ ID No: 42).

28. The antibody according to claim 11, comprising a light chain of Effi3-VL3-CLkappa the amino acid sequence of which being the sequence of SEQ ID No50 or of Effi3-VL4-CLkappa the amino acid sequence of which being the sequence of SEQ ID No48.

* * * * *